US010406202B2

(12) United States Patent
Soliman et al.

(10) Patent No.: US 10,406,202 B2
(45) Date of Patent: *Sep. 10, 2019

(54) THERAPEUTIC VITAMIN D CONJUGATES

(71) Applicant: Extend Biosciences, Inc., Newton, MA (US)

(72) Inventors: Tarik Soliman, Cambridge, MA (US); Laura M. Hales, Cambridge, MA (US); Daniel B. Hall, Easton, MA (US); Christopher So, Henderson, NV (US); Howard P. Sard, Arlington, MA (US); Vishnumurthy Hegde, Chelmsford, MA (US)

(73) Assignee: Extend Biosciences, Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,046

(22) Filed: Jul. 12, 2018

(65) Prior Publication Data

US 2018/0311307 A1 Nov. 1, 2018

Related U.S. Application Data

(63) Continuation of application No. 15/430,449, filed on Feb. 11, 2017, which is a continuation of application No. 14/919,601, filed on Oct. 21, 2015, now Pat. No. 9,585,934.

(60) Provisional application No. 62/067,388, filed on Oct. 22, 2014, provisional application No. 62/244,181, filed on Oct. 20, 2015.

(51) Int. Cl.
*A61K 9/00* (2006.01)
*A61K 38/10* (2006.01)
*A61K 38/22* (2006.01)
*A61K 47/55* (2017.01)
*A61K 47/60* (2017.01)

(52) U.S. Cl.
CPC ............ *A61K 38/10* (2013.01); *A61K 9/0019* (2013.01); *A61K 38/22* (2013.01); *A61K 47/551* (2017.08); *A61K 47/60* (2017.08)

(58) Field of Classification Search
None
See application file for complete search history.

(56) References Cited

U.S. PATENT DOCUMENTS

| 4,179,337 A | 12/1979 | Davis |
|---|---|---|
| 4,292,250 A | 9/1981 | DeLuca et al. |
| 4,410,515 A | 10/1983 | Holick et al. |
| 4,456,553 A | 6/1984 | Oshida et al. |
| 4,675,189 A | 6/1987 | Kent et al. |
| 4,816,567 A | 3/1989 | Cabilly et al. |
| 5,108,921 A | 4/1992 | Low et al. |
| 5,116,964 A | 5/1992 | Capon et al. |
| 5,122,614 A | 6/1992 | Zalipsky |
| 5,214,170 A | 5/1993 | Tanabe et al. |
| 5,232,836 A | 8/1993 | Bouillon et al. |
| 5,416,016 A | 5/1995 | Low et al. |
| 5,428,023 A | 6/1995 | Russell-Jones et al. |
| 5,447,851 A | 9/1995 | Beutler et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,569,825 A | 10/1996 | Lonberg et al. |
| 5,574,018 A | 11/1996 | Habberfield et al. |
| 5,605,690 A | 2/1997 | Jacobs et al. |
| 5,625,126 A | 4/1997 | Lonberg et al. |
| 5,629,384 A | 5/1997 | Veronese et al. |
| 5,633,425 A | 5/1997 | Lonberg et al. |
| 5,661,016 A | 8/1997 | Lonberg et al. |
| 5,688,488 A | 11/1997 | Low et al. |
| 5,691,328 A | 11/1997 | Peterson et al. |
| 5,714,142 A | 2/1998 | Blaney et al. |
| 5,739,277 A | 4/1998 | Presta et al. |
| 5,767,254 A | 6/1998 | Polt |
| 5,869,466 A | 2/1999 | Russell-Jones et al. |
| 5,876,969 A | 3/1999 | Fleer et al. |
| 5,919,452 A | 7/1999 | Le et al. |
| 5,932,462 A | 8/1999 | Harris et al. |
| 6,093,701 A | 7/2000 | Wolff et al. |
| 6,100,294 A | 8/2000 | Reddy |
| 6,103,709 A | 8/2000 | Norman et al. |
| 6,121,312 A | 9/2000 | Reddy |
| 6,329,357 B1 | 12/2001 | Norman et al. |
| 6,342,225 B1 | 1/2002 | Jones et al. |
| 6,395,492 B1 | 5/2002 | Manoharan et al. |
| 6,455,714 B1 | 9/2002 | Holick et al. |
| 6,479,538 B1 | 11/2002 | Reddy |
| 6,516,294 B1 | 2/2003 | Norman |
| 6,660,843 B1 | 12/2003 | Feige et al. |
| 6,713,280 B1 | 3/2004 | Huang et al. |
| 6,787,660 B1 | 9/2004 | Armbruster et al. |
| 6,858,227 B1 | 2/2005 | Lal et al. |
| 6,858,595 B2 | 2/2005 | Hayes |
| 6,887,470 B1 | 5/2005 | Bridon et al. |
| 6,908,963 B2 | 6/2005 | Roberts |
| 6,929,797 B2 | 8/2005 | Mazess et al. |

(Continued)

FOREIGN PATENT DOCUMENTS

| CA | 2463072 C | 8/2010 |
|---|---|---|
| CA | 2966207 C | 6/2016 |

(Continued)

OTHER PUBLICATIONS (Vivo pathophysiology; http://www.vivo.colostate.edu/hbooks/pathphys/endocrine/thyroid/pth.html, accessed Sep. 22, 2018).*

(Continued)

*Primary Examiner* — James H Alstrum-Acevedo
*Assistant Examiner* — Tara L Martinez
(74) *Attorney, Agent, or Firm* — Kaplan IP Law, P.C.; Jonathan M. Kaplan

(57) ABSTRACT

The invention provides non-hormonal vitamin D conjugated via the third carbon on the vitamin D backbone to parathyroid hormone (PTH) proteins that result in increased absorption, bioavailability or circulating half-life when compared to non-conjugated forms.

26 Claims, 12 Drawing Sheets

Specification includes a Sequence Listing.

(56) References Cited

U.S. PATENT DOCUMENTS

| | | |
|---|---|---|
| 6,989,377 B2 | 1/2006 | Hayes |
| 7,045,318 B2 | 5/2006 | Ballance |
| 7,049,285 B2 | 5/2006 | Park |
| 7,057,012 B1 | 6/2006 | Gardella |
| 7,078,496 B2 | 7/2006 | Roberts |
| 7,141,547 B2 | 11/2006 | Rosen et al. |
| 7,176,278 B2 | 2/2007 | Prior |
| 7,186,797 B2 | 3/2007 | West et al. |
| 7,217,689 B1 | 5/2007 | Elliott et al. |
| 7,244,834 B2 | 7/2007 | Gardella |
| 7,256,253 B2 | 8/2007 | Bridon et al. |
| 7,371,721 B2 | 5/2008 | Henriksen |
| 7,390,509 B2 | 6/2008 | Giordano |
| 7,402,662 B2 | 7/2008 | Athwal |
| 7,511,095 B2 | 3/2009 | Roberts |
| 7,557,183 B2 | 7/2009 | DiMarchim |
| 7,560,123 B2 | 7/2009 | Giordano |
| 7,579,324 B2 | 8/2009 | Burnet et al. |
| 7,601,332 B2 | 10/2009 | Vlahov et al. |
| 7,608,681 B2 | 10/2009 | Dennis et al. |
| 7,741,286 B2 | 6/2010 | Bridon et al. |
| 7,741,453 B2 | 6/2010 | Erickson et al. |
| 7,803,777 B2 | 9/2010 | DeFrees |
| 7,834,088 B2 | 11/2010 | Roberts |
| 7,947,280 B2 | 5/2011 | Ashley et al. |
| 7,982,018 B2 | 7/2011 | Ulich et al. |
| 8,071,678 B2 | 12/2011 | Roberts |
| 8,076,476 B2 | 12/2011 | Reeves et al. |
| 8,101,587 B2 | 1/2012 | Giordano |
| 8,129,348 B2 | 3/2012 | Besman et al. |
| 8,178,495 B2 | 5/2012 | Chilkoti |
| 8,188,064 B2 | 5/2012 | Clagett-dame |
| 8,188,223 B2 | 5/2012 | Beimaert et al. |
| 8,252,755 B2 | 8/2012 | Yamada et al. |
| 8,329,876 B2 | 12/2012 | Roberts |
| 8,551,937 B2 | 10/2013 | Wakabayashi et al. |
| 8,609,629 B2 | 12/2013 | Giordano |
| 8,779,109 B2 | 7/2014 | Behrens et al. |
| 8,785,603 B2 | 7/2014 | Sahakian et al. |
| 8,796,443 B2 | 8/2014 | Khvorova et al. |
| 8,968,790 B2 | 3/2015 | Mousa |
| 8,993,248 B2 | 3/2015 | Beckert |
| 9,173,950 B2 | 11/2015 | Soliman et al. |
| 9,271,519 B2 | 3/2016 | Giordano |
| 9,289,507 B2 | 3/2016 | Soliman et al. |
| 9,585,934 B2 | 3/2017 | Soliman et al. |
| 9,616,109 B2 | 4/2017 | Soliman et al. |
| 9,789,197 B2 | 10/2017 | Soliman et al. |
| 9,863,963 B2 | 1/2018 | Poppe |
| 9,884,124 B2 | 2/2018 | Soliman et al. |
| 9,897,615 B2 | 2/2018 | Martens |
| 10,046,058 B2 | 8/2018 | Rosendahl |
| 10,222,388 B2 | 3/2019 | Soskic et al. |
| 2001/0007907 A1 | 7/2001 | Reddy |
| 2002/0025929 A1* | 2/2002 | Sato ............... A61K 38/29 514/11.8 |
| 2002/0136731 A1 | 9/2002 | Mazess et al. |
| 2002/0141996 A1 | 10/2002 | Le et al. |
| 2003/0105224 A1 | 6/2003 | Roberts |
| 2003/0113305 A1 | 6/2003 | Osborne et al. |
| 2003/0125309 A1 | 7/2003 | Reddy |
| 2003/0129194 A1 | 7/2003 | Mazess et al. |
| 2003/0171605 A1 | 9/2003 | Reddy |
| 2003/0195171 A1 | 10/2003 | Daifotis |
| 2003/0203359 A1 | 10/2003 | Uhlmann et al. |
| 2004/0132104 A1 | 7/2004 | Sackrison et al. |
| 2004/0186063 A1 | 9/2004 | Gutke et al. |
| 2005/0059129 A1 | 3/2005 | Park |
| 2005/0119242 A1 | 6/2005 | Deluca |
| 2005/0148763 A1 | 7/2005 | Sekimori |
| 2005/0176685 A1 | 8/2005 | Daifotis |
| 2005/0192256 A1 | 9/2005 | Melnick |
| 2005/0260237 A1 | 11/2005 | Byun et al. |
| 2005/0261250 A1 | 11/2005 | Daifotis |
| 2005/0276843 A1 | 12/2005 | Quay |
| 2006/0045880 A1 | 3/2006 | Krieg |
| 2006/0069021 A1 | 3/2006 | Costantino |
| 2006/0153839 A1 | 7/2006 | Mohamed et al. |
| 2006/0199765 A1 | 9/2006 | Gardella |
| 2006/0258630 A1 | 11/2006 | Adorini |
| 2007/0032461 A1 | 2/2007 | Adorini |
| 2007/0249571 A1 | 10/2007 | Tamarkin |
| 2008/0064668 A1 | 3/2008 | Uskokovic |
| 2008/0188548 A1 | 8/2008 | Reddy |
| 2008/0199960 A1 | 8/2008 | Juliano et al. |
| 2008/0242595 A1 | 10/2008 | Doyle |
| 2008/0280859 A1 | 11/2008 | Adorini |
| 2008/0318911 A1 | 12/2008 | Uskokovic |
| 2009/0099140 A1 | 4/2009 | Jankowski |
| 2009/0131360 A1 | 5/2009 | Woolf et al. |
| 2009/0176253 A1 | 7/2009 | Bieniarz et al. |
| 2009/0247544 A1 | 10/2009 | Morgan |
| 2009/0298799 A1 | 12/2009 | Adorini |
| 2009/0298800 A1 | 12/2009 | Uskokovic |
| 2009/0305986 A1 | 12/2009 | Belouski et al. |
| 2009/0324745 A1 | 12/2009 | Giordano |
| 2010/0015046 A1 | 1/2010 | Govindan et al. |
| 2010/0074885 A1 | 3/2010 | Schiff et al. |
| 2010/0098779 A1 | 4/2010 | Balzer |
| 2010/0104626 A1 | 4/2010 | Leamon et al. |
| 2010/0168033 A1 | 7/2010 | Ghigo et al. |
| 2010/0234303 A1 | 9/2010 | Millar et al. |
| 2010/0260836 A1 | 10/2010 | Giordano |
| 2010/0310678 A1 | 12/2010 | Giordano |
| 2010/0323973 A1 | 12/2010 | Leamon et al. |
| 2011/0028394 A1 | 2/2011 | Karim |
| 2011/0166063 A1 | 7/2011 | Bossard et al. |
| 2011/0268793 A9 | 11/2011 | Giordano |
| 2011/0293579 A1 | 12/2011 | Nielsen et al. |
| 2011/0312027 A1 | 12/2011 | Young et al. |
| 2012/0028887 A1 | 2/2012 | Shai et al. |
| 2012/0121726 A1 | 5/2012 | Giordano |
| 2012/0129766 A1 | 5/2012 | Boettcher et al. |
| 2012/0129767 A1 | 5/2012 | Tulipano et al. |
| 2012/0165377 A1 | 6/2012 | Takizawa et al. |
| 2012/0177646 A1 | 7/2012 | Belouski et al. |
| 2013/0085121 A1 | 4/2013 | Wang |
| 2013/0129724 A1 | 5/2013 | Boettcher et al. |
| 2013/0143241 A1 | 6/2013 | Martens |
| 2013/0149385 A1 | 6/2013 | Mousa |
| 2013/0164310 A1 | 6/2013 | Annathur et al. |
| 2013/0172251 A1 | 7/2013 | Kangawa et al. |
| 2013/0231277 A1 | 9/2013 | Mohammadi et al. |
| 2013/0261013 A1 | 10/2013 | Baltzer et al. |
| 2013/0295593 A1 | 11/2013 | Beckert |
| 2013/0331316 A1 | 12/2013 | Mohammadi et al. |
| 2014/0050802 A1 | 2/2014 | Balzer |
| 2014/0058063 A1 | 2/2014 | Vlahov et al. |
| 2014/0106027 A1 | 4/2014 | Giordano |
| 2014/0135260 A1 | 5/2014 | Dong et al. |
| 2014/0170704 A1 | 6/2014 | Young et al. |
| 2014/0179560 A1 | 6/2014 | Olson et al. |
| 2014/0194352 A1 | 7/2014 | Ling et al. |
| 2014/0200261 A1 | 7/2014 | Hoge et al. |
| 2014/0213512 A1 | 7/2014 | Ellison et al. |
| 2014/0256626 A1 | 9/2014 | Santi et al. |
| 2014/0323396 A1 | 10/2014 | Belouski et al. |
| 2014/0370616 A1 | 12/2014 | Gupta |
| 2015/0065420 A1 | 3/2015 | Soliman et al. |
| 2015/0104469 A1 | 4/2015 | Soliman et al. |
| 2016/0047825 A1 | 2/2016 | Poppe |
| 2016/0113993 A1 | 4/2016 | Soliman et al. |
| 2016/0114001 A1 | 4/2016 | Soliman et al. |
| 2016/0114049 A1 | 4/2016 | Soliman et al. |
| 2016/0144049 A1 | 5/2016 | Soliman et al. |
| 2016/0151510 A1 | 6/2016 | Rosendahl |
| 2016/0151511 A1 | 6/2016 | Rosendahl |
| 2016/0195556 A1 | 7/2016 | Soskic |
| 2017/0115313 A9 | 4/2017 | Soskic |
| 2017/0216449 A1 | 8/2017 | Soliman et al. |
| 2017/0252410 A1 | 9/2017 | Soliman et al. |

(56) References Cited

U.S. PATENT DOCUMENTS

| | | |
|---|---|---|
| 2018/0271792 A1 | 9/2018 | Mantripragada |
| 2018/0318429 A1 | 11/2018 | Rosendahl |

FOREIGN PATENT DOCUMENTS

| | | |
|---|---|---|
| CN | 100381177 C | 4/2008 |
| EP | 0528271 * | 5/1992 |
| EP | 0312360 B1 | 6/1992 |
| EP | 0486525 B1 | 6/1994 |
| EP | 0804456 B1 | 8/2002 |
| EP | 1477496 A1 | 11/2004 |
| EP | 0981523 B1 | 12/2005 |
| EP | 1151102 B1 | 4/2006 |
| EP | 1434589 B1 | 12/2008 |
| EP | 1931711 B1 | 4/2009 |
| EP | 2085406 A1 | 8/2009 |
| EP | 1601646 B1 | 7/2011 |
| EP | 2372365 A1 | 10/2011 |
| EP | 2423233 A2 | 2/2012 |
| EP | 2288375 B1 | 4/2012 |
| EP | 2481427 A1 | 8/2012 |
| EP | 2530068 A1 | 12/2012 |
| EP | 2316854 B1 | 12/2013 |
| EP | 2695617 A2 | 2/2014 |
| EP | 3030243 B1 | 7/2017 |
| WO | 199110741 A1 | 7/1991 |
| WO | 1992014493 A1 | 9/1992 |
| WO | 1992016221 A1 | 10/1992 |
| WO | 1993007883 A1 | 4/1993 |
| WO | 1993012145 A1 | 6/1993 |
| WO | 1995010302 A1 | 4/1995 |
| WO | 1996033735 A1 | 10/1996 |
| WO | 1996034096 A1 | 10/1996 |
| WO | 1997034637 A2 | 9/1997 |
| WO | 1998024893 A2 | 6/1998 |
| WO | 9916452 A1 | 4/1999 |
| WO | 9967211 A1 | 12/1999 |
| WO | 1999061055 A1 | 12/1999 |
| WO | 0039278 A2 | 7/2000 |
| WO | 2000066090 A1 | 11/2000 |
| WO | 2000074721 A1 | 12/2000 |
| WO | 2000069900 A3 | 2/2001 |
| WO | 2001045746 A3 | 10/2001 |
| WO | 2002062844 A2 | 8/2002 |
| WO | 2002066511 A2 | 8/2002 |
| WO | 2002076489 A1 | 10/2002 |
| WO | 2003011213 A2 | 2/2003 |
| WO | 2002046227 A3 | 4/2003 |
| WO | 2003031581 A2 | 4/2003 |
| WO | 2003025139 A3 | 8/2003 |
| WO | 2003086415 A1 | 10/2003 |
| WO | 2004009124 A2 | 1/2004 |
| WO | 2004011498 A3 | 6/2004 |
| WO | 2004041865 A3 | 7/2004 |
| WO | 2004069159 | 8/2004 |
| WO | 2004080922 A2 | 9/2004 |
| WO | 2004084948 A1 | 10/2004 |
| WO | 2005051323 A2 | 6/2005 |
| WO | 2005097158 A1 | 10/2005 |
| WO | 2005105071 A1 | 11/2005 |
| WO | 2005117906 A1 | 12/2005 |
| WO | 2006117684 A1 | 11/2006 |
| WO | 2007012188 A1 | 2/2007 |
| WO | 2007035922 A2 | 3/2007 |
| WO | WO2007035922 A2 | 3/2007 |
| WO | 2007038250 A2 | 4/2007 |
| WO | 2007049941 A1 | 5/2007 |
| WO | 2006116156 A3 | 10/2007 |
| WO | 2007097934 A3 | 11/2007 |
| WO | 2007103455 A3 | 11/2007 |
| WO | 2008036841 A3 | 10/2008 |
| WO | 2008118013 A2 | 10/2008 |
| WO | 2009121884 A1 | 10/2009 |
| WO | 2011122948 A1 | 10/2011 |
| WO | 2011146902 A1 | 11/2011 |
| WO | 2011123813 A3 | 12/2011 |
| WO | 2012041451 A1 | 4/2012 |
| WO | 2012129650 A1 | 10/2012 |
| WO | 2012158962 A2 | 11/2012 |
| WO | 2012163563 A1 | 12/2012 |
| WO | WO2013172967 * | 1/2013 |
| WO | 2013033230 A1 | 3/2013 |
| WO | 2013044356 A1 | 4/2013 |
| WO | 2013044356 A9 | 5/2013 |
| WO | 2013086313 A1 | 6/2013 |
| WO | 2013102149 A1 | 7/2013 |
| WO | 2013163162 A1 | 10/2013 |
| WO | WO2013172967 A1 | 11/2013 |
| WO | 2014041024 A1 | 3/2014 |
| WO | 2013040093 A3 | 5/2014 |
| WO | 2014081864 A1 | 5/2014 |
| WO | 2014083427 A2 | 6/2014 |
| WO | 2015057836 A2 | 4/2015 |
| WO | 2015057836 A3 | 4/2015 |
| WO | 2016065042 | 4/2016 |
| WO | 2016065052 | 4/2016 |
| WO | 2016089818 A1 | 6/2016 |
| WO | 2017148883 A1 | 9/2017 |
| WO | 2018060312 A1 | 4/2018 |
| WO | 2018175250 A1 | 9/2018 |

OTHER PUBLICATIONS

Goodson et al. "Site Directed Pegylation of Recombinant Interleukin-2 At Its Glycosylation Site," Nature Biotechnology, vol. 8, Apr. 1990.

Guo et al. "Prolonged Pharmacokinetic and Pharmacodynamic Actions of a Pegylated Parathyroid Hormone (1-34) Peptide Fragment," Journal of Bone and Mineral Research, vol. 32, No. 1, Jan. 2017.

Krishnan et al. "Repurposing a novel parathyroid hormone (PTH) analog to treat hypoparathyroidism," British Journal of Pharmacology, 2017.

Na et al. "Capillary electrophoretic characterization of PEGylated human parathyroid hormone with matrix-assisted laser desorption/ionization time-of-Xight mass spectrometry," Analytical Biochemistry 331, 2004.

Abe et.al., Synthetic analogues of vitamin D3 with an oxygen atom in the side chain skeleton, FEBS Lett. 226:58-62 (1987).

Addo JK, et al., 2002, "The C19 Position of 25-Hydroxyvitamin D3 Faces Outward in the Vitamin D Sterol-Binding Pocket of Vitamin D-Binding Protein," Bioorganic & Medicinal Chemistry Letters 12: 279-281.

Ahsan, F et al., 2001, Enhanced Bioavailability of Calcitonin Formulated with Alkylglycosides following Nasal and Ocular Administration in Rats, Pharm Res 18:1742-1746.

Amiram M, et al., 2013, "A Depot-Forming Glucagon-Like Peptide-1 Fusion Protein Reduces Blood Glucose for Five Days with a Single Injection," Journal of Controlled Release 172: 144-151.

Amiram M, et al., 2013, "Injectable Protease-Operated Depots of Glucagon-Like Peptide-1 Provide Extended and Tunable Glucose Control," Proceedings of the National Academy of Sciences, USA 110(8): 2792-2797.

Arnaud J and Constans J, 1993, "Affinity Differences for Vitamin D Metabolites Associated with the Genetic Isoforms of the Human Serum Carrier Protein (DBP)," Human Genetics 92: 183-188.

Arnold, JJ et al., 2004, Correlation of Tetradecylmaltoside Induced Increases in Nasal Peptide Drug Delivery with Morphological Changes in Nasal Epithelial Cells, J Pharm Sci 93: 2205-13.

Amusch CJ, et al., 2012, "Ultrashort Peptide Bioconjugates Are Exclusively Antifungal Agents and Synergize with Cyclodextrin and Amphotericin B," Antimicrobial Agents and Chemotherapy 56(1) 1-9.

Baggio LL, et al., 2004, "A Recombinant Human Glucagon-Like Peptide (GLP)-1-Albumin Protein (Albugon) Mimics Peptidergic Activation of GLP-1 Receptor-Dependent Pathways Coupled with Satiety, Gastrointestinal Motility, and Glucose Homeostasis," Diabetes 53: 2492-2500.

Bailon P, et al., 2001, "Rational Design of a Potent, Long-Lasting Form of Interferon: a 40 kDa Branched Polyethylene Glycol-

(56) References Cited

OTHER PUBLICATIONS

Conjugated Interferon Alpha-2a for the Treatment of Hepatitis C," Bioconjugate Chemistry 12(2): 195-202.
Bao W, et al., 2013, "Novel Fusion of GLP-1 with a Domain Antibody to Serum Albumin Prolongs Protection against Myocardial Ischemia/Reperfusion Injury in the Rat," Cardiovascular Diabetology 12: 148.
Barrington P, et al., 2011, "A 5-Week Study of the Pharmacokinetics and Pharmacodynamics of LY2189265, a Novel, Long-Acting Glucagon-Like Peptide 1 Analogue, in Patients with Type 2 Diabetes," Diabetes, Obesity, and Metabolism 13:426-433.
Barrington P, et al., 2011, "LY2189265, a Long-Acting Glucagon-Like Peptide 1 Analogue, Showed a Dose-Dependent Effect on Insulin Secretion in Healthy Patients," Diabetes, Obesity, and Metabolism 13:434-438.
Ben-Shabat S, et al., 2005, "Vitamin D3-Based Conjugates for Topical Treatment of Psoriasis: Synthesis, Antiproliferative Activity, and Cutaneous Penetration Studies," Pharmaceutical Research 22(1): 50-57.
Bishop JE, et al., 1994, "Profile of Ligand Specificity of the Vitamin D Binding Protein for 1alpha-25-dihydroxyvitamin D3 and its Analogues," Journal of Bone and Mineral Research 9(8): 1277-1288.
Blouch K, et al., 1997, "Molecular Configuration and Glomerular Size Selectivity in Healthy and Nephrotic Humans," American Journal of Physiology 273 (Renal Physiology 42): F430-F437. (May 20, 1997).
Boemer et al., Human mAb From In Vitro-Primed Lymphocytes, J. Immunol, 147: 86-95 (1991).
Bouillon R, et al., 1980, "Comparative Study of the Affinity of the Serum Vitamin D Binding Protein," Journal of Steroid Biochemistry 13: 1029-1034.
Bouillon R, et al., 1991, "Vitamin D Analogues with Low Affinity for the Vitamin D Binding Protein: Enhanced in Vitro and Decreased in Vivo Activity," Journal of Bone and Mineral Research 6(10): 1051-1057.
Bouman-Theo E, et al., 2008, "A Phase I, Single and Fractionated, Ascending-Dose Study Evaluating the Safety, Pharmacokinetics, Pharmacodynamics, and Immunogenicity of an Erythropoietin Mimetic Antibody Fusion Protein (CNTO 528) in Healthy Male Subjects," Journal of Clinical Pharmacology 48: 1197-1207.
Cai Y, et al., 2013, "Long-Acting Preparations of Exenatide," Drug Design, Development, and Therapy 7: 963-970.
Camacho RC, et al., 2013, "PEGylated FGF21 Rapidly Normalizes Insulin-Stimulated Glucose Utilization in Diet-Induced Insulin Resistant Mice," European Journal of Pharmacology 715: 41-45.
Capon DJ, et al., 1989, "Designing CD4 Immunoadhesions for AIDS Therapy," Nature 337: 525-531.
Carlberg C, 2003, "Molecular Basis for the Selective Activity of Vitamin D Analogues," Journal of Cellular Biochemistry 88: 274-281.
Chae SY, et al., 2009, "Pharmacokinetic and Pharmacodynamic Evaluation of Site-Specific PEGylated Glucagon-Like Peptide-1 Analogs as Flexible Postprandial-Glucose Controllers," Journal of Pharmaceutical Sciences 98(4): 1556-1567.
Chae SY, et al., 2010, "Biochemical, Pharmaceutical, and Therapeutic Properties of Long-Acting Lithocholic Acid Derivatized Exendin-4 Analogues," Journal of Controlled Release 142: 206-213.
Chae SY, et al., 2010, "The Fatty Acid Conjugated Exendin-4 Analogues for Type 2 Antidiabetic Therapeutics," Journal of Controlled Release 144: 10-16.
Chalasani KB, et al., 2007, "Effective Oral Delivery of Insulin in Animal Models Using Vitamin B12-coated Dextran Nanoparticles," Journal of Controlled Release 122: 141-150.
Chen et al., Selection and Analysis of an Optimized Anti-VEGF Antibody: Crystal Structure of an Affinity-matured Fab, J. Mol. Biol. 293:865-881 (1999).

Chen S, et al., 2010, "Mechanism-Based Tumor-Targeting Drug Delivery System. Validation of Efficient Vitamin Receptor-Mediated Endocytosis and Drug Release," Bioconjugate Chemistry 21: 979-987.
Choi H-I, et al., 2009, "A Novel L-Ascorbic Acid and Peptide Conjugate with Increased Stability and Collagen Biosynthesis," BMB Reports 42(11): 743-746.
Clackson et al., Making antibody fragments using phage display libraries, Nature, 352: 624-628 (1991).
Clardy-James S, et al., 2013, "Synthesis, Characterization, and Pharmacodynamics of Vitamin-B12-Conjugated Glucagon-Like Peptide-1," ChemMedChem 8: 582-586.
Clark et al. Long-acting Growth Hormones Produced by Conjugation with Polyethylene Glycol, J. Biol. Chem. 271:21969-21977 (1996).
Cleland JL, et al., 2012, "A Novel Long-Acting Human Growth Hormone Fusion Protein (VRS-317): Enhanced in Vivo Potency and Half-Life," Journal of Pharmaceutical Sciences 101(8): 2744-2754.
Clemens TL, et al., 1983, "A Simple Method for Generation of Antibodies with Specificity for 1,25-Dihydroxyergocalciferol and 1,25-Dihydroxycholecalciferol," Steroids 42(5): 503-509.
Conforti A, et al., 1987, "PEG Superoxide Dismutase Derivatives: Anti-Inflammatory Activity in Carrageenan Pelurisy in Rats," Pharmacological Research Communications 19: 287-294.
Cooke NE and Haddad JG, 1989, "Vitamin D Binding Protein (Gc-Globulin)," Endocrinology Reviews 10: 294-307.
Datta-Mannan A, et al, 2012, "Influence of improved FcRn binding on the subcutaneous bioavailability of monoclonal antibodies in cynomolgus monkeys," MAbs. 4(2):267-73.
De Schepper J, et al., 2011, "Long-Acting PEGylated Human GH in Children with GH Deficiency: A Single-Dose, Dose-Escalation Trial Investigating Safety, Tolerability, Pharmacokinetics and Pharmacodynamics," European Journal of Endocrinology 165(3): 401-409.
De Smidt PC, et al., 1991, "Association of Antisense Oligonucleotides with Lipoproteins Prolongs the Plasma Half-Life and Modifies the Tissue Distribution," Nucleic Acids Research 19(17): 4695-4700.
DeLuca HF, 2008, "Evolution of our Understanding of Vitamin D," Nutrition Reviews 66(suppl. 2): S73-8.
Dennis MS, et al., 2002, "Albumin Binding as a General Strategy for Improving the Pharmacokinetics of Proteins," Journal of Biological Chemistry 277: 35035-35043.
Dennis MS, et al., 2007, "Imaging Tumors with an Albumin-Binding Fab, a Novel Tumor-Targeting Agent," Cancer Research 67: 254-261.
Ding S, et al., 2014, "Multivalent Antiviral XTEN-Peptide Conjugates with Long in Vivo Half-Life and Enhanced Solubility," Bioconjugate Chemistry 25(7): 1351-9.
Doores, K., et al., "Direct deprotected glycosyl-asparagine ligation" Chem. Commun., 1401-1403, 2006.
Elliott S, et al., 2003, "Enhancement of in Vivo Therapeutic Protein Activities through Glycoengineering," Nature Biotechnology 21: 414-421.
American Peptide Company, "The case for PEG conjugation", 2008.
Drug Lib.com, "Vitamin D2", copyright, 2006-2015.
Kojima et al. "Ghrelin: From Gene to Physiological Function", 2010, p. 185-205.
Kozbor, "A Human Hybrid Myeloma for Production of Human Monoclonal Antibodies," J. Immunol, 133: 3001 (1984).
Kutner A, et al., 1986, "Photoactivable Analogues for Labeling 25-Hydroxyvitamin D3 Serum Binding Protein and for 1,25-Dihydroxyvitamin D3 Intenstinal Receptor Protein," Bioorganic Chemistry 14: 134-147.
Langenheim JF and Chen WY, 2009, "Improving the Pharmacokinetics/Pharmacodynamics of Prolactin, GH, and Their Antagonists by Fusion to a Synthetic Albumin-Binding Peptide," Journal of Endocrinology 203:375-387.
Leamon CP and Low PS, 2001, "Folate-Mediated Targeting: From Diagnostics to Drug and Gene Delivery," Drug Discovery Today 6(1): 44-51.

(56) References Cited

OTHER PUBLICATIONS

Leamon CP and Reddy JA, 2004, "Folate-Targeted Chemotherapy," Advanced Drug Delivery Reviews 56: 1127-1141.
Lee et al., "Bivalent antibody phage display mimics natural immunoglobulin," J. Immunol. Methods 284(1-2): 119-132 (2004).
Lee et al., "High-affinity Human Antibodies from Phage-displayed Synthetic Fab Libraries with a Single," J. Mol. Biol. 340(5): 1073-1093 (2004).
Leyssens C, et al., 2014, "The Future of Vitamin D Analogues," Frontiers in Physiology 5: Article 122.
Liang S, et al., 2013, "Structural Basis for Treating Tumor Necrosis Factor alpha (TNFalpha)-associated Diseases with the Therapeutic Antibody Infliximab," Journal of Biological Chemistry 288: 13799-13807.
Liebner R, et al., 2014, "Protein HESylation for Half-Life Extension: Synthesis, Characterization and Pharmacokinetics of HESylated Anakinra," European Journal of Pharmaceutics and Biopharmaceutics 87: 378-385.
Link RP, et al., 1987, "Photoaffinity Labeling of Serum Vitamin D Binding Protein by 3-Deoxy-3-azido-25-hydroxyvitamin D3," Biochemistry 26: 3957-3964.
Lips P, 2006, "Vitamin D Physiology," Progress in Biophysics and Molecular Biology 92: 4-8.
Lonberg 2008, "Fully human antibodies from transgenic mouse and phage display platforms" Curr Opin Immunol. Aug. 2008;20(4):450-9.
Lonberg and Huszar, Intern. Rev. Immunol. 13: 65-93 (1995).
Lonberg et al.,"Antigen-specific human antibodies from mice comprising four distinct genetic modifications," Nature 368: 856-859 (1994).
Lu Y, et al., 2004, "Folate Receptor-Targeted Immunotherapy of Cancer: Mechanism and Therapeutic Potential," Advanced Drug Delivery Reviews 56: 1161-1176.
Makrides SC, et al., 1996, "Extended in Vivo Half-Life of Human Soluble Complement Receptor Type 1 Fused to a Serum Albumin-Binding Receptor," Journal of Pharmacology and Experimental Therapeutics 277(1): 534-542.
Marks et al., "By-passing Immunization Human Antibodies from V-gene Libraries Displayed on Phage," J. Mol. Biol, 222: 581-597 (1991).
Marks et al., "By-Passing Immunization: Building High Affinity Human Antibodies by Chain Shuffling," Bio. Technology 10: 779-783 (1992).
McIntyre et al., "Effects of new analogues of vitamin D on bone cells: Implications for treatment of uremic bone disease," Kidney Int. 55: 500 (1999).
McLeod et al, "The Vitamin D-binding Protein, &-Fetoprotein, Albumin Multigene Family: Detection of Transcripts in Multiple Tissues," J Biol Chem. 264(2):1260-7 (1989).
Mero A, et al., 2013, "Conjugation of Hyaluronan to Proteins," Carbohydrate Polymers 92: 2163-2170.
Misbah S, et al., 2009, "Subcutaneous immunoglobulin: opportunities and outlook," Clinical and Experimental Immunology 158(Suppl 1): 51-59.
Morrison, "Success in Specification," Nature 368: 812-813 (1994).
Mu J, et al, 2012, "FGF21 Analogs of Sustained Action Enabled by Orthogonal Biosynthesis Demonstrate Enhanced Antidiabetic Pharmacology in Rodents," Diabetes 61:505-512.
Müller DN, et al., 2011, "Vitamin D Review," Journal of the Renin-Angiotensin-Aldosterone System 12: 125-8.
Nanocs PEG Products located at: http://www.nanocs.com/PEG/VTPEG.htm.
Neary NM, et al., 2004, "Ghrelin Increases Energy Intake in Cancer Patients with Impaired Appetite: Acute, Randomized, Placebo-Controlled Trial," The Journal of Clinical Endocrinology & Metabolism 89(6): 2832-2836.
Nestor, J.J., Jr. (2007) Comprehensive Medicinal Chemistry II 2: 573-601.
Neuberger, "Generating high-avidity human Mabs in mice," Nature Biotechnol. 14: 826 (1996).
Norman AW, et al., 2001, "Ligands for the Vitamin D Endocrine System: Different Shapes Function as Agonists and Antagonists for Genomic and Rapid Response Receptors or as a Ligand for the Plasma Vitamin D Binding Protein," Journal of Steroid Biochemistry and Molecular Biology 76: 49-59.
Notice of Allowance dated Jun. 23, 2009, for U.S. Appl. No. 10/765,336.
Ono Y, 2014, "Multifunctional and Potent Roles of the 3-Hydroxypropoxy Group Provide Eldecalcitol's Benefit in Osteoporosis Treatment," Journal of Steroid Biochemistry & Molecular Biology 139: 88-97.
Park S, et al., 2014, "A Novel Delivery Platform for Therapeutic Peptides," Biochemical and Biophysical Research Communications 450(1): 13-18.
Payne RJ, et al., 2004, "Synthesis and Protein Conjugation Studies of Vitamin K Analogues," Bioorganic & Medicinal Chemistry 12: 5785-5791.
Peleg S and Posner GH, 2003, "Vitamin D Analogs as Modulators of Vitamin D Receptor Action," Current Topics in Medicinal Chemistry 3(14): 1555-72.
Petrus AK, et al., 2009, "Exploring the Implications of Vitamin B12 Conjugation to Insulin on Insulin Receptor Binding," ChemMedChem 4: 421-426.
Pfutzner, A and Forst, T, 2005, "Pulmonary insulin delivery by means of the Technosphere™ drug carrier mechanism," Expert Opin Drug Deliv 2:1097-1106.
Presta, "Antibody Engineering," Current Opinion in Biotechnology, 3:394-398 (1992).
Punj V, et al., 2004, "Effect of Vitamin D Analogue (1alpha Hydroxy D5) Immunoconjugated to Her-2 Antibody on Breast Cancer," International Journal of Cancer 108: 922-929.
Rattan, S.I., et al. (1992), "Protein Synthesis, Post translational Modifications, and Aging," Ann N Y Acad Sci 663: 48-62.
Ray R, et al., 1986, "Photoaffinity Labeling of the Rat Plasma Vitamin D Binding Protein with [26,27-3H]-25-Hydroxyvitamin D3 3beta-[N-(4-azido-2-nitrophenyl)glycinate]," Biochemistry 25(17): 4729-4733.
Reddy JA, et al., 2007, "Folate Receptor-Specific Antitumor Activity of EC131, a Folate-Maytansinoid Conjugate," Cancer Research 67: 6376-6382.
Revelle et al., "Synthesis and Biological Activity of 3beta-Fluorovitamin D3,: Comparison of the Biological Activity of 3beta-Fluorovitamin D3, and 3-Deoxyvitamin D3," J. Steroid Biochem. 22:469-474 (1985).
Riechmann et al., "Reshaping human antibodies for therapy," Nature 332:323-329 (1988).
Rosenstock J, et al., 2009, "Potential of Albiglutide, a Long-Acting GLP-1 Receptor Agonist, in Type 2 Diabetes," Diabetes Care 32(10): 1880-1886.
Salmaso S, et al., 2009, "Targeting Glioma Cells in Vitro with Ascorbate-Conjugated Pharmaceutical Nanocarriers," Bioconjugate Chemistry 20: 2348-2355.
Sasson K, et al., 2010, "Engineering Prolonged Acting Prodrugs Employing an Albumin-Binding Probe that Undergoes Slow Hydrolysis at Physiological Conditions," Journal of Controlled Release 142: 214-220.
Schlapschy M, et al., 2013,"PASylation: A Biological Alternative to PEGylation for Extending the Plasma Half-Life of Pharmaceutically Active Proteins," Protein Engineering, Design & Selection 26: 489-501.
Akamizu, et al. Pharmacokinetics, safety, and endocrine and appetite effects of ghrelin administration in young healthy subjects. European Journal of Endocrinology ,150:447-455 (2004).
Bertrand, et al. Apelin and Energy Metabolism. Frontiers in Physiology 6:115 (2015).
Caastan-Laurell, et al. Apelin, Diabetes, and Obesity. Endocrine 40(1):1-9 (2011).
Fishwild et al. High-Avidity Human IgGk Monoclonal Antibodies from a Novel Strain of Minilocus Transgenic Mice. Nature Biotechnology 14:845-851 (1996).
Frolik, et al. Anabolic and Catabolic Bone Effects of Human Parathyroid Hormone (1-34) are Predicted by Duration of Hormone Exposure. Bone 33: 372-379 (2003).

(56) References Cited

OTHER PUBLICATIONS

Presta, et al. Humanization of an Anti-Vascular Endothelial Growth Factor Monoclonal Antibody for the Therapy of Solid Tumors and Other Disorders. Cancer Research 57:4593-4599 (1997).
Satterwhite, et al. Pharmacokinetics of Teriparatide (rhPTH[1-34]) and Calcium Pharmacodynamics in Postmenopausal Women with Osteoporosis. Calcif Tissue Int. 87:485-492 (2010).
Speeckaert, et al. Biological and clinical aspects of the vitamin D binding protein (Gc-globulin) and its polymorphism. Clinica Chimica Acta 372: 33-42 (2006).
Winer K.K., et al. Synthetic Human Parathyroid Hormone 1-34 Replacement Therapy: A Randomized Crossover Trial Comparing Pump Versus Injections in the Treatment of Chronic Hypoparathyroidism. J. Clin. Endocrinal. Metab. 97(2): 391-399 (2012).
PCT Search Report and Written Opinion dated Jun. 5,2013, from PCT App. No. PCT/US13/31788, filed on Mar. 14, 2013.
Zhao et al. Potential use of cholecalciferol polyethylene glycol succinate as a novel pharmaceutical additive. Journal of Biomedical Materials Research Part A, 84A(4): 954-964,2007.
Erben and Musculoskel, "Vitamin D analogs and bone," Neuron Interact. 2(1):59-69 (2001).
Fellouse, "Synthetic antibodies from a four-amino-acid code: A dominant role for tyrosine in antigen recognition," Proc. Natl. Acad. Sci. USA 101(34): 12467-12472 (2004).
Fishburn, "The Pharmacology of PEGylation: Balancing PD with PK to Generate Novel Therapeutics," J. Pharm. Sci. 97:4167-4183 (2008).
Fisher CJ, et al., 1996, "Treatment of Septic Shock with the Tumor Necrosis Factor Receptor:Fc Fusion Protein," The New England Journal of Medicine 334: 1697-1702.
Freeman JN, et al., 2013, "Chronic central ghrelin infusion reduces blood pressure and heart rate despite increasing appetite and promoting weight gain in normotensive and hypertensive rats," Peptides 42: 35-42.
Gabizon A, et al., 2004, "Tumor Cell Targeting of Liposome-Entrapped Drugs with Phospholipid-Anchored Folic Acid-PEG Conjugates," Advanced Drug Delivery Reviews 56: 1177-1192.
Gaich G, et al., 2013, "The Effects of LY2405319, an FGF21 Analog, in Obese Human Subjects with Type 2 Diabetes," Cell Metabolism 18: 333-340.
Garay RP, et al., 2012, "Antibodies against Polyethylene Glycol in Healthy Subjects and in Patients Treated with PEG-Conjugated Agents," Expert Opinion on Drug Delivery 9(11): 1319-1323.
Gong N, et al., 2011, "Site-Specific PEGylation of Exenatide Analogues Markedly Improved Their Glucoregulatory Activity," British Journal of Pharmacology 163: 399-412.
Gourlet, P., et al. (1998), "Interaction of lipophilic VIP derivatives with recombinant VIP rPACAP 1 and VIP rPACAP receptors," Eur J Pharmacol 354: 105-111.
Haddad JG, 1995, "Plasma Vitamin D-Binding Protein (Gc-Globulin): Multiple Tasks," Journal of Steroid Biochemistry and Molecular Biology 53: 579-82.
Haddad JG, et al., 1992, "Identification of the Sterol- and Actin-Binding Domains of Plasma Vitamin D Binding Protein (Gc-Globulin)," Biochemistry 31: 7174-7181.
Haddad JG, et al., 1993, "Human Plasma Transport of Vitamin D After its Endogenous Synthesis," Journal of Clinical Investigation 91: 2552-2555.
Hakimelahi GH, et al., 2001, "Design and Synthesis of a Cephalosporin-Retinoic Acid Prodrug Activated by a Monoclonal Antibody-betaLactamase Conjugate," Bioorganic & Medicinal Chemistry 9: 2139-2147.
Harris JM and Chess RB, 2003, "Effect of PEGylation on Pharmaceuticals," Nature Reviews in Drug Discovery 2: 214-221.
Harris, "Therapeutic Monoclonals," Biochem. Soc. Transactions 23: 1035-1038 (1995).
Harvill ET and Morrison SL, 1995, "An IgG3-IL2 Fusion Protein Activates Complement, Binds Fc(gamma)RI, Generates LAK Activity and Shows Enhanced Binding to the High Affinity IL-2R," Immunotechnology 1: 95-105.
Havelund S, et al., 2004, "The Mechanism of Protraction of Insulin Determir, a Long-Acting Acylated Analog of Human Insulin," Pharmaceutical Research 21(8): 1498-1504.
Herbst RS, 2009, "Safety, Pharmacokinetics, and Antitumor Activity of AMG 386, a Selective Angiopoietin Inhibitor, in Adult Patients with Advanced Solid Tumors," Journal of Clinical Oncology 27: 3557-3565.
Hiura et. al., "Effects of Ghrelin Administration During Chemotherapy With Advanced Esophageal Cancer Patients," Cancer Jan. 26, 2012, http://onlinelibrary.wiley.com/doi/10.1002/cncr.27430/abstract.
Hoffmann E, et al., 2013, "PK Modulation of Haptenylated Peptides via Non-covalent Antibody Complexation," Journal of Controlled Release 171: 48-56.
Holick MF (editor), 2010, "Vitamin D: Physiology, Molecular Biology, and Clinical Applications," Humana Press pp. 0-1155.
Holt LJ, et al., 2008, "Anti-serum Albumin Domain Antibodies for Extending the Life-Time of Short Lived Drugs," Protein Engineering, Design, & Selection 21(5): 283-288.
Hoogenboom et al., "Multi-subunit proteins on the surface of filamentous phage: methodologies for displaying antibody (Fab) heavy andlight chains," Nucl. Acids Res., 19: 4133-4137 (1991).
Huang A, et al., "A Better Anti-Diabetic Recombinant Human Fibroblast Growth Factor 21 (rhFGF21) Modified with Polyethylene Glycol," PLoS ONE 6(6): e20669.
Hurle and Gross, "Protein engineering techniques for antibody humanization," Curr. Op. Biotech. 5:428-433 (1994).
Islam I, et al., 1994, "Evaluation of a Vitamin-Cloaking Strategy for Oligopeptide Therapeutics: Biotinylated HIV1-Protease Inhibitors," Journal of Medicinal Chemistry 37: 293-304.
Itoh N, 2014, "FGF21 as a Hepatokine, Adipokine, and Myokine in Metabolism and Diseases," Frontiers in Endocrinology 5: article 107.
Jain, "PEGylation: An Approach for Drug Delivery. A Review," Crit. Rev. Ther. Drug Carrier Syst. 25:403-447 (2008).
Jakobovits et al., "Analysis of homozygous mutant chimeric mice: Deletion of the immunoglobulin heavy-chain joining region blocks B-cell," Proc. Natl. Acad. Sci USA, 90: 2551 (1993).
Jakobovits et al.,"Germ Line Transmission and Expression of a Human-Derived Yeast Artificial Chromosome," Nature 362: 255-258 (1993).
Jevsevar S, et al., 2010, "PEGylation of Therapeutic Proteins," Biotechnology Journal 5: 113-128.
Jia ZQ, et al., 2012, "Cardiovascular Effects of a PEGylated Apelin," Peptides 38: 181-188.
Jones et al.,Replacing the Complementarity-determining Regions in a Human Antibody with those from a Mouse, Nature 321 :522-525 (1986).
Katre NV, et al., 1987, "Chemical Modification of Recombinant Interleukin 2 by Polyethylene Glycol Increases its Potency in the Murine Meth A Sarcoma Model," Proceedings of the National Academy of Sciences, USA 84: 1487-1491.
Kaul, R. and Balaram, P. (1999), "Stereochemical Control of Peptide Folding," Bioorg Med Chem 7: 105-117.
Kaya T, et al., 2009, "Covalent Labeling of Nuclear Vitamin D Receptor with Affinity Labeling Reagents Containing a Cross-linking Probe at Three Different Positions of the Parent Ligand: Structural and Biochemical Implications," Bioorganic Chemistry 37: 57-63.
Kharitonenkov A and Adams AC, 2014, "Inventing New Medicines: The FGF21 Story," Molecular Metabolism 3: 221-229.
Kharitonenkov and Shanafelt, Curr. Opin. Investig. Drugs 10:359-364 (2009), Abstract Only.
Kharitonenkov et al., "FGF-21 as a novel metabolic regulator," J. Clin. Invest. 115:1627-1635 (2005).
Kim KH and Lee M-S, 2014, "FGF21 as a Stress Hormone: The Roles of FGF21 in Stress Adaptation and the Treatment of Metabolic Diseases," Diabetes & Metabolism Journal 38: 245-251.
Kliewer and Mangelsdorf,"Fibroblast growth factor 21: from pharmacology to physiology1-4," Am. J. Clin. Nutr. 91:254S-257S (2010).

(56) References Cited

OTHER PUBLICATIONS

Knight DM, et al., 1993,"Construction and Initial Characterization of a Mouse-Human Chimeric Anti-TNF Antibody," Molecular Immunology 30(16): 1443-1453.
Knutson et al., Biochem Pharmacol 53: 829 (1997).
Kobayashi N, et al., 1992, "Production and Specificity of Antisera Raised against 25-Hydroxyvitamin D3-[C-3]-Bovine Serum Albumin Conjugates," Steroids 57: 488-493.
Kobayashi N, et al., 1994, "Production of a Group-Specific Antibody to 1alpha,25-dihydroxyvitamin D and its Derivatives Having the 1alpha,3beta-dihydroxylated A-Ring Structure," Steroids 59: 404-411.
Kobayashi N, et al., 1994, "Specificity of the Polyclonal Antibodies Raised against a Novel 25-Hydroxyvitamin D3-Bovine Serum Albumin Conjugate Linked through the C11alpha Position," Journal of Steroid Biochemistry & Molecular Biology 48: 567-572.
Kohler et al, "Continuous cultures of fused cells secreting antibody of predefined specificity," Nature, 256: 495 (1975).
Kong J-H, et al., 2010, "Long-Acting Hyaluronate-Exendin 4 Conjugate for the Treatment of Type 2 Diabetes," Biomaterials 31: 4121-4128.
Kontermann R (editor), 2012, "Therapeutic Proteins: Strategies to Modulate Their Plasma Half-lives," Wiley-Blackwell, pp. 0-339.
SciFinder, Maleimide Side, Nov. 6, 2012.
SciFinder, Minimal Vitamin D side, Nov. 6, 2012.
SciFinder, Vitamin D side, Nov. 6, 2012.
Seifter, S. and Englard, S. (1990), "Analysis for Protein Modifications and Nonprotein Cofactors," Methods Enzymol 182: 626-646.
Sidhu et al., "Phage-displayed Antibody Libraries of Synthetic Heavy Chain Complementarity Determining Regions," J. Mol. Biol. 338(2): 299-310 (2004).
Slatopolsky et al., "A New Analog of Calcitriol, 19-Nor-1,25-(OH),D, , Suppresses Parathyroid Hormone Secretion in Uremic Rats in theAbsence of Hypercalcemia," Am J. Kidney Dis. 26: 852 (1995).
So et al., "A Novel Gemini Vitamin D Analog Represses the Expression of a Stem Cell Marker CD44 in Breast Cancer," Mol Pharmacol. 79(3):360-7 (2011).
Stamatov SD and Gronowitz S, 1990, "Glyceroamidothiophosphates of Cholecalciferol (Vitamin D3)," Lipids 25: 149-151.
Steddon et al. "Vitamin D analogues: how do they differ and what is their clinical role," Nephrol. Dial. Transplant. 16(10): 1965-1967 (2001).
Sun C, et al., 2013, "Bifunctional PEGylated Exenatide-Amylinomimetic Hybrids to Treat Metabolic Disorders: An Example of Long-Acting Dual Hormonal Therapeutics," Journal of Medicinal Chemistry 56: 9328-9341.
Swamy N, et al., 1995, "Affinity Purification of Human Plasma Vitamin D-Binding Protein," Protein Expression and Purification 6: 185-188.
Swamy N, et al., 1997, "Roles of Structure and Orientation of Ligands and Ligand Mimics inside the Ligand-Binding Pocket of the Vitamin D-Binding Protein," Biochemistry 36: 7432-7436.
Swamy N, et al., 2000, "Probing the Vitamin D Sterol Binding Pocket of Human Vitamin D Binding Protein with Bromoacetate Affinity Labeling Reagents Containing the Affinity Probe at C-3, C-6, C-11, and C-19 Positions of Parent Vitamin D Sterols," Archives of Biochemistry and Biophysics 373(2): 471-478.
Teegarden et. al.,"Determination of the Affinity of Vitamin D Metabolites to Serum Vitamin D Binding Protein Using AssayEmploying Lipid-Coated Polystyrene Beads," Anal. Biochemistry 199(2):293-299 (1991).
Touraine P, et al., 2009, "Lipoatrophy in GH Deficient Patients Treated with a Long-Acting PEGylated GH," European Journal of Endocrinology 161(4): 533-40.
Trussel S, et al., 2009, "New Strategy for the Extension of the Serum Half-Life of Antibody Fragments," Bioconjugate Chemistry 20: 2286-2292.
Vaswani and Hamilton, Ann. Allergy, Asthma & Immunol. 1:105-115 (1998).

Verboven C, et al., 2002, "A Structural Basis for the Unique Binding Features of the Human Vitamin D-Binding Protein," Nature Structural Biology 9: 131-6.
Vestergaard ET, et al., "Constant intravenous infusion in healthy men: clinical pharmacokinetics and metabolic effects," Am J Physiol Endocrinol Metab 292:E1829-E1836.
Vlahov IR, et al., 2006, "Design and Regioselective Synthesis of a New Generation of Targeted Chemotherapeutics. Part 1: EC145, a Folic Acid Conjugate of Desacetylvinblastine Monohydrazide," Bioorganic & Medicinal Chemistry Letters 16: 5093-5096.
Wang X-F, et al., 2007, "A Peptide Conjugate of Vitamin E Succinate Targets Breast Cancer Cells with High ErbB2 Expression," Cancer Research 67: 3337-3344.
Wootton AM, 2005, "Improving the Measurement of 25-Hydroxyvitamin D," Clinical Biochemist Reviews 26: 33-6.
Wu B and Sun Y-N, 2014, "Pharmacokinetics of Peptide-Fc Fusion Proteins," Journal of Pharmaceutical Sciences 103: 53-64.
Xu J et al., 2009. "Acute glucose-lowering and insulin-sensitizing action of FGF21 in insulin-resistant mouse models—association with liver and adipose tissue effects," Am J Physiol Endocrinol Metab 297: E1105-E1114.
Xu P., et al., 2014, Long-acting hypoglycemic effects of PEGylated FGF21 and insulin glargine in mice with type 1 diabetes, Journal of Diabetes and Its Complications, in press, http://dx.doi.org/10.1016/j.jdiacomp.2014.10.001.
Zeidler J, et al., 2012, "Biologic TNF inhibiting agents for treatment of inflammatory rheumatic diseases: dosing patterns and related costs in Switzerland from a payers perspective" Health Economics Review 2:20.
Zhang J, et al., 2010, "Identification of Two Distinct Cell Binding Sequences in the Vitamin D Binding Protein," Biochimica et Biophysica Acta 1803: 623-629.
Zhang Q, et al., 2010, "Synthesis of C-11 Linked Active Ester Derivatives of Vitamin D3 and Their Conjugations to 42-Residue Helix-Loop-Helix Peptides," Tetrahedron 66: 4577-4586.
Zhang, L. and Bulaj, G. (2012). "Converting Peptides into Drug Leads by Lipidation," Curr Med Chem 19: 1602-1618.
Zhao J, et al., 2013, "Targeted Co-delivery of Docetaxel and siPlk1 by Herceptin-conjugated Vitamin E TPGS Based-Immunomicelles," Biomaterials 34: 3411-3421.
Zhou K, et al., 2009, "Studies of Poly(ethylene glycol) Modification of HM-3 Polypeptides," Bioconjugate Chemistry 20: 932-936.
Gozes, "Potential clinical applications of vasoactive intestinal peptide: a selected update," Best Practice & Research Clinical Endocrinology & Metabolism vol. 18, No. 4, pp. 623-640, 2004.
Ray, Rahul et al. "Photoaffinity Labeling of the Rat Plasma Vitamin D Binding Protein with [26,27-3H]-25-Hydroxyvitamin D3 3B-[N-(4-Azido-2-nitrophenyl)glycinate]," Biochemistry, vol. 25, No. 17, 1986.
Roy, Aloka et al. "Aminopropylation of vitamin D hormone (1a,25-dihydroxyvitamin D3), its biological precursors, and other steroidal alcohols: An anchoring moiety for affinity studies of sterols," Steroids 60:530-533, 1995.
Norman, Anthony W. "From vitamin D to hormone D: fundamentals of the vitamin D endocrine system essential for good health," The American Journal of Clinical Nutrition, 88(suppl.), 491S-499S, 2008.
Hernandez-Martin, et al. "Synthesis of vitamin D3 analogues with A-ring modifications to directly measure vitamin D levels in biological samples," Bioorganic & Medicinal Chemistry 21, Oct. 2013.
PCT Search Report and Written Opinion for PCT application No. PCT/US2015/056737, dated Mar. 31, 2016.
PCT Search Report and Written Opinion for PCT application No. PCT/US2015/056723, dated Mar. 31, 2016.
PCT Invitation to Pay Additional Fees for PCT application No. PCT/US2015/056737, dated Feb. 3, 2016.
PCT Invitation to Pay Additional Fees for PCT application No. PCT/US2015/056723, dated Feb. 3, 2016.
Skander, Myriem, et al. "Chemical optimization of artificial metalloenzymes based on the biotin-avidin technology: (S)-selective and solvent-tolerant . . . " Chem. Commun., 2005.

(56) References Cited

OTHER PUBLICATIONS

Kostenuik et al. Infrequent Delivery of a Long-Acting PTH-Fc Fusion Protein Has Potent Anabolic Effects on Cortical and Cancellous Bone. Journal of Bone and Mineral Research. vol. 22, No. 10 (2007).
Vallinayagam, Ramakrishnan et al. "Novel Bioconjugates of Aminolevulinic Acid with Vitamins," Organic Letters, vol. 10, No. 20, 4453-4455, 2008.
El-Nachef et al. Microwave-Assisted Formation of Peptide-Vitamin Congugates. Eur. J. Org. Chem. 4412-2219. (2012).

* cited by examiner

Figure 2
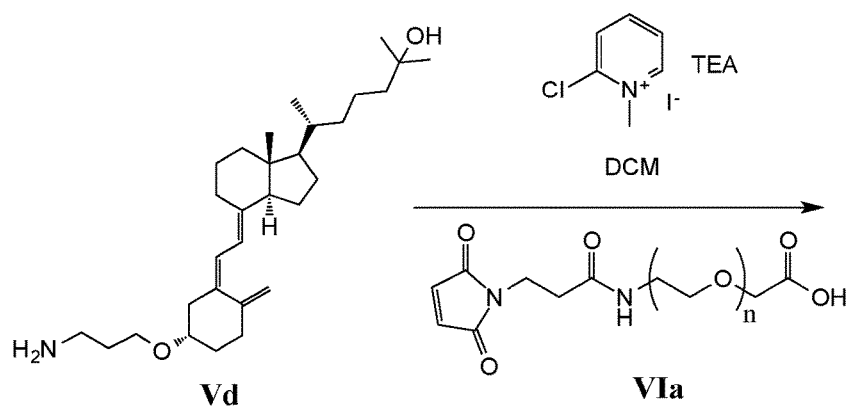
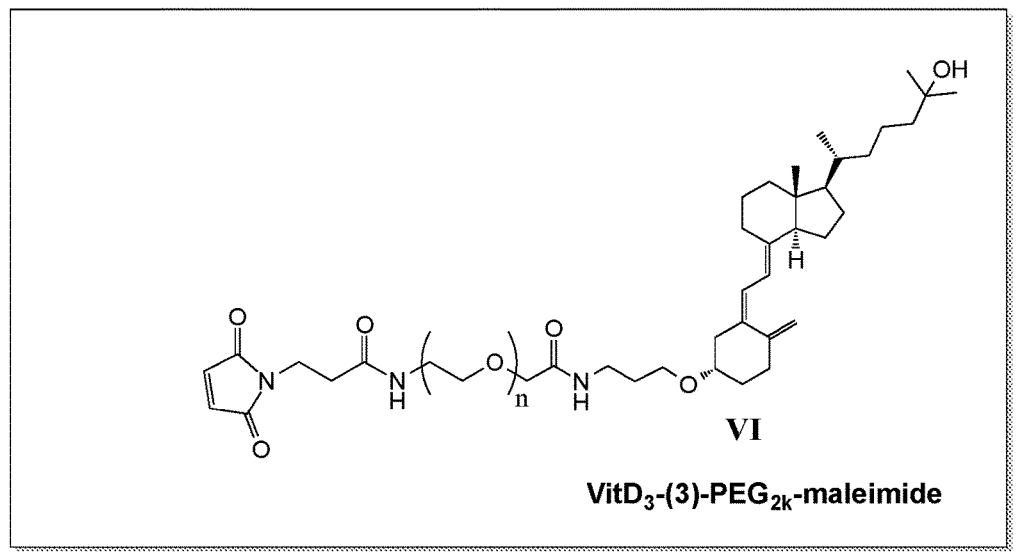

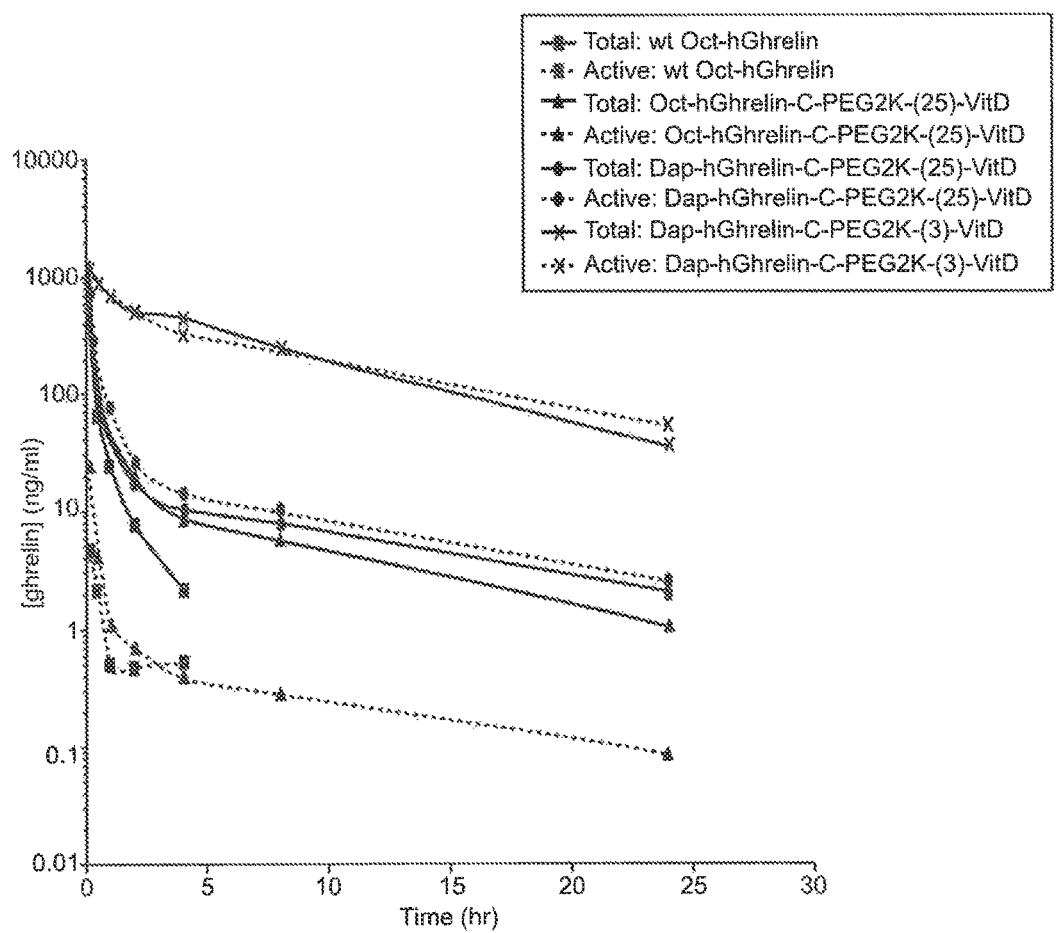

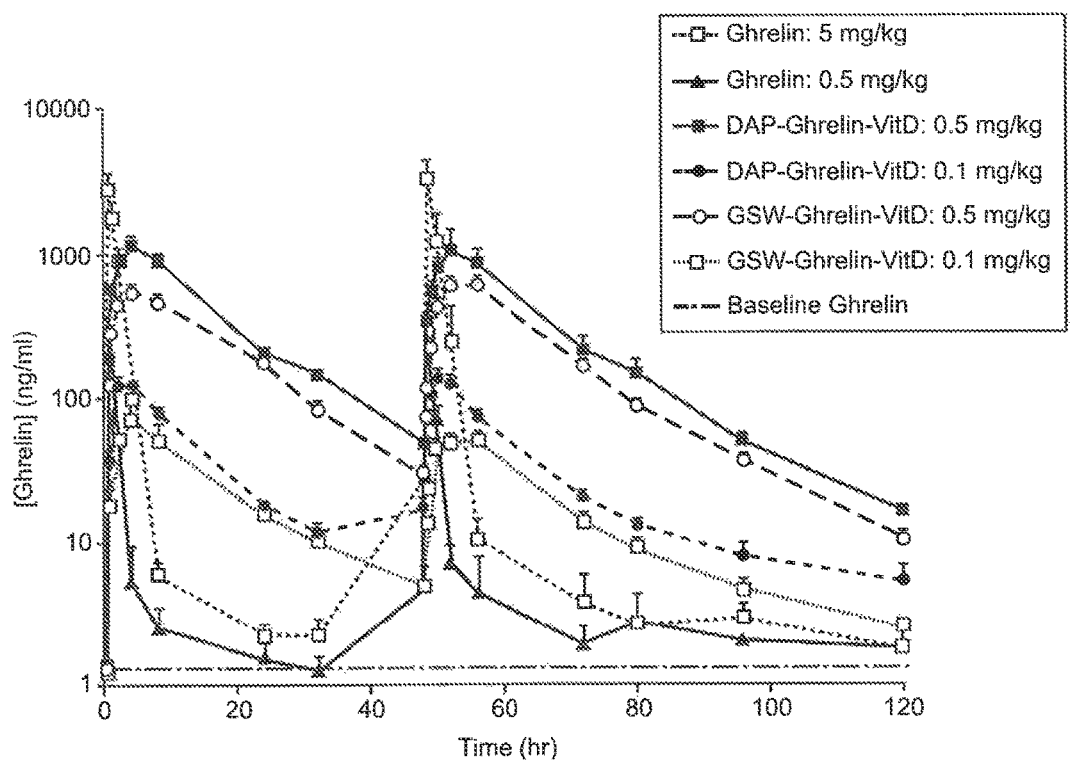

THERAPEUTIC VITAMIN D CONJUGATES

CROSS-REFERENCE TO RELATED APPLICATIONS

This application is a continuation of U.S. application Ser. No. 15/430,449 filed Feb. 11, 2017, which is a continuation of U.S. application Ser. No. 14/919,601 filed Oct. 21, 2015, issued as U.S. Pat. No. 9,585,934 on Mar. 7, 2017, which claims priority to U.S. Provisional Application No. 62/067,388 filed Oct. 22, 2014, and U.S. Provisional Application No. 62/244,181 filed Oct. 20, 2015, the contents of which are incorporated by reference herein in their entirety.

This invention was made with Government support under Grant No. IIP-1430894 awarded by the National Science Foundation, and Grant Nos. 1-R43-CA174094-01A1 and 1-R43-DK107231-01A1 awarded by the National Institutes of Health. The Government has certain rights in this invention.

SEQUENCE LISTING

The instant application contains a Sequence Listing which was submitted electronically in ASCII format in U.S. application Ser. No. 14/919,601 on Dec. 1, 2015, and is hereby incorporated by reference in its entirety. Said ASCII copy, created on Nov. 5, 2015, is named XTND005US1_SL.txt and is 17,869 bytes in size.

FIELD OF THE INVENTION

The invention provides non-hormonal vitamin D conjugated to therapeutic compounds that result in the compounds having increased absorption, bioavailability or circulating half-life when compared to non-conjugated forms. The vitamin D targeting groups are coupled to the therapeutic compounds via the third carbon on the vitamin D backbone.

BACKGROUND OF THE INVENTION

The invention relates to improving the potency, absorption or pharmacokinetic properties of therapeutic compounds to certain vitamin D forms. Vitamin D plays a role in calcium, phosphate, and bone homeostasis. The hormonal activity of vitamin D is mediated through binding to the vitamin D receptor (VDR). It enters the nucleus where it binds to the vitamin D receptor element (VDRE) present in the promoters of a subset of genes that are thus responsive to hormonal Vitamin D.

Vitamin D is a group of fat-soluble secosteroids. Several forms (vitamers) of vitamin D exist. The two major forms are vitamin D2 or ergocalciferol, and vitamin D3 or cholecalciferol. Vitamin D without a subscript refers to vitamin D2, D3 or other forms known in the art. In humans, vitamin D can be ingested as cholecalciferol (vitamin D3) or ergocalciferol (vitamin D2). The major source of vitamin D for most humans is sunlight. Once vitamin D is made in the skin or ingested, it needs to be activated by a series of hydroxylation steps, first to 25-hydroxyvitamin D (25(OH)D3) in the liver and then to 1,25-dihydroxyvitamin D3 (1α,25(OH)2D3) in the kidney. 1α,25(OH)2D3 is the active "hormonal" form of vitamin D because it binds to VDR. 25(OH)D3 is the "non-hormonal" form of vitamin D and is the major circulating form in the human body. It binds the vitamin D Binding Protein (DBP). It is only converted to the hormonal form as needed. An example of a non-hormonal vitamin D form is one that lacks a 1α-hydroxyl group. Non-hormonal vitamin D forms have a greatly reduced affinity for VDR and a greatly increased affinity for DBP.

DBP is the principal transporter of vitamin D metabolites. Its concentration in the plasma is 6-7 µM and has been detected in all fluid compartments. DBP concentrations exceed the physiological vitamin D metabolite concentrations. DBP is important for the translocation of vitamin D from the skin into circulation, and across cell membranes into the cytoplasm where vitamin D is activated into the hormonal form. The affinity of non-hormonal Vitamin D for DBP is significantly higher than the affinity of the hormonal form. In contrast, the affinity of the hormonal form to VDR is significantly than the non-hormonal form.

Vitamin D and vitamin D analogs have been approved for the treatment of osteoporosis and secondary hyperparathyroidism. Vitamin D has also been shown to inhibit proliferation and induce differentiation in normal as well as cancer cells. The level of vitamin D required for this activity causes severe toxicity in the form of hypercalcemia. Analogs of vitamin D have been approved for the treatment of psoriasis and others are currently being tested for cancer treatment. Many of the analogs discovered to have a reduced calcemic effect contain side-chain modifications. These modifications do not greatly affect VDR binding, and thus, in cell-based proliferation assays, show equal or even increased efficacy. It was shown, however, that many of these modifications reduce binding to DBP and thereby reduce the half-life in the bloodstream.

The addition of poly(ethylene glycol) or (PEG) is a known method of increasing the half-life of some compounds by reducing kidney clearance, reducing aggregation, and diminishing potentially unwanted immune recognition (Jain, Crit. Rev. Ther. Drug Carrier Syst. 25:403-447 (2008)). The PEG is typically used at a considerably large size (20-40 kDa) to maximize the half-life in circulation. This can be accomplished by using either a single large PEG or multiple smaller PEGs attached to the compound. (Clark et al. J. Biol. Chem. 271:21969-21977 (1996); Fishburn, J. Pharm. Sci. 97:4167-4183 (2008)).

Absorption is a primary focus in drug development and medicinal chemistry because a drug must be absorbed before any medicinal effects can take place. A drug's absorption profile can be affected by many factors. Additionally, the absorption properties of therapeutic compounds vary significantly from compound to compound. Some therapeutic compounds are poorly absorbed following oral or dermal administration. Other therapeutic compounds, such as most peptide- and protein-based therapeutics, cannot be administered orally. Alternate routes of administration such as intravenous, subcutaneous, or intramuscular injections are routinely used for some of these compounds; however, these routes often result in slow absorption and exposure of the therapeutic compounds to enzymes that can degrade them, thus requiring much higher doses to achieve efficacy.

A number of peptides have been identified as therapeutically promising. The chemical and biological properties of peptides and proteins make them attractive candidates for use as therapeutic compounds. Peptides and proteins are naturally-occurring molecules made up of amino acids and are involved in numerous physiological processes. Peptides and proteins display a high degree of selectivity and potency, and may not suffer from potential adverse drug-drug interactions or other negative side effects. Thus peptides and proteins hold great promise as a highly diverse, highly potent, and highly selective class of therapeutic compounds with low toxicity. Peptides and proteins, however, may have short in vivo half-lives. For such peptides, this may be a few minutes. This may render them generally impractical, in their native form (also referred to as "wild", "wild type" or "wt" herein), for therapeutic administration. Additionally, peptides may have a short duration of action or poor bioavailability.

Apelin peptide (SEQ ID NO:1) is encoded by the APLN gene. The apelin gene encodes a pre-proprotein of 77 amino acids with a signal peptide in the N-terminal region. After translocation into the endoplasmic reticulum and cleavage of the signal peptide, the proprotein of 55 amino acids may generate several active fragments: a 36 amino acid peptide corresponding to the sequence 42-77 (apelin 36), a 17 amino acid peptide corresponding to the sequence 61-77 (apelin 17) and a 13 amino acid peptide corresponding to the sequence 65-77 (apelin 13). This latter fragment may also undergo a pyroglutamylation at its N-terminal glutamine residue.

Apelin is the endogenous ligand for the G-protein-coupled APJ receptor that is expressed at the surface of some cell types. It is widely expressed in various organs such as the heart, lung, kidney, liver, adipose tissue, gastrointestinal tract, brain, adrenal glands, endothelium, and human plasma.

The apelin receptor participates in the control of blood pressure and the formation of new blood vessels (angiogenesis). Apelin causes hypotension from the activation of its receptors on the surface of endothelial cells. This induces the release of NO, a potent vasodilator, which induces relaxation of the smooth muscle cells of artery wall. The angiogenic activity results from Apelin promoting the proliferation and migration of endothelial cells and the formation of new blood vessels. Other effects of apelin include regulation of fluid homeostasis, hypothalamic regulation of food and water intake, pituitary hormone release, and down-regulation of the antidiuretic hormone vasopressin in the brain. Additionally, apelin is secreted in the gastrointestinal tract and in the pancreas.

Apelin regulates cardiovascular and fluid homeostasis, food intake, cell proliferation, and angiogenesis. Apelin is also considered to be an adipokine that is linked to metabolic disorders such as obesity and type 2 diabetes. Apelin therapies may thus be a beneficial treatment for these conditions. See, e.g., Castan-Laurell, et al., *Endocrine* 40(1):1-9 (2011). Indeed, Apelin inhibits insulin secretion induced by glucose. Likewise, insulin stimulates apelin, revealing a feedback loop for insulin production. The in vivo half-life of apelin, however, is 20 minutes or less. See, e.g., Bertrand et al. *Front Physiol.* 6:115 (2015).

Ghrelin is a mammalian peptide (SEQ ID NO:2) that is naturally secreted from the stomach into circulation to stimulate appetite and release of growth hormone (GH). Ghrelin stimulates the release of growth hormone from the pituitary gland through the cellular receptor GHS-R and plays an important role in energy homeostasis. In addition, ghrelin acts directly on the central nervous system to decrease sympathetic nerve activity. GHS-Rs are concentrated in the hypothalamus-pituitary unit. GHS-R is distributed in peripheral tissues, including the heart, lung, liver, kidney, pancreas, stomach, small and large intestines, adipose, and immune cells.

Ghrelin has been used therapeutically to increase weight and lean body mass in patients suffering from cachexia or involuntary weight loss resulting from chronic diseases such as cancer (Hiura et. al., *Cancer,* 118:4785-94 (2012)). Ghrelin, however, has a naturally short half-life of 11 minutes in humans (Akamizu et al., *Eur J Endocrinol* 150:447-55 (2004)) and thus must be dosed often to see therapeutic effects.

Parathyroid hormone (PTH), parathormone or parathyrin, is secreted by the chief cells of the parathyroid glands. It is a polypeptide containing 84 amino acids (SEQ ID NO:10). It acts to increase the concentration of calcium ($Ca^{2+}$) in the blood (in contrast to calcitonin which decreases calcium concentration). PTH activates the parathyroid hormone 1 receptor (bone and kidney) and the parathyroid hormone 2 receptor (central nervous system, pancreas, testis, and placenta). PTH, however, has a very short half-life of approximately 4 minutes.

Hypoparathyroidism is a low level of PTH in the blood that is most commonly due to damage to or removal of parathyroid glands during thyroid surgery, immune system-related damage, inheritance, or other rare causes. It can lead to low levels of calcium in the blood, often causing cramping and twitching of muscles or tetany (involuntary muscle contraction), and several other symptoms. Calcium replacement or vitamin D can ameliorate the symptoms but can increase the risk of kidney stones and chronic kidney disease. See, e.g. Winer K K, et. al. *J. Clin. Endocrinol. Metab.* 97(2): 391-399 (2012).

Insulin is a peptide hormone produced by beta cells in the pancreas that regulates the metabolism of carbohydrates and fats (SEQ ID NO:11 and 12). The human insulin protein is composed of 51 amino acids, and has a molecular weight of 5808 Daltons. It is a dimer of an A-chain and a B-chain that are linked by disulfide bonds. It promotes the absorption of glucose from the blood to skeletal muscles and fat tissue and causes fat to be stored rather than used for energy.

Under normal physiological conditions, insulin is produced at a constant proportion to remove excess glucose from the blood. When control of insulin levels fails, however, diabetes mellitus can result. Thus, diabetic patients often receive injected insulin. Patients with type 1 diabetes depend on external insulin for their survival because the hormone is no longer sufficiently produced internally. Insulin is most commonly injected subcutaneously. Patients with type 2 diabetes are often insulin resistant and may suffer from an "apparent" insulin deficiency.

Fibroblast Growth Factor 21 (SEQ ID:2) is a protein that circulates in serum. Encoded by the FGF21 gene, it is a member of a family of atypical fibroblast growth factors (FGFs) that includes FGF19 and FGF23. It lacks the conventional FGF heparin-binding domain. FGF family members possess broad mitogenic and cell survival activities and are involved in a variety of biological processes including embryonic development, cell growth, morphogenesis, tissue repair, tumor growth and invasion. FGF21 is specifically induced by HMGCS2 activity. FGF21 stimulates glucose uptake in adipocytes but not in other cell types. This effect is additive to the activity of insulin.

FGF21 prefers binding to the FGFR1c/b-Klotho receptor complex over those containing other FGFR isotypes (Kliewer and Mangelsdorf, *Am. J. Clin. Nutr.* 91:254S-257S (2010)). Administration of FGF21 to diabetic animals reduces circulating glucose levels while excess FGF21 does not induce hypoglycemia as seen with administration of excess insulin (Kharitonenkov and Shanafelt, *Curr. Opin. Investig. Drugs* 10:359-364 (2009)). Therefore, FGF21 is a promising therapeutic protein for the treatment of diabetes. FGF21 in its natural state, however, has an extremely short half-life in serum (about 1.1 hours) making it a clinically impractical treatment (see, e.g. WO03/011213; Kharitonenkov et al., *J. Clin. Invest.* 115:1627-1635 (2005)). Additionally, FGF21 exhibits poor bioavailability when injected subcutaneously (Xu J et al., 2009. *Am J Physiol. Endocrinol. Metab.* 297: E1105-E1114).

Infliximab (Remicade®, Janssen Biotech Inc., U.S. Pat. No. 5,919,452 and US 2002/0141996, incorporated herein by reference in their entirety) is a monoclonal antibody that binds tumor necrosis factor alpha (TNF-α, SEQ ID NO:13) that is used to treat autoimmune diseases. Infliximab was approved by the U.S. Food and Drug Administration (FDA) for the treatment of psoriasis, Crohn's disease, ankylosing spondylitis, psoriatic arthritis, rheumatoid arthritis, and ulcerative colitis. TNF-α is a chemical messenger (cytokine) and a key part of the autoimmune reaction. Infliximab is administered intravenously by a healthcare professional and is not approved for subcutaneous dosing.

RNA interference (RNAi) is a process where RNA molecules inhibit gene expression often by causing specific mRNA molecules to degrade. Two types of RNA molecules—microRNA (miRNA) and small interfering RNA (siRNA)—are central to RNA interference. They bind to the target mRNA molecules and either increase or decrease their activity. RNAi helps cells defend against parasitic nucleic acids such as those from viruses and transposons. RNAi also influences development.

Initial medical applications for RNAi involve genetic diseases such as macular degeneration and Huntington's disease. Additional applications may include certain cancers, respiratory syncytial virus, herpes simplex virus type 2, HIV, hepatitis A and B, influenza, and measles.

It remains difficult to deliver RNAi to target tissues, and in particular, tissues deep within the body. siRNA molecules have a short in vivo half-life due to endogenous nucleases. Also, targeting specific tissues is challenging. One approach has been high dosage levels of siRNA to ensure the tissues have been reached. With these approaches, however, hepatotoxicity was reported.

Therapeutic oligonucleotides, while promising, suffer from a short plasma half-life as well as from problems with delivery and cellular uptake. Conjugation of oligonucleotides to small molecules has been proposed to overcome these problems but have not yet been successful.

SUMMARY OF THE INVENTION

The invention provides carrier-drug conjugates comprising a targeting group that is non-hormonal vitamin D, an analog, or metabolite thereof linked at the carbon 3 position to a therapeutic compound. In some embodiments, the non-hormonal vitamin D molecules are not hydroxylated at the carbon 1 position. The carriers enhance the absorption, stability, half-life, duration of effect, potency, or bioavailability of the therapeutic compounds. Optionally, the carriers further comprise scaffolding moieties that are non-releasable such as PEG and others described in this disclosure.

Thus, the invention provides a carrier-drug conjugate comprising a targeting group that is a non-hormonal vitamin D, analog, or metabolite thereof conjugated to a therapeutic compound at the carbon 3 position of said non-hormonal vitamin D targeting group. In some embodiments, the non-hormonal vitamin D is not hydroxylated at the carbon 1 position. In preferred embodiments, the targeting group is conjugated to the therapeutic compound via a scaffold that is between about 100 and 200,000 Da and is selected from the group consisting of poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, and an additional therapeutic compound.

In another embodiment, the invention provides a pharmaceutical composition comprising a carrier-drug conjugate comprising a targeting group that is a non-hormonal vitamin D, analog, or metabolite thereof conjugated to a therapeutic compound at the carbon 3 position of the non-hormonal vitamin D targeting group via a scaffold. In a preferred embodiment, the carrier increases the absorption, bioavailability, or half-life of said therapeutic compound in circulation. In another preferred embodiment, the non-hormonal vitamin D is not hydroxylated at the carbon 1 position. In another preferred embodiment of the pharmaceutical composition, the scaffold is selected from the group consisting of poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, and an additional therapeutic compound.

In another preferred embodiment, the therapeutic compound is selected from the group consisting of small molecules, chemical entities, nucleic acids, nucleic acid derivatives, peptides, peptide derivatives, naturally-occurring proteins, non-naturally-occurring proteins, peptide-nucleic acids (PNA), stapled peptides, morpholinos, phosphorodiamidate morpholinos, oligonucleotides, antisense drugs, RNA-based silencing drugs, aptamers, glycoproteins, enzymes, hormones, cytokines, interferons, growth factors, blood coagulation factors, antibodies, antibody fragments, antibody derivatives, toxin-conjugated antibodies, antibody-drug conjugates, metabolic effectors, analgesics, antipyretics, anti-inflammatory agents, antibiotics, anti-microbial agents, anti-viral agents, anti-fungal drugs, musculoskeletal drugs, cardiovascular drugs, renal drugs, pulmonary drugs, digestive disease drugs, hematologic drugs, urologic drugs, metabolism drugs, hepatic drugs, neurological drugs, anti-diabetes drugs, anti-cancer drugs, drugs for treating stomach conditions, drugs for treating colon conditions, drugs for treating skin conditions, and drugs for treating lymphatic conditions.

In a more preferred embodiment, the therapeutic compound is a protein having apelin activity comprising an amino acid sequence with at least a 90% sequence identity to SEQ ID NO:1 or 16. In another more preferred embodiment, the targeting group is vitamin D that is not hydroxylated at the carbon 1 position. In another more preferred embodiment, the scaffold is poly(ethylene glycol).

The invention provides that the therapeutic compound may be a protein having ghrelin activity comprising an amino acid sequence with at least a 90% sequence identity to a protein selected from the group consisting of SEQ ID NO:2, 3, 4, and 5. In a more preferred embodiment, the targeting group is vitamin D that is not hydroxylated at the carbon 1 position. In other more preferred embodiments, the therapeutic compound is a protein comprising the amino acid sequence of SEQ ID NO:2, 3, 4, or 5. In another more preferred embodiment, the scaffold is poly(ethylene glycol).

The invention provides a pharmaceutical composition comprising a protein having PTH activity that has an amino acid sequence with at least a 90% sequence identity to SEQ ID NO:10 or 17. In a preferred embodiment, the targeting group is vitamin D that is not hydroxylated at the carbon 1 position. In another preferred embodiment, the scaffold is poly(ethylene glycol).

The invention provides a pharmaceutical composition comprising a protein having insulin activity and comprising a peptide having amino acid an sequences with at least a 90% sequence identity to SEQ ID NO:11 or 12. In a preferred embodiment, the targeting group is vitamin D that is not hydroxylated at the carbon 1 position. In another preferred embodiment, the scaffold is poly(ethylene glycol).

In one embodiment of the invention, the therapeutic compound is an antibody. In a preferred embodiment, the antibody binds with high affinity to a protein having at least a 90% sequence identity to SEQ ID NO:13. In another preferred embodiment, the targeting group is vitamin D that is not hydroxylated at the carbon 1 position. In another preferred embodiment, the scaffold is poly(ethylene glycol).

The invention contemplates that the therapeutic compound is an RNA molecule. In a preferred embodiment, the targeting group is vitamin D that is not hydroxylated at the carbon 1 position. In another preferred embodiment, the scaffold is poly(ethylene glycol).

The invention provides a method of treating a patient in need of a therapeutic compound, comprising administering an effective amount of the pharmaceutical compositions described herein. In some embodiments, the therapeutic compound is selected from the group consisting of small molecules, chemical entities, nucleic acids, nucleic acid derivatives, peptides, peptide derivatives, naturally-occurring proteins, non-naturally-occurring proteins, peptide-nucleic acids (PNA), stapled peptides, morpholinos, oligonucleotides, morpholinos, antisense drugs, RNA-based silencing drugs, aptamers, glycoproteins, enzymes, hormones, cytokines, interferons, growth factors, blood coagulation factors, antibodies, antibody fragments, antibody derivatives, toxin-conjugated antibodies, antibody-drug conjugates, metabolic effectors, analgesics, antipyretics, anti-inflammatory agents, antibiotics, anti-microbial agents, anti-viral agents, anti-fungal drugs, musculoskeletal drugs, cardiovascular drugs, renal drugs, pulmonary drugs, digestive disease drugs, hematologic drugs, urologic drugs, metabolism drugs, hepatic drugs, neurological drugs, anti-diabetes drugs, anti-cancer drugs, drugs for treating stomach conditions, drugs for treating colon conditions, drugs for treating skin conditions, and drugs for treating lymphatic conditions.

In one embodiment of the method, therapeutic compound is a protein having apelin activity comprising an amino acid sequence with at least a 90% sequence identity to SEQ ID NO:1 or 15. In a preferred embodiment, the targeting group is vitamin D that is not hydroxylated at the carbon 1 position. In another preferred embodiment, the scaffold is poly(ethylene glycol).

In another embodiment of the method, the therapeutic compound is a protein having ghrelin activity comprising an amino acid sequence with at least a 90% sequence identity to a protein selected from the group consisting of SEQ ID NO:2, 3, 4, and 5. In a preferred embodiment, the targeting group is vitamin D that is not hydroxylated at the carbon 1 position. In other preferred embodiments, the therapeutic compound is a protein comprising the amino acid sequence of SEQ ID NO:2, 3, 4, or 5. In another preferred embodiment, the scaffold is poly(ethylene glycol).

In another embodiment of the method, the therapeutic compound is a protein having PTH activity comprising an amino acid sequence with at least a 90% sequence identity to SEQ ID NO:10 or 16. In a preferred embodiment, the targeting group is vitamin D that is not hydroxylated at the carbon 1 position. In another preferred embodiment, the scaffold is poly(ethylene glycol).

In another embodiment of the method, the therapeutic compound is a protein having insulin activity comprising an amino acid sequence with at least a 90% sequence identity to SEQ ID NO:11 or at least a 90% sequence identity to SEQ ID NO:12. In a preferred embodiment, the targeting group is vitamin D that is not hydroxylated at the carbon 1 position. In another preferred embodiment, the scaffold is poly(ethylene glycol).

In another embodiment of the method, the therapeutic compound is an antibody. In a preferred embodiment, the antibody binds with high affinity to a protein having at least a 90% sequence identity to SEQ ID NO:13. In another preferred embodiment, the targeting group is vitamin D that is not hydroxylated at the carbon 1 position. In another preferred embodiment, the scaffold is poly(ethylene glycol).

In another embodiment of the method, the therapeutic compound is an RNA molecule. In a preferred embodiment, the targeting group is vitamin D that is not hydroxylated at the carbon 1 position. In another preferred embodiment, the scaffold is poly(ethylene glycol).

The methods of the invention provide that the pharmaceutical compositions are delivered to patients by a transdermal, oral, parenteral, subcutaneous, intracutaneous, intravenous, intramuscular, intraarticular, intrasynovial, intrasternal, intrathecal, intralesional, intracranial injection, infusion, inhalation, ocular, topical, rectal, nasal, buccal, sublingual, vaginal, or implanted reservoir mode.

The invention provides pharmaceutical compositions for the manufacture of a medicament for the treatment of a patient in need of said medicament.

The invention provides a method of manufacturing the pharmaceutical composition disclosed herein, comprising conjugating the targeting group and the therapeutic compound, wherein the conjugating step utilizes a coupling group. In preferred embodiments, the coupling group is selected from the group consisting of an amine-reactive group, a thiol-reactive group, a maleimide group, a thiol group, an aldehyde group, an NETS-ester group, a haloacetyl group, an iodoacetyl group, a bromoacetyl groups, a SMCC group, a sulfo SMCC group, a carbodiimide group, bifunctional cross-linkers, NHS-maleimido, and combinations thereof. Thus, the invention provides pharmaceutical compositions resulting from the methods, wherein the composition comprises a carrier-drug compound containing a linkage selected from the group consisting of a thiol linkage, an amide linkage, an oxime linkage, a hydrazone linkage, and a thiazolidinone linkage. In another embodiment, the conjugating step is accomplished by cycloaddition reactions.

The invention provides a pharmaceutical carrier comprising a formula I:

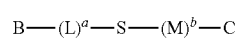

$$B-(L)^a-S-(M)^b-C \qquad I$$

Wherein:
B is a targeting group that is a non-hormonal vitamin D, analog, or metabolite thereof conjugated at the carbon 3 position to $L^1$;
S is a scaffold moiety, comprising poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, polylactic acid, a water-soluble polymer, a small carbon chain linker, or an additional therapeutic moiety;
C is an amine-reactive group, a thiol-reactive group, a maleimide group, a thiol group, a disulfide group, an aldehyde group, an NETS-ester group, a 4-nitrophenyl ester, an acylimidazole, a haloacetyl group, an iodoacetyl group, a bromoacetyl groups, a SMCC group, a sulfo SMCC group, a carbodiimide group and bifunctional cross-linkers such as NHS-maleimido or combinations thereof;

(L)$^a$ and (M)$^b$ are linkers independently selected from —(CH$_2$)$_n$, —C(O)NH—, —HNC(O)—, —C(O)O—, —OC(O)—, —O—, —S—S—, —S—, —S(O)—, —S(O)$_2$— and —NH—;

a is an integer from 0-4; and b is an integer from 0-4; and n is an integer from 0-3.

The invention provides a pharmaceutical carrier comprising formula V:

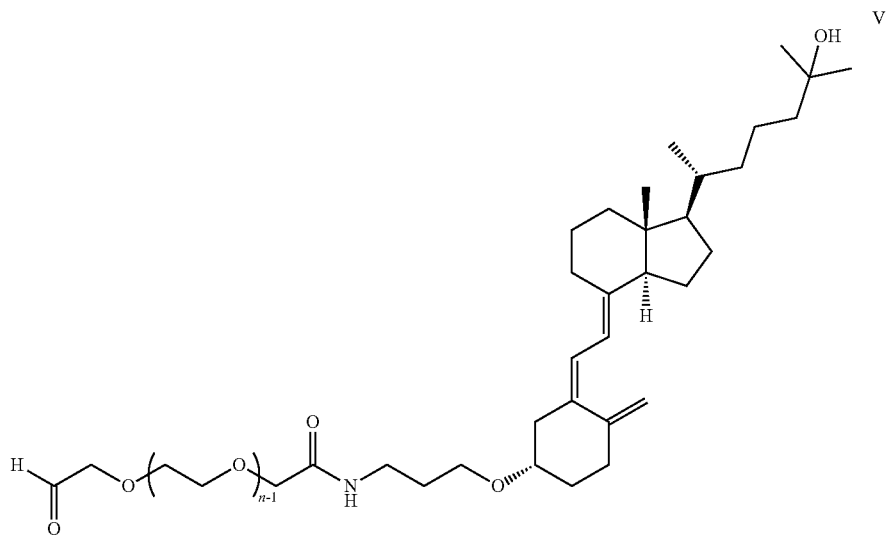

The invention provides a pharmaceutical carrier comprising formula VI:

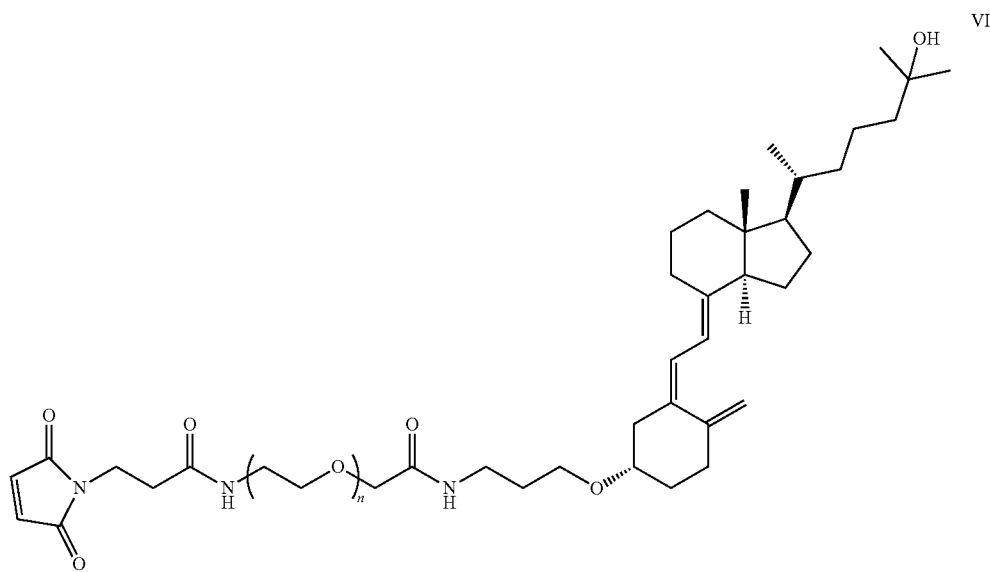

The invention provides a pharmaceutical carrier comprising formula VII:

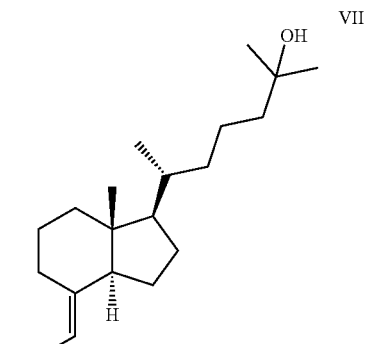
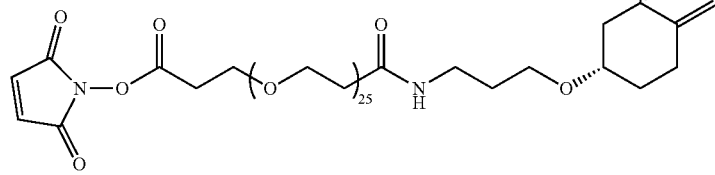

The invention provides a pharmaceutical composition, comprising a therapeutic compound, a stably attached scaffold, a targeting group that is a non-hormonal vitamin D, analog, or metabolite thereof conjugated at the carbon 3 position, wherein after administration to a first test subject, the therapeutic compound has a half life measured by ELISA analysis of blood samples taken at a plurality of time points that is greater than a half life of the therapeutic compound administered to a second test subject without the stably attached scaffold moiety and targeting group as measured by ELISA analysis of blood samples taken at the plurality of time points. In a preferred embodiment, the administration to the first and second subjects is accomplished by subcutaneous injection. In another preferred embodiment, the therapeutic compound stably attached to the scaffold and targeting group retains substantially the same activity as the therapeutic compound not stably attached to the scaffold and targeting group as measured by a functional assay.

In another preferred embodiment of the pharmaceutical composition, a scaffold mass range is selected from the group consisting of 100 Da. to 20,000 Da., 200 Da. to 15,000 Da., 300 Da. to 10,000 Da., 400 Da. to 9,000 Da., 500 Da. to 5,000 Da., 600 Da. to 2,000 Da., 1000 Da. to 200,000 Da., 20.00 Da. to 200,000 Da., 100,000 to 200,000 Da., 5000 Da. to 100,000 Da., 10,000 Da. to 80,000 Da., 20,000 Da. to 60,000 Da., and 20,000 Da. to 40,000 Da. In a more preferred embodiment, the scaffold is approximately the same mass as the therapeutic compound.

The invention provides a carrier-drug conjugate comprising a targeting group that is vitamin D, an analog, or a metabolite thereof that is non-releasably conjugated to a therapeutic compound. In a preferred embodiment, the vitamin D is non-hormonal. In a more preferred embodiment, the non-hormonal vitamin D is not hydroxylated at the carbon 1 position. In a preferred embodiment, the therapeutic compound is conjugated at the carbon 3 position of the non-hormonal vitamin D targeting group. In a more preferred embodiment, the therapeutic compound retains substantially the same activity as the therapeutic compound not conjugated to the targeting group as measured by a functional assay. In a more preferred embodiment, the targeting group is conjugated to the therapeutic peptide or said therapeutic nucleic acid via a scaffold that is selected from the group consisting of poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, and an additional therapeutic compound. In a more preferred embodiment, the scaffold is approximately the same mass as the therapeutic compound.

BRIEF DESCRIPTION OF THE DRAWINGS

FIG. 2: Reaction scheme showing the chemical structure and syntheses used to generate a carrier, a Vitamin D-(3)-PEG$_{2K}$-maleimide adduct. The carrier was generated by conjugating 1) a vitamin D analog, 2) a PEG scaffold, and 3) a maleimide coupling group.

FIG. 6A: Improved pharmacokinetics of ghrelin conjugated to the Vitamin D-(25)-PEG$_{2k}$-maleimide carrier and the Vitamin D-(3)-PEG$_{2k}$-maleimide carrier when compared to unmodified ghrelin. Total (solid lines) and active (dashed lines) ghrelin were compared following intravenous injection into Sprague Dawley rats. FIG. 6B: Ghrelin conjugated to the Vitamin D-(3)-PEG$_{2k}$-maleimide carrier was compared to unmodified ghrelin in rats following subcutaneous injections at t=0 and 48 hours and at various doses.

DETAILED DESCRIPTION OF THE INVENTION

Figure 1:
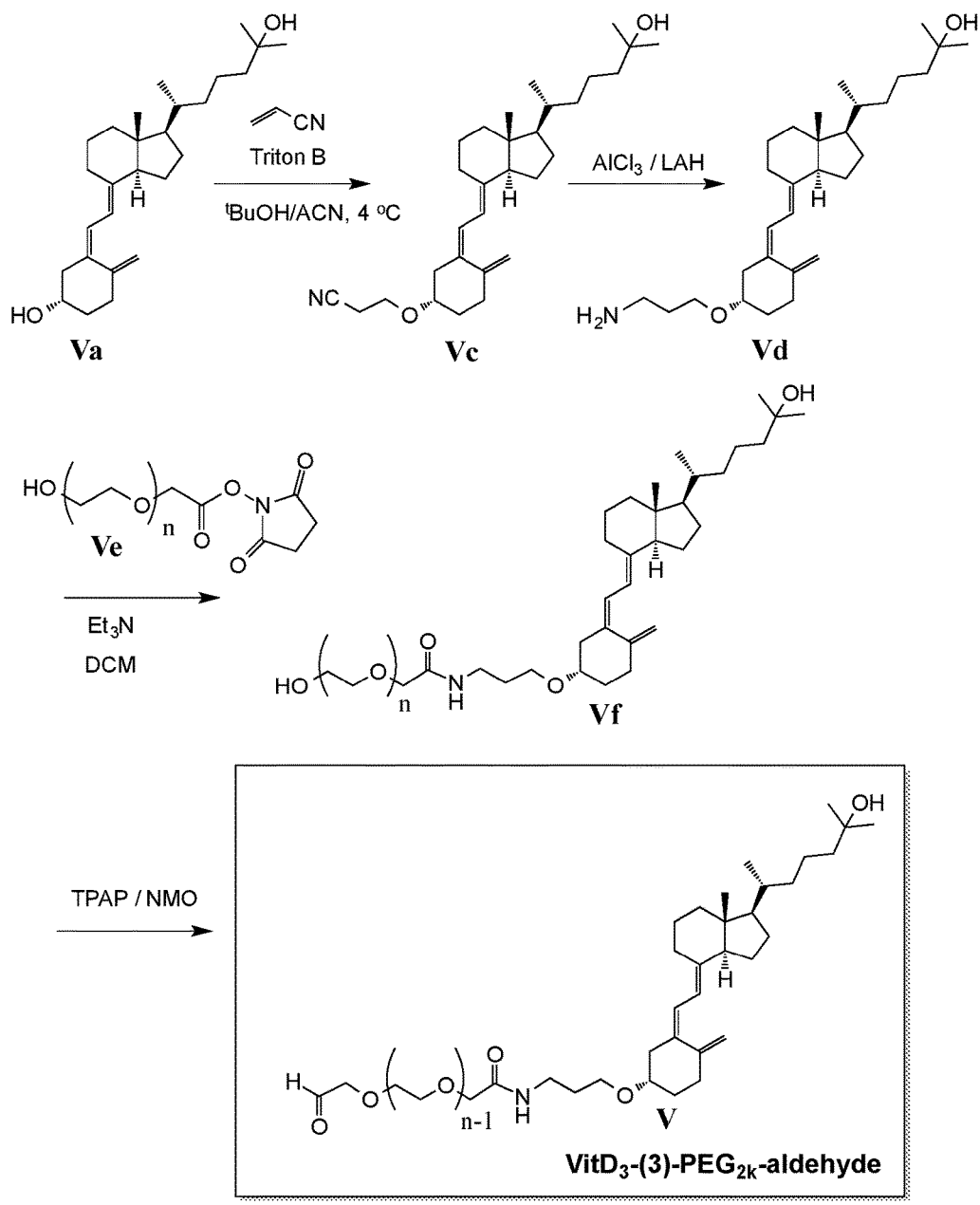
FIG. 1: Reaction scheme showing the chemical structure and syntheses used to generate a carrier, a Vitamin D-(3)-PEG$_{2K}$-aldehyde adduct. The carrier was generated by conjugating 1) a vitamin D analog, 2) a PEG scaffold, and 3) an aldehyde coupling group.

The invention provides carrier-drug conjugates comprising targeting groups that are non-hormonal vitamin D, vitamin D analogs, or vitamin D metabolites. Examples include vitamin D-based molecules that are not hydroxylated at the carbon 1 (C1) position. The carriers are linked to therapeutic compounds at the carbon 3 (C3) position. As disclosed herein, carrier groups are surprisingly effective when non-hormonal vitamin D forms are used and the therapeutic compound is linked to the Carbon 3 position. While not wishing to be bound by theory, it is believed that the hormonal forms of vitamin D are not appropriate for the carriers described herein because they can be toxic due to the induction of hypercalcemia. Also, because the hormonal forms bind the vitamin D receptor in cells, they may improperly target the carrier-drug conjugates to undesired cells or tissues. In contrast, non-hormonal vitamin D forms bind the Vitamin D Binding Protein (DBP) and remain in circulation longer.

The carrier molecules are attached to the therapeutic compounds using chemistries described herein, described in WO2013172967, incorporated herein in its entirety, or that are otherwise known in the art. The carriers improve the potency, absorption, bioavailability, circulating half-life or pharmacokinetic properties of the therapeutic compounds. In certain embodiments, the carriers further comprise what will be described herein as a "scaffold" that acts, among other things, as a non-releasable "spacer" between the targeting group and the therapeutic compound. In other embodiments, the carriers lack a scaffold.

The carriers are designed to be suitable for use in humans and animals. The carriers serve the purpose of improving the pharmacokinetic properties of a biological or chemical entity that is coupled, conjugated, or fused to the carrier. This occurs through the interaction of the targeting group with DBP. DBP can actively transport molecules quickly and effectively from the site of administration to the circulating plasma, thereby reducing exposure of the drug to degradative enzymes. The carriers, by binding to DBP, also improve the circulating half-life of the drug. This increases the potency and therapeutic efficacy of the drug by preventing kidney filtration and other elimination processes.

The impact on patient health of this new class of therapies will be profound. Many previously unusable therapies for serious conditions such as ghrelin for cancer cachexia, apelin for pulmonary arterial hypertension, diabetes, and cardiac disease, and PTH for hypoparathyroidism could be realized by application of this invention. Improvements in other current therapies such as insulin and GLP1 for treating diabetes could have a big impact on patient health and convenience. A large number of diseases may benefit from RNAi-based treatments. These include diseases such as macular degeneration and Huntington's disease. Additionally, certain cancers, liver diseases, and infectious diseases including respiratory syncytial virus, herpes simplex virus type 2, HIV, hepatitis A and B, influenza, and measles may benefit from RNAi-based treatments.

In describing and claiming one or more embodiments of the present invention, the following terminology will be used in accordance with the definitions described below.

The term "absorption" is the movement of a drug into the bloodstream. A drug needs to be introduced via some route of administration (e.g. oral, topical or dermal, subcutaneous, intramuscular, or intravenous) or in a specific dosage form such as a tablet, patch, capsule or liquid.

An "antagonist" refers to a molecule capable of neutralizing, blocking, inhibiting, abrogating, reducing or interfering with the activities of a particular or specified protein, including its binding to one or more receptors in the case of a ligand, or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of proteins, hormones, or other bioactive molecules. Antagonists may be fusion proteins, receptor molecules, antisense molecules, aptamers, ribozymes, or derivatives that bind specifically to the proteins, hormones, or other bioactive molecules and thereby sequester its binding to its target.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules that generally lack antigen specificity. Polypeptides of the latter kind are, for example, produced at low levels by the lymph system and at increased levels by myelomas.

"Aptamers" are nucleic acid-based compounds that have been selected to bind a specific target. An example of an aptamer-based therapeutic compound can be found in WO07/035922, incorporated by reference herein in its entirety.

The term "bioavailability" refers to the fraction of an administered dose of unchanged drug that reaches the systemic circulation, one of the principal pharmacokinetic properties of drugs. When a medication is administered intravenously, its bioavailability is 100%. When a medication is administered via other routes (such as orally), its bioavailability generally decreases (due to incomplete absorption and first-pass metabolism) or may vary from patient to patient. Bioavailability is an important parameter in pharmacokinetics that is considered when calculating dosages for non-intravenous routes of administration.

"Carriers" are compounds that can be conjugated to, fused to, coupled to or formulated with therapeutic compounds to improve the absorption, half-life, bioavailability, pharmacokinetic or pharmacodynamic properties of the drugs. They comprise a targeting group, a coupling group, and optionally, a scaffold moiety. In some embodiments, carriers may carry a therapeutic compound from the site of subcutaneous injection into circulation as well as carry the therapeutic compound in circulation for an extended period of time.

An "effective amount" refers to an amount of therapeutic compound that is effective, at dosages and for periods of time necessary, to achieve the desired therapeutic or prophylactic result. A "therapeutically effective amount" of a therapeutic compound may vary according to factors such as the disease state, age, sex, and weight of the individual. A therapeutically effective amount may be measured, for example, by improved survival rate, more rapid recovery, or amelioration, improvement or elimination of symptoms, or other acceptable biomarkers or surrogate markers. A therapeutically effective amount is also one in which any toxic or detrimental effects of the therapeutic compound are outweighed by the therapeutically beneficial effects. A "prophylactically effective amount" refers to an amount of therapeutic compound that is effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

"Half-life" is a scientific term known in the art that refers to the amount of time that elapses when half of the quantity of a test molecule is no longer detected. An in vivo half-life refers to the time elapsed when half of the test molecule is no longer detectable in circulating serum or tissues of a human or animal.

A "hormone" is a biological or chemical messenger that communicates between one cell (or group of cells) to another cell. As described herein, hormones for use in the invention may be peptides, steroids, pheromones, interleukins, lymphokines, cytokines, or members of other hormone classes known in the art.

"Homologs" are bioactive molecules that are similar to a reference molecule at the nucleotide sequence, peptide sequence, functional, or structural level. Homologs may include sequence derivatives that share a certain percent identity with the reference sequence. Thus, in one embodiment, homologous or derivative sequences share at least a 70 percent sequence identity. In a preferred embodiment, homologous or derivative sequences share at least an 80 or 85 percent sequence identity. In a more preferred embodiment, homologous or derivative sequences share at least an 86, 87, 88, 89, 90, 91, 92, 93, 94, 95, 96, 97, 98, or 99 percent sequence identity. Homologous or derivative nucleic acid sequences may also be defined by their ability to remain bound to a reference nucleic acid sequence under high stringency hybridization conditions. Homologs having a structural or functional similarity to a reference molecule may be chemical derivatives of the reference molecule. Methods of detecting, generating, and screening for structural and functional homologs as well as derivatives are known in the art.

"Hybridization" generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al, Current Protocols in Molecular Biology, Wiley Interscience Publishers (1995).

An "individual," "subject" or "patient" is a vertebrate. In certain embodiments, the vertebrate is a mammal. Mammals include, but are not limited to, primates (including human and non-human primates) and rodents (e.g., mice, hamsters, guinea pigs, and rats). In certain embodiments, a mammal is a human. A "control subject" refers to a healthy subject who has not been diagnosed as having a disease, dysfunction, or condition that has been identified in an individual, subject, or patient. A control subject does not suffer from any sign or symptom associated with the disease, dysfunction, or condition.

A "medicament" is an active drug that has been manufactured for the treatment of a disease, disorder, or condition.

"Morpholinos" are synthetic molecules that are non-natural variants of natural nucleic acids that utilize a phosphorodiamidate linkage, described in U.S. Pat. No. 8,076,476, incorporated by reference herein in its entirety.

"Nucleic acids" are any of a group of macromolecules, either DNA, RNA, or variants thereof, that carry genetic information that may direct cellular functions. Nucleic acids may have enzyme-like activity (for instance ribozymes) or may be used to inhibit gene expression in a subject (for instance RNAi). The nucleic acids used in the inventions described herein may be single-stranded, double-stranded, linear or circular. The inventions further incorporate the use of nucleic acid variants including, but not limited to, aptamers, PNA, Morpholino, or other non-natural variants of nucleic acids. By way of example, nucleic acids useful for the invention are described in U.S. Pat. No. 8,076,476, incorporated by reference herein in its entirety.

"Patient response" or "response" can be assessed using any endpoint indicating a benefit to the patient, including, without limitation, (1) inhibition, to some extent, of disease progression, including stabilization, slowing down and complete arrest; (2) reduction in the number of disease episodes and/or symptoms; (3) inhibition (i.e., reduction, slowing down or complete stopping) of a disease cell infiltration into adjacent peripheral organs and/or tissues; (4) inhibition (i.e. reduction, slowing down or complete stopping) of disease spread; (5) decrease of an autoimmune condition; (6) favorable change in the expression of a biomarker associated with the disorder; (7) relief, to some extent, of one or more symptoms associated with a disorder; (8) increase in the length of disease-free presentation following treatment; or (9) decreased mortality at a given point of time following treatment.

As used herein, the term "peptide" is any peptide comprising two or more amino acids. The term peptide includes short peptides (e.g., peptides comprising between 2-14 amino acids), medium length peptides (15-50) or long chain peptides (e.g., proteins). The terms peptide, medium length peptide and protein may be used interchangeably herein. As used herein, the term "peptide" is interpreted to mean a polymer composed of amino acid residues, related naturally occurring structural variants, and synthetic non-naturally occurring analogs thereof linked via peptide bonds, related naturally-occurring structural variants, and synthetic non-naturally occurring analogs thereof. Synthetic peptides can be synthesized, for example, using an automated peptide synthesizer. Peptides can also be synthesized by other means such as by cells, bacteria, yeast or other living organisms. Peptides may contain amino acids other than the 20 gene-encoded amino acids. Peptides include those modified either by natural processes, such as processing and other post-translational modifications, but also by chemical modification techniques. Such modifications are well described in basic texts and in more detailed monographs, and are well-known to those of skill in the art. Modifications occur anywhere in a peptide, including the peptide backbone, the amino acid side chains, and the amino or carboxyl termini.

As used herein, a "pharmaceutically acceptable carrier" or "therapeutic effective carrier" is aqueous or nonaqueous (solid), for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of specific inhibitor, for example, carbohydrates, such as glucose, sucrose or dextrans, antioxidants such as ascorbic acid or glutathione, chelating agents, low molecular weight proteins or other stabilizers or excipients.

The term "pharmacokinetics" is defined as the time course of the absorption, distribution, metabolism, and excretion of a therapeutic compound. Improved "pharmacokinetic properties" are defined as: improving one or more of the pharmacokinetic properties as desired for a particular therapeutic compound. Examples include but are not limited to: reducing elimination through metabolism or secretion, increasing drug absorption, increasing half-life, and/or increasing bioavailability.

"PNA" refers to peptide nucleic acids with a chemical structure similar to DNA or RNA. Peptide bonds are used to link the nucleotides or nucleosides together.

"Scaffolds" are molecules to which other molecules can be covalently or non-covalently attached or formulated. The scaffolds of the invention may act as "spacers" between the targeting group and the drug. Spacers are molecular entities that provide physical distance between the two distinct molecular entities. Scaffolds may also contain a reactive "linker" or may have beneficial therapeutic properties in addition to the drug. Linkers are the sites of attachment from one molecular entity to another. Thus, the scaffolds of the invention may be, for example, PEG, serum albumin, thioredoxin, an immunoglobulin, a modifying group that contains a reactive linker, a water-soluble polymer, or a therapeutic compound. The scaffolds and linkers of the invention are stable (i.e. non-releasable). Non-releasable linkers have more stable chemical bonds than releasable linkers to allow the attached molecular entities to remain attached in vivo. In certain embodiments, however, they may be "releasable" under specific conditions. Releasable linkers have inherent instability and allow for the release of the attached molecules under certain conditions over time.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

"Stringent conditions" or "high stringency conditions", as defined herein, can be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µl/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

The "therapeutic compounds" disclosed herein refer to small molecules, chemical entities, nucleic acids, nucleic acid derivatives, peptides, peptide derivatives, naturally-occurring proteins, non-naturally-occurring proteins, glycoproteins, and steroids that are administered to subjects to treat diseases or dysfunctions or to otherwise affect the health of individuals. Non-limiting examples of therapeutic compounds include polypeptides such as enzymes, hormones, cytokines, or antibody fragments, antibody derivatives, drugs that affect metabolic function, as well as organic compounds such as analgesics, antipyretics, anti-inflammatory agents, antibiotics, anti-viral compounds, anti-fungal compounds, cardiovascular drugs, drugs that affect renal function, electrolyte metabolism, drugs that act on the central nervous system, chemotherapeutic compounds, receptor agonists and receptor antagonists. Therapeutic compounds include, for example, extracellular molecules such as serum factors including, but not limited to, plasma proteins such as serum albumin, immunoglobulins, apolipoproteins or transferrin, or proteins found on the surface of erythrocytes or lymphocytes. Thus, exemplary therapeutic compounds include small molecules, chemical entities, nucleic acids, nucleic acid derivatives, peptides, peptide derivatives, naturally-occurring proteins, non-naturally-occurring proteins, peptide-nucleic acids (PNA), stapled peptides, oligonucleotides, morpholinos, antisense drugs, RNA-based silencing drugs, aptamers, glycoproteins, enzymes, hormones, cytokines, interferons, growth factors, blood coagulation factors, antibodies, antibody fragments, antibody derivatives, toxin-conjugated antibodies, antibody-drug conjugates, metabolic effectors, analgesics, antipyretics, anti-inflammatory agents, antibiotics, anti-microbial agents, anti-viral agents, anti-fungal drugs, musculoskeletal drugs, cardiovascular drugs, renal drugs, pulmonary drugs, digestive disease drugs, hematologic drugs, urologic drugs, metabolism drugs, hepatic drugs, neurological drugs, anti-diabetes drugs, anti-cancer drugs, drugs for treating stomach conditions, drugs for treating colon conditions, drugs for treating skin conditions, and drugs for treating lymphatic conditions. The term "therapeutic compound" as used herein has essentially the same meaning as the terms "drug" or "therapeutic agent."

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

A "vitamin" is a recognized term in the art and is defined as a fat-soluble or water-soluble organic substance essential in minute amounts for normal growth and activity of the body and is obtained naturally from plant and animal foods or supplements.

"Vitamin D" is a group of fat-soluble secosteroids. Several forms (vitamers) of vitamin D exist. The two major forms are vitamin D2 or ergocalciferol, and vitamin D3 or cholecalciferol. Vitamin D without a subscript refers to vitamin D2, D3 or other forms known in the art. In humans, vitamin D can be ingested as cholecalciferol (vitamin D3) or ergocalciferol (vitamin D2). Additionally, humans can synthesize it from cholesterol when sun exposure is adequate. Cholecalciferol may be modified in the liver or in vitro to 25-hydroxycholecalciferol ("25-hydroxy Vitamin D"). In the kidney or in vitro, 25-hydroxy vitamin D can be modified into the distinct hormonal form of 1, 25-hydroxy vitamin D.

"Vitamin D binding protein" or "DBP" is a naturally circulating serum protein found in all mammals that, among other activities, can bind to and transport vitamin D and its analogs to sites in the liver and kidney where the vitamin is modified to its active form, and it retains vitamin D in its various forms in circulation for, on average, 30 days in humans. A DBP protein sequence is disclosed in SEQ ID NO:14 and an exemplary nucleic acid sequence encoding the DBP protein sequence is disclosed in SEQ ID NO:15. DBP has multiple naturally-occurring isoforms. Exemplary isoforms are available in the public sequence databases (e.g. Accession Nos. NM_001204306.1, NM_001204307.1, NM_000583.3, BC036003.1, M12654.1, X03178.1, AK223458, P_001191235.1, NP_000574.2, AAA61704.1, AAD13872.1, NP_001191236.1, AAA19662.2, 154269, P02774.1, EAX05645.1, AAH57228.1, AAA52173.1, AAB29423.1, AAD14249.1, AAD14250.1, and BAD97178.1).

The invention contemplates non-hormonal vitamin D conjugates that bind DBP or functional DBP variants and homologs that contain conservative or non-conservative amino acid substitutions that substantially retain DBP activity. DBP binding molecules or functional DBP variants may be identified using known techniques and characterized using known methods (Bouillon et al., J Bone Miner Res. 6(10):1051-7 (1991), Teegarden et. al., Anal. Biochemistry 199(2):293-299 (1991), McLeod et al, J Biol Chem. 264(2): 1260-7 (1989), Revelle et al., J. Steroid Biochem. 22:469-474 (1985)). The foregoing references are incorporated by reference herein in their entirety.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like.

The invention provides effective routes for administration of proteins, peptides, other biologics, nucleic acids, and small molecule drugs. The invention further provides effective routes of drug administration via transdermal, oral, parenteral, subcutaneous, intracutaneous, intravenous, intramuscular, intraarticular, intrasynovial, intrasternal, intrathecal, intralesional, intracranial injection, infusion, inhalation, ocular, topical, rectal, nasal, buccal, sublingual, vaginal, or implanted reservoir modes.

In addition, the inventions described herein provide compositions and methods for maintaining target binding activity, i.e. pharmacodynamics (PD), for therapeutic compounds. It further provides compositions and methods for improving the pharmacokinetic (PK) profiles of therapeutic compounds as described herein. The invention further provides compositions and methods for improved drug absorption profiles as compared to the drug absorption profiles for the drugs using the same routes of administration or different routes of administration but without the inventions described herein. The invention further provides compositions and methods for improved drug bioavailability profiles as compared to the drug bioavailability profiles for the drugs using the same routes of administration or different routes of administration but without the carriers described herein. The invention further provides compositions and methods for improved drug half-life profiles as compared to the drug half-life profiles for the drugs using the same routes of administration or different routes of administration but without the inventions described herein.

The invention also provides alternative routes of drug administration that are more cost-effective or favorable to the patients when compared to the drugs without the inventions described herein.

The non-hormonal vitamin D carriers disclosed herein may improve the absorption, half-life, bioavailability, or pharmacokinetic properties of the linked therapeutic compounds. While not wishing to be bound by theory, the carriers have the properties of binding to the body's natural DBP. DBP may transport the carrier-drug complex from the site of administration to the circulating serum. The vitamin D-DBP interaction may retain the therapeutic compounds in circulation for an extended period of time. This can prevent its excretion from the body and increase the exposure of the therapeutic compound in the body to achieve a longer lasting therapeutic effect. Additionally, a smaller dose of drug may be required when conjugated the carrier when compared to the unmodified form.

The therapeutic compound carrier conjugates of the invention typically have about 1, 2, 3, 4, 5, 6, 7, 8, 9, or 10 targeting groups individually attached to a therapeutic compound. The structure of each of the targeting groups attached to the therapeutic compound may be the same or different. In preferred embodiments, one or more targeting groups are stably or non-releasably attached to the therapeutic compound at the N-terminus, C-terminus, or other portion of a therapeutic protein. For example, a therapeutic compound carrier conjugate may comprise a targeting group attached to the N-terminus and additionally a targeting group attached to a lysine residue. In another embodiment, a therapeutic compound carrier conjugate has a targeting group attached to a therapeutic protein via a modification such as a sugar residue as part of a glycosylation site, or on an acylation site of a peptide or attached to a phosphorylation site or other natural or non-natural modifications that are familiar to one skilled in the art. Also contemplated are attachment sites using a combination of sites mentioned above. One preferred embodiment of the present invention comprises a targeting group that is attached to the therapeutic compound at one specific site on a therapeutic compound. In another preferred embodiment, the attachment site on a protein may be a cysteine, lysine, the N-terminus or C-terminus.

In another embodiment, the scaffold is a pharmaceutically acceptable carrier. In preferred embodiments, the scaffold is poly(ethylene glycol), polylysine, polyethyleneimine, poly(propyleneglycol), a peptide, serum albumin, thioredoxin, an immunoglobulin, an amino acid, a nucleic acid, a glycan, a modifying group that contain a reactive linker, a water-soluble polymer, a small carbon chain linker, or an additional therapeutic moiety.

In one embodiment, water-soluble scaffold moieties have some detectable degree of solubility in water. Methods to detect and/or quantify water solubility are well known in the art. Exemplary water-soluble polymers include peptides, saccharides, poly(ethers), poly(amines), poly(carboxylic acids) and the like.

Peptides can have mixed sequences or be composed of a single amino acid, e.g., poly(lysine). An exemplary polysaccharide is poly(sialic acid). An exemplary poly(ether) is poly(ethylene glycol), e.g. m-PEG. Poly(ethyleneimine) is an exemplary polyamine, and poly(acrylic) acid is a representative poly(carboxylic acid). The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein. The polymer backbone can be linear or branched.

Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), polyvinylpyrrolidone), polylysine, polyethyleneimine, poly(hydroxypropylmethacrylamide), poly($\alpha$-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of about 100 Da to about 100,000 Da.

In other embodiments, the scaffold moiety may be a peptide, serum albumin, thioredoxin, an immunoglobulin, an amino acid, a nucleic acid, a glycan, a modifying group that contains a reactive linker, a water-soluble polymer, a small carbon chain linker, or an additional therapeutic compound. In one embodiment, the scaffold moieties are non-toxic to humans and animals. In another embodiment, the scaffolds are endogenous serum proteins. In another embodiment, the scaffold moieties are water-soluble polymers. In another embodiment, the scaffolds are non-naturally-occurring polymers. In another embodiment, the scaffolds are naturally-occurring moieties that are modified by covalent attachment to additional moieties (e.g., PEG, poly(propylene glycol), poly(aspartate), biomolecules, therapeutic moieties, or diagnostic moieties). The scaffolds and linkers of the invention are stable (i.e. non-releasable). In certain embodiments, however, they may be "releasable" under specific conditions.

The conjugation of hydrophilic polymers, such as PEG, is known in the art. In its most common form, PEG is a linear polymer terminated at each end with hydroxyl groups: HO—CH2CH2O—(CH2CH2O)n-CH2CH2-OH where n typically ranges from about 3 to about 4000. In a preferred embodiment, the PEG has a molecular weight distribution that is essentially homodisperse. In another preferred embodiment, the PEG is a linear polymer. In another preferred embodiment the PEG is a branched polymer.

Many end-functionalized or branched derivatives and various sizes are known in the art and commercially available. By way of example, conjugation of the PEG or PEO may be carried out using the compositions and methods described herein and in U.S. Pat. No. 7,803,777 (Defrees et al.) and U.S. Pat. No. 4,179,337 (Davis et al.), each of which are incorporated by reference herein in their entirety.

In some embodiments, smaller therapeutic compounds are paired with smaller scaffold moieties and larger therapeutic compounds are paired with larger scaffold moieties. It is contemplated, however, that smaller therapeutic compounds could be paired with a larger scaffold moiety and vice versa. Smaller therapeutic compounds are defined as having a molecular weight of 1 Da to 10 kDa. Larger therapeutic compounds are defined as having a molecular weight of 10 kDa to 1000 kDa.

In some embodiments, a scaffold that is approximately equal to the molecular weight of a small therapeutic compound results in an efficacious carrier-drug conjugate. Improvements in efficacy may be obtained by empirically adjusting the scaffold size further. Without wishing to be bound by theory, the pharmacokinetic properties and efficacy of the conjugates may be enhanced when a scaffold (in combination with linkers as needed) is big enough to ablate potential steric hindrance of the drug by DBP binding and vice versa. Thus, a therapeutic compound is conjugated so that its active region is exposed and available for functional activity and the carrier is able to bind DBP. Additional embodiments provide non-releasable attachments that extend the circulation of therapeutics. In some small peptide embodiments such as ghrelin, the scaffold may be selected to be approximately equal to the molecular weight of the therapeutic. In some large protein embodiments, such as an antibody, the scaffold may be long enough to allow binding between the Vitamin D carrier and DBP.

In preferred embodiments, the conjugation of the therapeutic compound retains substantially all of its activity following the conjugation. The active region of given therapeutic may be known in the art or determined empirically. In other embodiments, the conjugate is therapeutically active while remaining linked to the carrier. This embodiment may maximize the time in circulation and as well as its efficacy.

The scaffolds of the present invention, for example, could have a molecular weight of 100 Daltons (Da.), 500 Da., 1000 Da., 2000 Da., 5000 Da., 10,000 Da., 15,000 Da., 20,000 Da., 30,000 Da., 40,000 Da. or 60,000 Da. In one embodiment of the invention, "small" scaffolds may be between about 100 Da. and 20,000 Da. In another embodiment, "large" scaffolds may be greater than about 20,000 Da. to about 200,000 Da. In preferred embodiments, the scaffold moiety is between about 100 Da. and 200,000 Da. In more preferred embodiments, the scaffold is between about 100 Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 20.00 Da. and 200,000 Da., 100,000 and 200,000 Da., 5000 Da. and 100,000 Da., 10,000 and 80,000 Da., 20,000 Da. and 60,000 Da., or 20,000 Da. and 40,000 Da. The size of the scaffolds may be varied to maximize absorption, bioavailability, circulating half-life, or efficacy of the conjugated therapeutic compound.

Another component of the carrier molecule preferably comprises a coupling group that is used to covalently attach the drug to the scaffold or the carrier. The coupling groups of the invention include an amine-reactive group, a thiol-reactive group, a maleimide group, a thiol group, an aldehyde group, an NHS-ester group, a haloacetyl group, an iodoacetyl group, a bromoacetyl groups, a SMCC group, a sulfo SMCC group, a carbodiimide group and bifunctional cross-linkers such as NHS-maleimido, combinations thereof, or other coupling groups familiar to persons skilled in the art. The coupling groups of the invention can promote thiol linkages, amide linkages, oxime linkages, hydrazone linkages, thiazolidinone linkages or utilize cycloaddition reactions also called click chemistry to couple the carrier to a therapeutic compound. In another embodiment, the composition preferably includes a combination of one or more therapeutic compounds attached to the coupling group of the scaffold molecule. The linkers of the invention may be between about 40 and 100 Daltons. In preferred embodiments, the linkers may be between about 40-50, 50-60, 60-70, 70-80, 80-90, or 90-100 Daltons. The linkers may also be varied to affect the stability or releasability of the link between the carrier and the therapeutic compound.

NHS groups are known to those skilled in the art as being useful for coupling to native peptides and proteins without having to engineer in a site of attachment. NHS groups allow attachment to most proteins and peptides that contain amino acids with amine groups such as a lysine residue. Utilization of NHS groups allows for flexibility in the site of carrier conjugation as protein structure and reaction time can influence the attachment site and number of carrier molecules conjugated to the therapeutic compound. By way of example, controlling the molar ratio of NHS-carrier to therapeutic compound, one skilled in the art can have some control over the number of carrier molecules attached to the therapeutic compound thus allowing for more than one carrier to be conjugated to a given therapeutic compound, if desired.

Conjugation of the carrier to a therapeutic compound is achieved by mixing a solution of the molecules together in a specific molar ratio using compatible solutions, buffers or solvents. For example, a molar ratio of about 1:1, 2:1, 4:1, 5:1, 10:1, 20:1, 25:1, 50:1, 100:1, 1000:1, or about 1:2, 1:4, 1:5, 1:10, 1:20 1:25, 1:50, 1:100 or 1:1000 of carrier to therapeutic compound could be used. By varying the ratio, this could result in different numbers of individual carriers attached to the therapeutic compound, or could help to select a specific site of attachment. Attachment of the carriers is also pH, buffer, salt and temperature dependent and varying these parameters among other parameters can influence the site of attachment, the number of carriers attached, and the speed of the reaction. For example, by selecting a pH for the reaction at or below pH 6 could help selectively conjugate an aldehyde version of the carrier to the N-terminus of the therapeutic protein or peptide.

Additionally, in order to retain substantially the same activity of the therapeutic compounds, conjugation to the carriers will be at a site on the molecules that do not interfere with therapeutic function. For proteins, it may require conjugation to the amino terminus, the carboxy terminus, or to an internal reactive amino acid. For nucleic acids, it may require conjugation to the 5' end, the 3' end, or an internal nucleotide, nucleoside, or a derivative thereof. In one embodiment, the carrier is conjugated to a nucleotide or nucleoside prior to incorporation into a polynucleotide molecule.

In certain embodiments, the present invention provides carriers that include those of formula I:

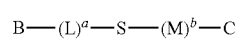

Wherein:
B is a targeting group selected from vitamin D, a vitamin D analog, a vitamin D-related metabolite, an analog of a vitamin D related-metabolite, a peptide that binds DBP, an anti-DBP antibody, an anti-DBP antibody derivative, a nucleotide aptamer that binds DBP, or a small carbon-based molecule that binds DBP;
S is a scaffold moiety, comprising poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, pol

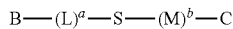

Wherein:
B is a targeting group selected from vitamin D, a vitamin D analog, a vitamin D-related metabolite, an analog of a vitamin D related-metabolite, or a small carbon-based molecule that binds DBP;
S is a scaffold moiety, comprising poly(ethylene glycol), polylysine, poly(propyleneglycol), a peptide, serum albumin, an amino acid, a nucleic acid, a glycan, polylactic acid, a water-soluble polymer, or a small carbon chain linker;
C is a maleimide group, a thiol group, a disulfide group, an aldehyde group, an NETS-ester group, an iodoacetyl group, or a bromoacetyl group;
$(L)^a$ and $(M)^b$ are linkers independently selected from —$(CH_2)_n$—, —C(O)NH—, —HNC(O)—, —C(O)O—, —OC(O)—, —O—, —S—S—, —S—, —S(O)—, —$S(O)_2$— and —NH—;
a is an integer from 0-4; and
b is an integer from 0-4; and
n is an integer from 0-3.

In more preferred embodiments, the present invention provides carriers that include those of formula I:

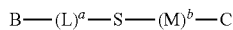

Wherein:
B is a targeting group selected from vitamin D, a vitamin D analog, or a vitamin D-related metabolite;
S is a scaffold moiety, comprising poly(ethylene glycol), polylysine or poly(propyleneglycol);
C is a maleimide group, a disulfide group, an aldehyde group, an NHS-ester group or an iodoacetyl group;
$(L)^a$ and $(M)^b$ are linkers independently selected from —$(CH_2)_n$—, —C(O)NH—, —HNC(O)—, —C(O)O—, —OC(O)—, —O—, —S—S—, —S—, —S(O)—, —$S(O)_2$— and —NH—;
a is an integer from 0-4; and
b is an integer from 0-4; and
n is an integer from 0-3.

In most preferred embodiments, the present invention provides carriers that include those of formulas IIa, IIb, and IIc:

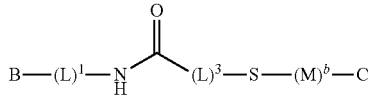

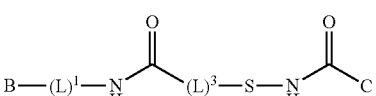

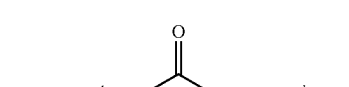

Wherein:
B is a targeting group selected from vitamin D, a vitamin D analog, or a vitamin D-related metabolite;
S is a scaffold moiety, comprising poly(ethylene glycol), or poly(propyleneglycol); and
C is a maleimide group, a disulfide group, an aldehyde group, an NETS-ester group or an iodoacetyl group;
$L^1$ is —$(CH_2)_n$—;
$L^3$ is —$(CH_2)_o$—;
$(M)^b$ are linkers independently selected from —$(CH_2)_n$—, —C(O)NH—, —HNC(O)—, —C(O)O—, —OC(O)—, —O—, —S—S—, —S—, —S(O)—, —$S(O)_2$— and —NH—;
b is an integer from 0-4; and
n is 3; and
o is 1.

In PCT/US2013/031788, which is incorporated herein by reference, conjugation at the Carbon 25 (C25) position of 25-hydroxy-vitamin $D_3$ is exemplified. The present invention incorporates conjugation at the C3 position of 25-hydroxy-vitamin $D_3$. This gives improved half-life extension and bioavailability compared to the C25 conjugates.

In certain most preferred embodiments of formula IIa, B is represented by formula III, S is poly(ethylene glycol) and $(M)^b$-C is represented by formula IVa.

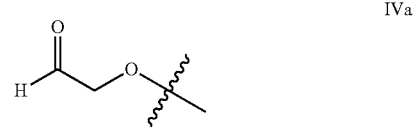

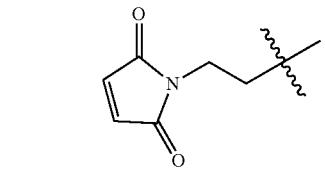

In certain most preferred embodiments of formula IIb, B is represented by formula III, S is poly(ethylene glycol) and $(M)^b$-C is represented by formula IVb.

27
-continued

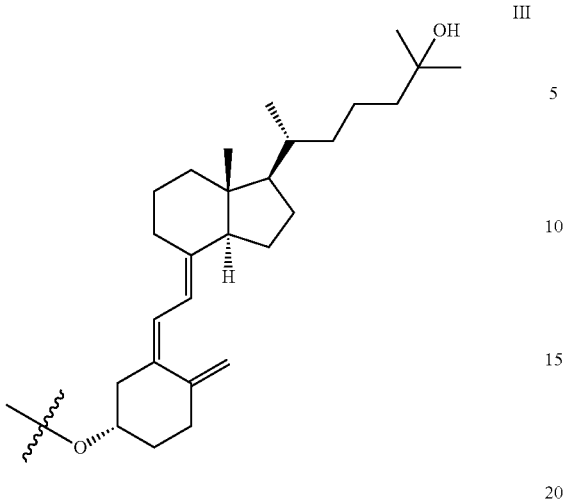

III

In certain most preferred embodiments of formula IIc, B is represented by formula III, S is poly(ethylene glycol) and (M)$^b$-C is represented by formula IVc.

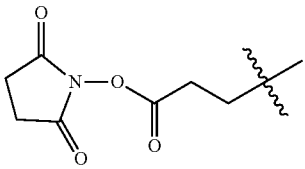

IVc

28
-continued

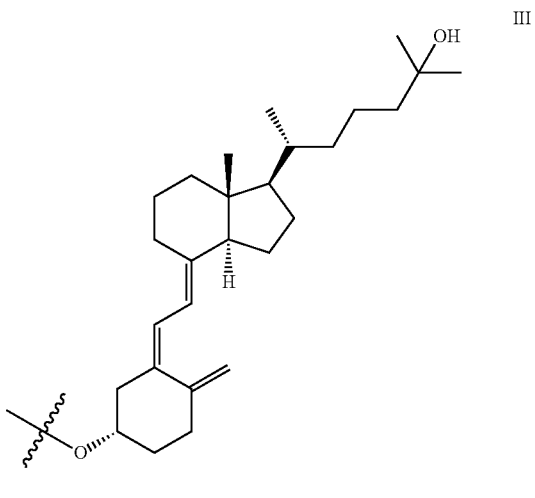

III

In certain most preferred embodiment, S is between about 100 Da. and 200,000 Da. In other most preferred embodiments, the scaffold moiety is between about 100 Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 5000 Da. and 100,000 Da., 10,000 Da. and 80,000 Da., 20,000 Da. and 60,000 Da., or 20,000 Da. and 40,000 Da.

In a specific embodiment, the present invention provides a carrier represented by formula V.

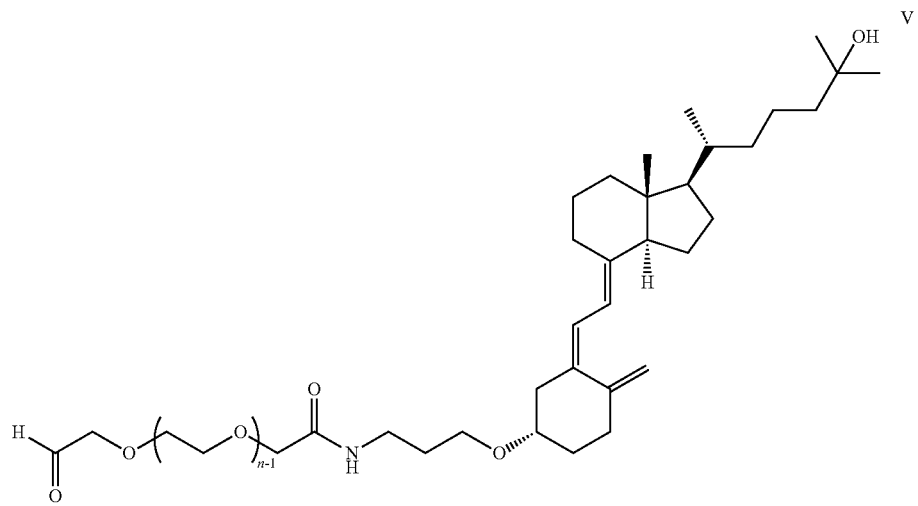

V

In another specific embodiment, the present invention provides a carrier represented by formula VI.

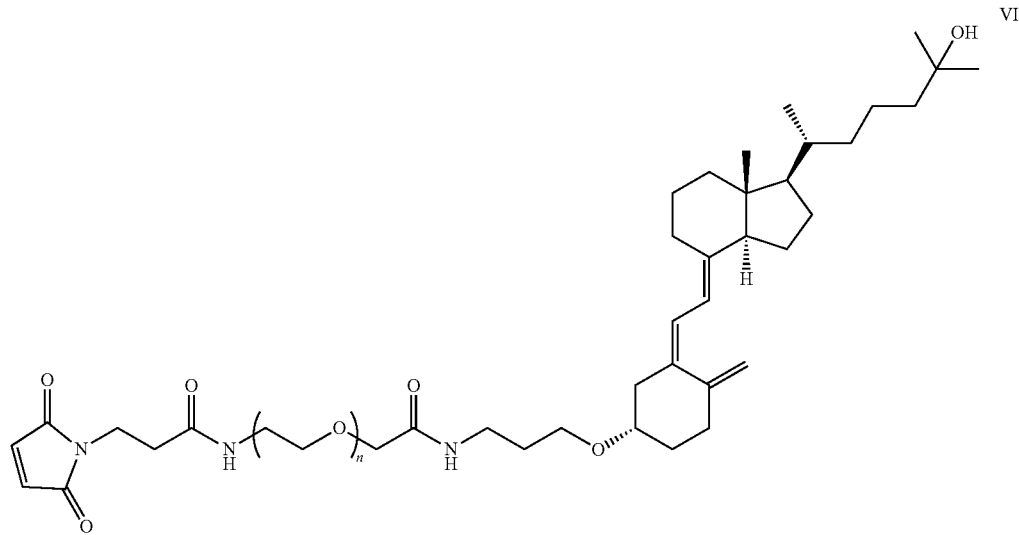

In another specific embodiment, the present invention provides a carrier represented by formula VII.

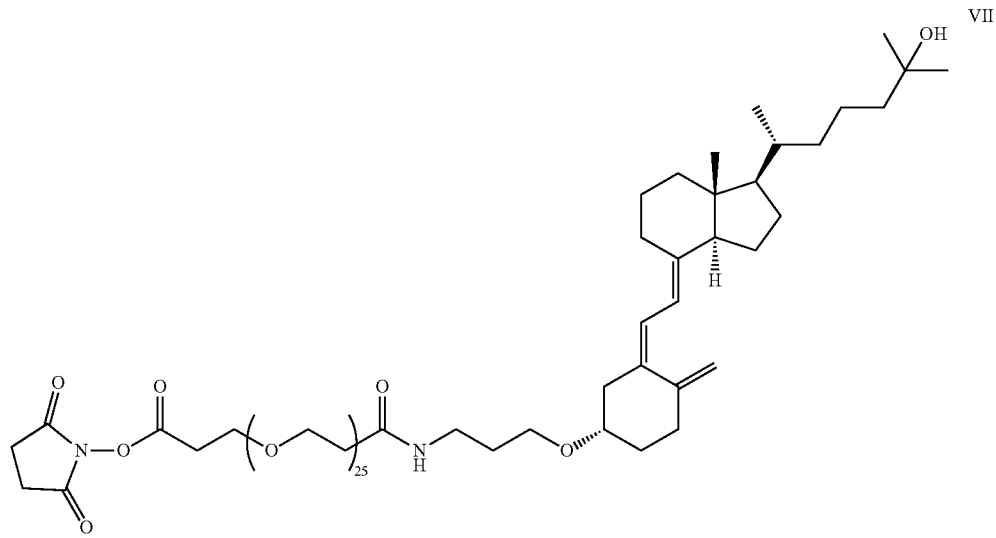

In certain embodiments, the present invention provides a method for producing a carrier of formula I:

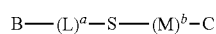

comprising the step of reacting a compound of formula Ia:

with a compound of formula Ib:

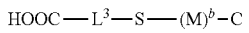

in the presence of an amide coupling agent,
wherein B, S, C and $L^1$, $L^3$, and $(M)^b$ are defined as above and $L^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

Any suitable amide coupling agent may be used to form a compound of formula I.

Suitable amide coupling agents include, but are not limited to 2-chloromethylpyridinium iodide, BOP, PyBOP, HBTU, HATU, DCC, EDCI, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

One skilled in the art will recognize that any suitable leaving group may be coupled with the carboxylic acid of formula Ib in the presence of a suitable coupling agent to form an active ester of formula Ic:

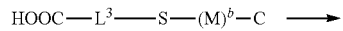

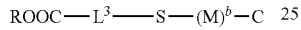

Ib

Ic wherein R is a suitable leaving group including, but are not limited to imidazole, HOBT, NHS and 4-nitrophenol. Suitable coupling reagents include, but are not limited to 2-chloromethylpyridinium iodide, BOP, PyBOP, HBTU, HATU, DCC, EDCI, TBTU and T3P. In some embodiments, the present invention provides a method for producing a carrier of formula I:

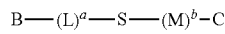

I comprising the step of reacting a compound of formula Ia:

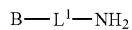

Ia with a compound of formula Ic:

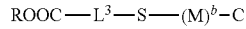

Ic wherein B, S, C, R and $L^1$, $L^3$, and $(M)^b$ are defined as above and $L^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

In certain embodiments, the amide coupling is performed with a base such as triethylamine or diisopropylethylamine. One skilled in the art will recognize that bases other than triethylamine or diisopropylethylamine may be used.

In certain other embodiments, the present invention provides a method for producing a carrier of formula IIa:

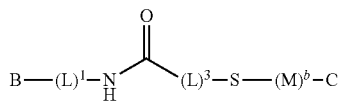

IIa comprising the steps of reacting a compound of formula Ia:

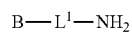

Ia with a compound of formula Id:

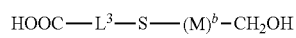

Id in the presence of an amide coupling agent forming a compound of formula Ie; and

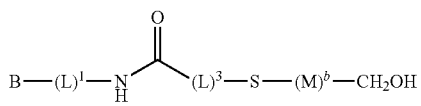

Ie

Oxidation of the primary alcohol of formula Ie to an aldehyde of formula IIa;

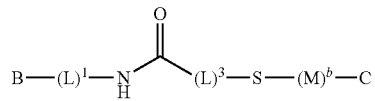

IIa wherein B, S, $L^1$, $L^3$, $(M)^b$, b, n and o are defined as above and $L^2$ is —C(O)NH— and C is an aldehyde group.

Any suitable oxidizing agent may be used to form a compound of formula IIa. Suitable oxidizing agents include, but are not limited to, the Collins reagent, PDC, PCC, oxalyl chloride/DMSO (Swern oxidation), $SO_3$-pyridine/DMSO (Parikh-Doehring oxidation), Dess-Martin periodinane, TPAP/NMO, and TEMPO/NaOCl.

One skilled in the art will recognize that a compound of formula Ia can be used either as a free base or as a suitable salt form. Suitable salt forms include, but are not limited to TFA, HCl, HBr, MsOH, TfOH and AcOH.

Any suitable amide coupling agent may be used to form a compound of formula Ie. Suitable amide coupling agents include, but are not limited to 2-chloromethylpyridinium iodide, BOP, PyBOP, HBTU, HATU, DCC, EDCI, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In certain embodiments, any suitable leaving group can be coupled with a carboxylic acid of formula Id in the presence of a suitable coupling reagent to form an active ester of formula If:

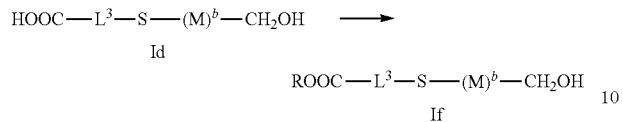

wherein R is a suitable leaving group including, but are not limited to imidazole, HOBT, NHS and 4-nitrophenol. Suitable coupling reagents include, but are not limited to 2-chloromethylpyridinium iodide, BOP, PyBOP, HBTU, HATU, DCC, EDCI, TBTU and T3P.

In some embodiments, the present invention provides a method for producing a carrier of formula Ie:

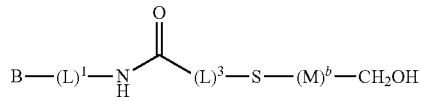

comprising the step of reacting a compound of formula Ia;

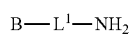

with a compound of formula If; and

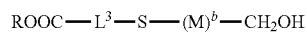

Oxidation of the primary alcohol of formula Ie to an aldehyde of formula IIa;

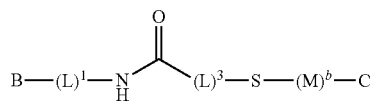

wherein B, S, C, R and $L^1$, $L^3$, and $(M)^b$ are defined as above and $L^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

In certain embodiments, the amide coupling is performed with a base such as triethylamine or diisopropylethylamine. One skilled in the art will recognize that bases other than triethylamine or diisopropylethylamine may be used.

Any suitable oxidizing agent may be used to form a compound of formula IIa. Suitable oxidizing agents include, but are not limited to, the Collins reagent, PDC, PCC, oxalyl chloride/DMSO (Swern oxidation), SO$_3$-pyridine/DMSO (Parikh-Doehring oxidation), Dess-Martin periodinane, TPAP/NMO, and TEMPO/NaOCl.

In certain other embodiments, the present invention provides a method for producing a carrier of formula IIc:

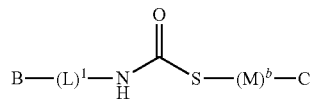

comprising the steps of reacting a compound of formula Ia:

with a compound of formula Ig:

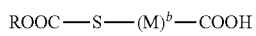

forming a compound of formula Ih; and

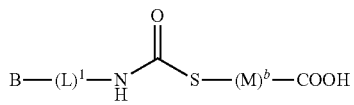

Converting a carboxylic acid of formula Ih to an active ester of formula IIc;

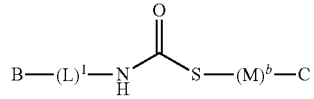

wherein B, S, C, R, $L^1$, $(M)^b$, b, n and o are defined as above and $L^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

Any suitable leaving group can be coupled with a carboxylic acid of formula Ih in the presence of a suitable coupling reagent to form an active ester of formula IIc. Suitable leaving groups include, but are not limited to imidazole, HOBT, NHS and 4-nitrophenol. Suitable coupling reagents include, but are not limited to 2-chloromethylpyridinium iodide, BOP, PyBOP, HBTU, HATU, DCC, EDCI, TBTU and T3P.

In some embodiments, an active ester of formula IIc is formed from a carboxylic acid of formula Ih using a combination of a suitable leaving group and a coupling reagent.

In some embodiments, an active ester of formula IIc is formed from a carboxylic acid of formula Ih using a single reagent that produces a leaving group and also effects a coupling reaction. Such reagents include, but are not limited to 1,1'-carbonyldiimidazole, N,N'-disuccinimidyl carbonate, 4-nitrophenyl trifluoroacetate and HBTU. In some embodiments, the single reagent is used alone. In other embodiments, the single reagent is used with an acyl transfer catalyst. Such acyl transfer catalysts include, but are not limited to DMAP and pyridine. One skilled in the art will recognize that additional acyl transfer catalysts may be used.

In a specific embodiment, the present invention provides a method for producing a carrier represented by formula V:

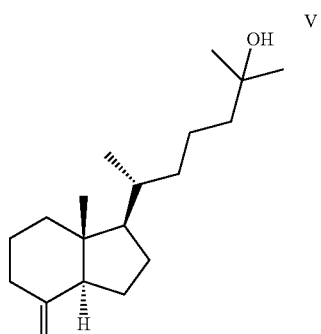
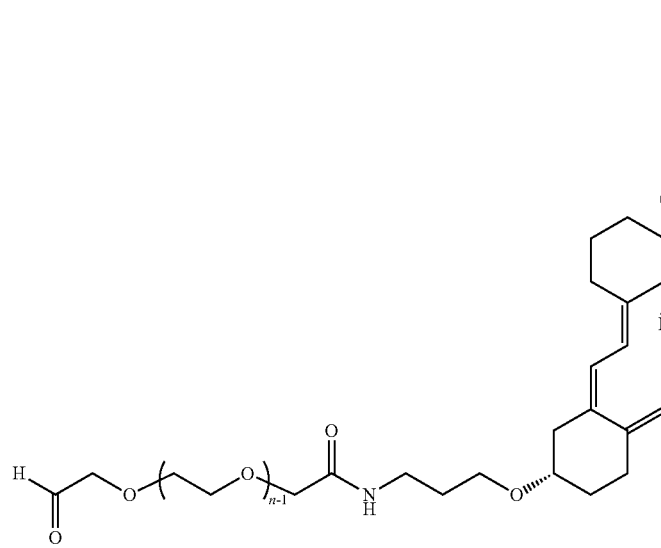
comprising the step of reacting a compound of formula Va:
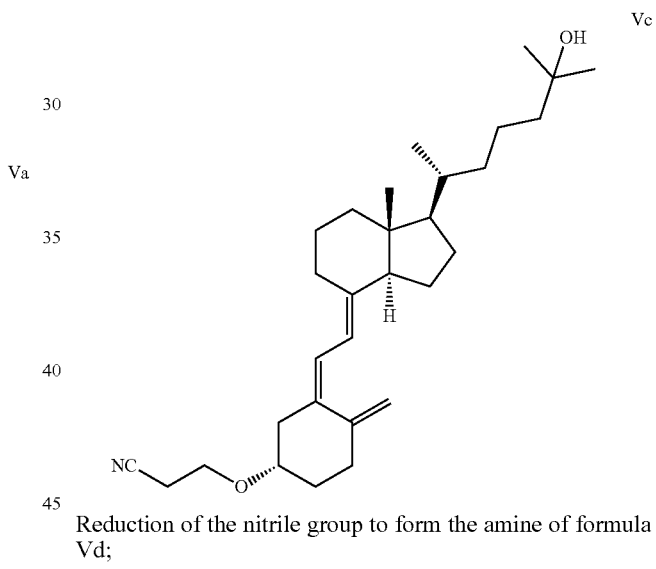
to form a compound of formula Vc;
Reduction of the nitrile group to form the amine of formula Vd;
with a compound of formula Vb:
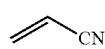

Reaction of the compound of formula Vd with a compound of formula Ve; To form a compound of the formula Vf
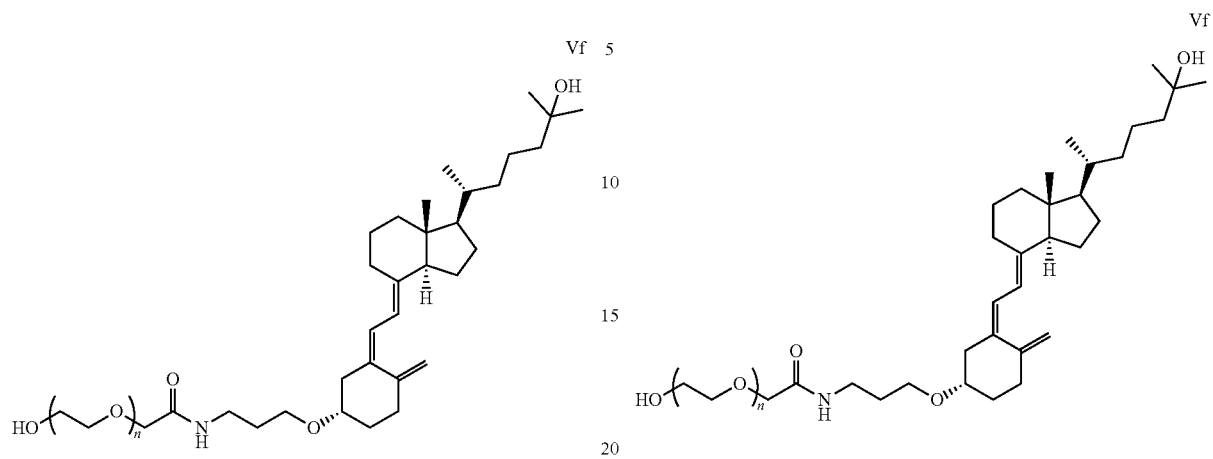
Oxidation of the primary alcohol of formula Vf to form the aldehyde of formula V.
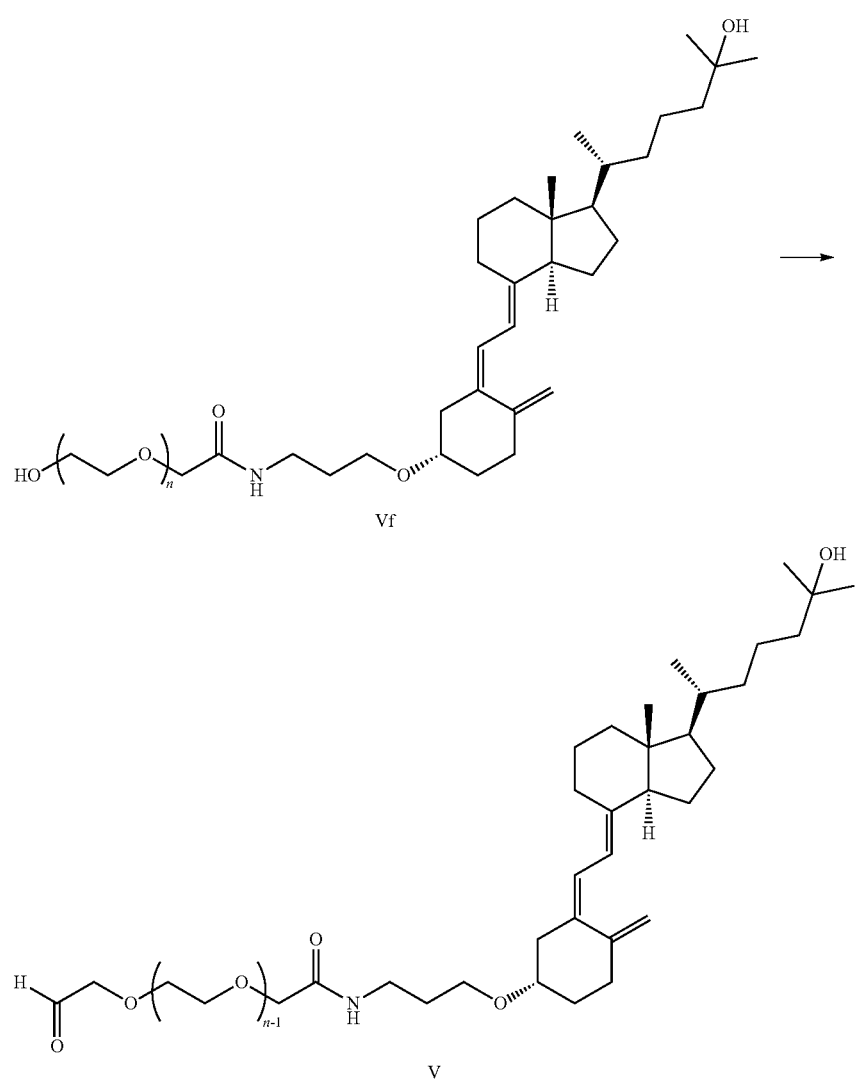

In some embodiments, the reaction of a compound of formula Vb with a compound of formula Va is promoted by addition of Triton B. One skilled in the art will recognize that other reagents may be used to promote nucleophilic addition to acrylonitrile.

In some embodiments, reduction of the nitrile of formula Vc to the amine of formula Vd is performed using $AlCl_3$/LAH. One skilled in the art will recognize that other reduction reagents may be used including sodium, $H_2$/Pd, $H_2$/Raney nickel, and diborane.

One skilled in the art will recognize that a compound of formula Vd can be used either as a free base or as a suitable salt form. Suitable salt forms include, but are not limited to TFA, HCl, HBr, MsOH, TfOH and AcOH.

In certain embodiments, a base such as triethylamine or diisopropylethylamine is used to promote coupling of the NETS-ester of formula Ve with the amine of formula Vd. One skilled in the art will recognize that bases other than triethylamine or diisopropylethylamine may be used.

Any suitable oxidizing agent may be used to form a compound of formula V. Suitable oxidizing agents include, but are not limited to, the Collins reagent, PDC, PCC, oxalyl chloride/DMSO (Swern oxidation), $SO_3$-pyridine/DMSO (Parikh-Doehring oxidation), Dess-Martin periodinane, TPAP/NMO, and TEMPO/NaOCl.

In another specific embodiment, the present invention provides a method for producing a carrier represented by formula VI:

comprising the steps of reacting a compound of formula Vd:

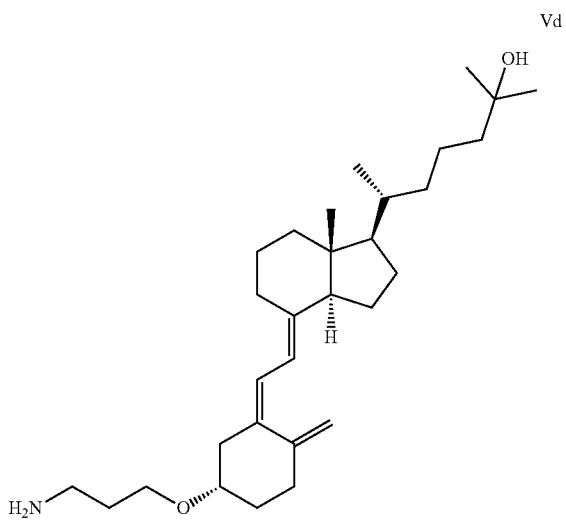 [SMILES: C=C1CC[C@H](OCCCN)C/C1=C/C=C1\CCC[C@]2(C)[C@@H]([C@H](C)CCCC(C)(C)O)CC[C@@H]12]

in the presence of an amide coupling agent with a compound of formula VIa:

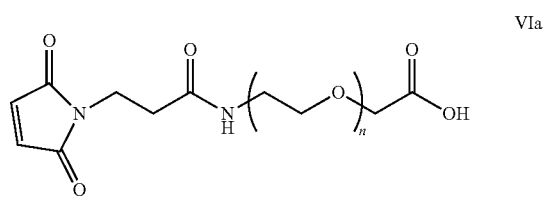

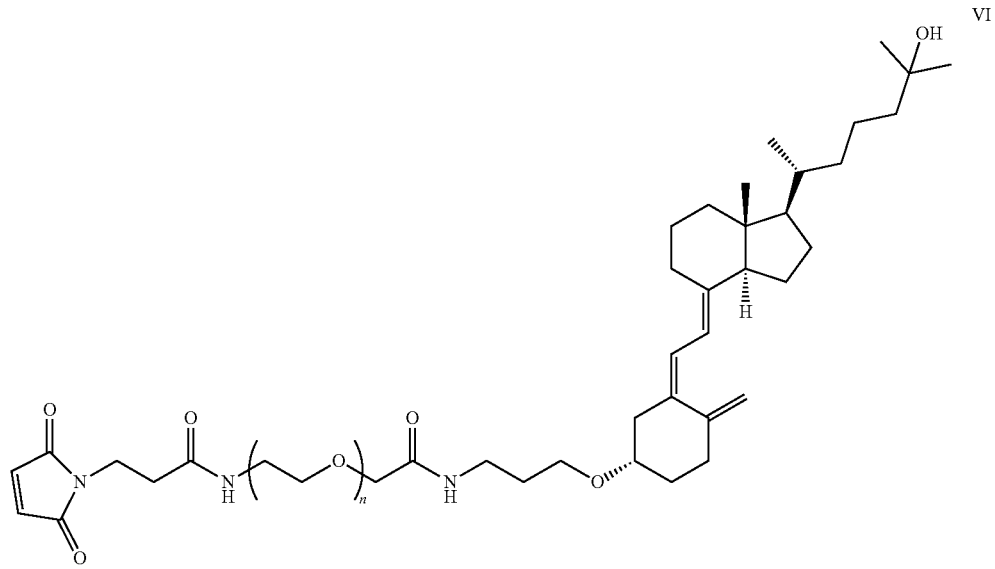

One skilled in the art will recognize that a compound of formula Vd can be used either as a free base or as a suitable salt form. Suitable salt forms include, but are not limited to TFA, HCl, HBr, MsOH, TfOH and AcOH.

Any suitable amide coupling agent may be used to form a compound of formula VI. Suitable amide coupling agents include, but are not limited to 2-chloromethylpyridinium iodide, BOP, PyBOP, HBTU, HATU, DCC, EDCI, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In another specific embodiment, the present invention provides a method for producing a carrier represented by formula VII:

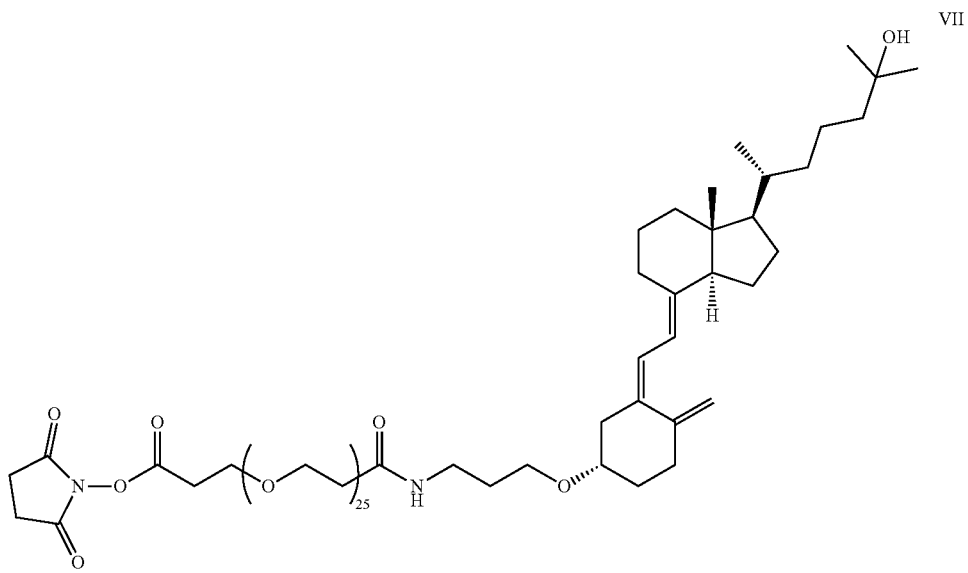

comprising the steps of reacting a compound of formula Vd:

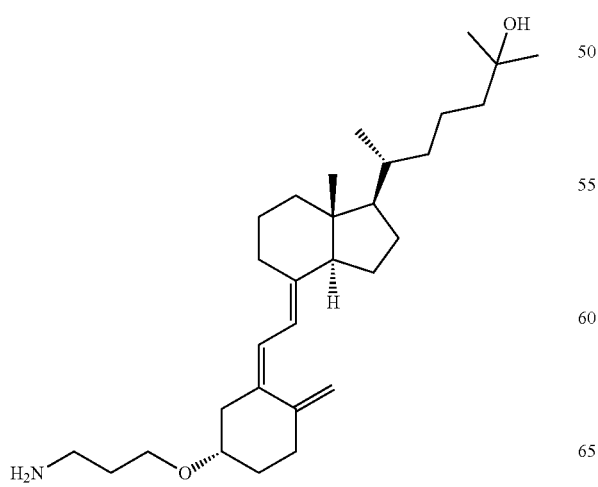

with a compound of formula VIIa:

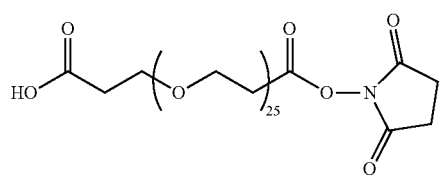

forming a compound of formula VIIb; and

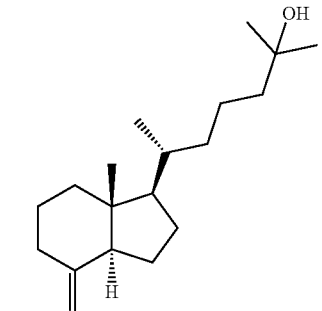

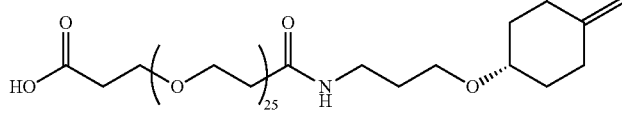

Converting a carboxylic acid of formula VIIb to an active ester of formula VII;

One skilled in the art will recognize that bases other than triethylamine or diisopropylethylamine may be used.

NETS can be coupled with a carboxylic acid of formula VIIb in the presence of a suitable coupling reagent to form an active ester of formula VII. Suitable coupling reagents include, but are not limited to 2-chloromethylpyridinium iodide, BOP, PyBOP, HBTU, HATU, DCC, EDCI, TBTU, and T3P.

In some embodiments, an active ester of formula VII is formed from a carboxylic acid of formula VIIb using a combination of NETS and a coupling reagent.

In some embodiments, an active ester of formula VII is formed from a carboxylic acid of formula VIIb using a

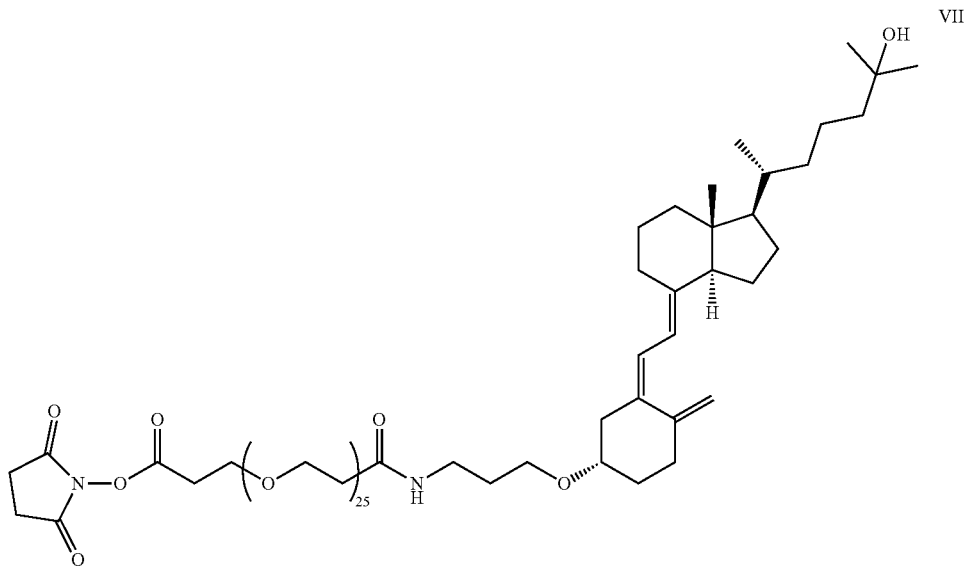

One skilled in the art will recognize that a compound of formula Vd can be used either as a free base or as a suitable salt form. Suitable salt forms include, but are not limited to TFA, HCl, HBr, MsOH, TfOH and AcOH.

In certain embodiments, a base such as triethylamine or diisopropylethylamine is used to promote coupling of the NETS-ester of formula VIIa with the amine of formula Va.

single reagent that produces a leaving group and also effects a coupling reaction. Such reagents include, but are not limited to, N,N'-disuccinimidyl carbonate. In some embodiments, the single reagent is used alone. In other embodiments the reagent is used with an acyl transfer catalyst. Such acyl transfer catalysts include, but are not limited to DMAP and pyridine. One skilled in the art will recognize that additional acyl transfer catalysts may be used.

One skilled in the art will recognize that there are other methods to conjugate a linker and scaffold to the C3 position of vitamin D derivatives and analogues. For example, the C3 hydroxy group may be acylated by various groups as practiced by N. Kobayashi, K. Ueda, J. Kitahori, and K. Shimada, *Steroids*, 57, 488-493 (1992); J. G Haddad, et al., *Biochemistry*, 31, 7174-7181 (1992); A. Kutner, R. P. Link, H. K. Schnoes, H. F. DeLuca, *Bioorg. Chem.*, 14, 134-147 (1986); and R. Ray, S. A. Holick, N. Hanafin, and M. F. Holick, *Biochemistry*, 25, 4729-4733 (1986). The foregoing references are incorporated by reference in their entirety. One skilled in the art will recognize that these chemistries could be modified to synthesize compounds of the formula I:

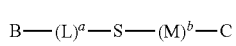

wherein B, S, C, $(L)^a$, and $(M)^b$ are defined as above.

If desired, therapeutic compound carrier conjugates having different molecular weights can be isolated using gel filtration chromatography and/or ion exchange chromatography. Gel filtration chromatography may be used to fractionate different therapeutic compound carrier conjugates (e.g., 1-mer, 2-mer, 3-mer, and so forth, wherein "1-mer" indicates one targeting group molecule per therapeutic compound, "2-mer" indicates two targeting groups attached to therapeutic compound, and so on) on the basis of their differing molecular weights (where the difference corresponds essentially to the average molecular weight of the targeting group).

Gel filtration columns suitable for carrying out this type of separation include Superdex and Sephadex columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, and (iii) sodium dodecyl sulfate polyacrylamide gel electrophoresis (SDS PAGE).

Separation of therapeutic compound carrier conjugates can also be carried out by reverse phase chromatography using a reverse phase-high performance liquid chromatography (RP-HPLC) C18 column (Amersham Biosciences or Vydac) or by ion exchange chromatography using an ion exchange column, e.g., a DEAE- or CM-Sepharose ion exchange column available from Amersham Biosciences. The resulting purified compositions are preferably substantially free of the non-targeting group-conjugated therapeutic compound. In addition, the compositions preferably are substantially free of all other non-covalently attached targeting groups.

As described herein, the carriers of the invention may be non-hormonal 25-hydroxy vitamin D or analogs thereof having a coupling group on the 3' carbon. "25-hydroxy vitamin D analogs" as used herein includes both naturally-occurring vitamin D metabolite forms as well as other chemically-modified forms. The carriers of the invention do not include an active (i.e. hormonal) form of vitamin D (typically having a hydroxyl group at the 1 carbon). These compounds are based on the vitamin D structure and retain partial function of vitamin D (i.e. they interact with DBP), albeit at varying affinities. The following list exemplifies vitamin D analog forms known in the art. They may, however, be hormonal or have the C1 hydroxyl group. They are presented here solely for their chemical properties as vitamin D analogs, not for their functional hormonal properties: OCT, a chemically synthesized version of $1,25(OH)_2D_3$ with an oxygen atom at the 22 position in the side chain (Abe et. al., FEBS Lett. 226:58-62 (1987)); Gemini vitamin D analog, 1α,25-dihydroxy-20R-21(3-hydroxy-3-deuteromethyl-4,4,4-trideuterobutyl)-23-yne-26,27-hexafluoro-cholecalciferol (BXL0124) (So et al., Mol Pharmacol. 79(3): 360-7 (2011)); Paricalcitol, a vitamin $D_2$ derived sterol lacking the carbon-19 methylene group found in all natural vitamin D metabolites (Slatopolsky et al., Am J. Kidney Dis. 26: 852 (1995)); Doxercalciferol (1α-hydroxyvitamin $D_2$), like alfacalcidol (1α-hydroxyvitamin $D_3$), is a prodrug which is hydroxylated in the liver to $1α,25(OH)_2D_2$, however, unlike alfacalcidol, doxercalciferol is also 24-hydroxylated to produce $1α,24(S)-(OH)_2D_2$ (Knutson et al., Biochem Pharmacol 53: 829 (1997)); Dihydrotachysterol$_2$ ($DHT_2$), hydroxylated in vivo to $25(OH)DHT_2$, $1,25(OH)_2DHT_2$ (McIntyre et al., Kidney Int. 55: 500 (1999)), ED-71, and eldecalcitol. See also Erben and Musculoskel, Neuron Interact. 2(1):59-69 (2001) and Steddon et al. Nephrol. Dial. Transplant. 16 (10): 1965-1967 (2001). The foregoing references are incorporated by reference in their entirety.

In another embodiment, the carrier further comprises a pharmaceutically acceptable scaffold moiety covalently attached to the targeting group and the therapeutic compound. The scaffold moiety of the carriers of the invention does not necessarily participate in but may contribute to the function or improve the pharmacokinetic properties of the therapeutic compound. The scaffolds of the invention do not substantially interfere with the binding of the targeting group to DBP. Likewise, the scaffolds of the invention do not substantially interfere with structure or function of the therapeutic compound. The length of the scaffold moiety is dependent upon the character of the targeting group and the therapeutic compound. One skilled in the art will recognize that various combinations of atoms provide for variable length molecules based upon known distances between various bonds (Morrison, and Boyd, Organic Chemistry, 3rd Ed, Allyn and Bacon, Inc., Boston, Mass. (1977), incorporated herein by reference). Other scaffolds contemplated by the invention include peptide linkers, protein linkers such as human serum albumin or immunoglobulin family proteins or fragments thereof, nucleic acid linkers, small carbon chain linkers, carbon linkers with oxygen or nitrogen interspersed, or combinations thereof. In preferred embodiments, the linkers are non-releasable or stable.

Also within the scope of the invention are therapeutic peptides. The term peptide is meant to include a string of amino acids. The amino acids in the peptides of the invention may be naturally-occurring or non-naturally-occurring. The peptides of the invention may be synthesized chemically or biologically, and can include cysteine-rich peptides, circular peptides, stapled peptides, peptides that include D- or L-amino acids and mixtures thereof, peptidomimetics, peptide-nucleic acids (PNAs), and combinations thereof. Exemplary embodiments include AIDS vaccines, allergy vaccines, anti-inflammatory peptides, anti-integrin peptides, anti-TCR vaccines, anti-allergy peptides, anti-cancer peptides, anti-fungal peptides, anti-bacterial peptides, anti-rheumatic peptides, anti-thrombin peptides, anti-viral peptides, G Protein-Coupled Receptor (GPCR) ligands and related peptides (e.g. the secretin family), CGRP s, GPCR antagonists, CMV peptides, calpain inhibitors, collagenase inhibitors, DAP inhibitors, defensins, dialytic oligopeptides, Enhancins, endorphins, endothelin antagonists, fibronectin inhibitors, gastrin antagonists, ghrelin, glucagon antagonists, gonadorelin analogs, growth factor peptides, hypothalamic hormones, pituitary hormones, peptides that control gut function and appetite, proinflammatory adipose tissue products, peptides that stimulate stem cell proliferation, proinflammatory peptides, natural products, herpes simplex vaccines, heparin binding peptides, hepatitis-B vaccines, immunomodulating peptides, influenza vaccines, LHRH antagonists, opiod peptide derivatives, MMP inhibitors, MUC-1 vaccines, malaria vaccines, melanoma vaccines, meningitis vaccines, neuropeptides, opioid peptides, osteogenic growth peptides, osteoporosis peptides, papillomavirus vaccines, prostate cancer vaccines, RGD peptides, RSV vaccines, T cell receptor peptides and the like. The invention contemplates synthetic analogs thereof that would be improved as clinical products through further modification by the methods described herein. Those skilled in the art will recognize many additional commercially important peptides that are amenable to modifications described herein to provide increased half-life, duration of action, absorption and/or bioavailability.

Also contemplated within the scope of embodiments described herein are therapeutic peptides that are branched or cyclic, with or without branching. Cyclic, branched and branched circular peptides result from post-translational natural processes and are also made by suitable synthetic methods. In some embodiments, any peptide product described herein comprises a peptide analog described above that is then covalently attached to an alkyl-glycoside surfactant moiety.

Other embodiments include therapeutic peptide chains that are comprised of natural and unnatural amino acids or analogs of natural amino acids. As used herein, peptide and/or protein "analogs" comprise non-natural amino acids based on natural amino acids, such as tyrosine analogs, which includes para-substituted tyrosines, ortho-substituted tyrosines, and meta-substituted tyrosines, wherein the substituent on the tyrosine comprises an acetyl group, a benzoyl group, an amino group, a hydrazine, an hydroxyamine, a thiol group, a carboxy group, a methyl group, an isopropyl group, a C2-C20 straight chain or branched hydrocarbon, a saturated or unsaturated hydrocarbon, an O-methyl group, a polyether group, a halogen, a nitro group, or the like.

Additional embodiments include therapeutic peptide chains having modified amino acids. Examples include acylated amino acids at the ε-position of Lysine, amino acids with fatty acids such as octanoic, decanoic, dodecanoic, tetradecanoic, hexadecanoic, octadecanoic, 3-phenylpropanoic acids and the like, or with saturated or unsaturated alkyl chains. (Zhang, L. and Bulaj, G (2012) Curr Med Chem 19: 1602-1618, incorporated herein by reference in its entirety).

The invention further contemplates therapeutic peptide chains comprising natural and unnatural amino acids or analogs of natural amino acids. In some embodiments, peptide or protein "analogs" comprise non-natural amino acids based on natural amino acids, such as tyrosine analogs, which includes para-substituted tyrosines, ortho-substituted tyrosines, and meta-substituted tyrosines, wherein the substituent on the tyrosine comprises an acetyl group, a benzoyl group, an amino group, a hydrazine, an hydroxyamine, a thiol group, a carboxy group, a methyl group, an isopropyl group, a C2-C20 straight chain or branched hydrocarbon, a saturated or unsaturated hydrocarbon, an O-methyl group, a polyether group, a halogen, a nitro group, or the like. Examples of Tyr analogs include 2,4-dimethyl-tyrosine (Dmt), 2,4-diethyl-tyrosine, O-4-allyl-tyrosine, 4-propyl-tyrosine, Ca-methyl-tyrosine and the like. Examples of lysine analogs include ornithine (Orn), homo-lysine, Ca-methyl-lysine (CMeLys), and the like. Examples of phenylalanine analogs include, but are not limited to, meta-substituted phenylalanines, wherein the substituent comprises a methoxy group, a C1-C20 alkyl group, for example a methyl group, an allyl group, an acetyl group, or the like. Specific examples include, but are not limited to, 2,4,6-trimethyl-L-phenylalanine (Tmp), O-methyl-tyrosine, 3-(2-naphthyl)alanine (Nal(2)), 3-(1-naphthyl)alanine (Nal(1)), 3-methyl-phenylalanine, 1,2,3,4-tetrahydroisoquinoline-3-carboxylic acid (Tic), fluorinated phenylalanines, isopropyl-phenylalanine, p-azido-phenylalanine, p-acyl-phenylalanine, p-benzoyl-phenylalanine, p-iodo-phenylalanine, p-bromophenyl-alanine, p-amino-phenylalanine, and isopropyl-phenylalanine, and the like.

Also contemplated within the scope of embodiments are therapeutic peptide chains containing nonstandard or unnatural amino acids known to the art, for example, C-alpha-disubstituted amino acids such as Aib, Ca-diethylglycine (Deg), aminocyclopentane-1-carboxylic acid (Ac4c), aminocyclopentane-1-carboxylic acid (Ac5c), and the like. Such amino acids frequently lead to a restrained structure, often biased toward an alpha helical structure (Kaul, R. and Balaram, P. (1999) Bioorg Med Chem 7: 105-117, incorporated herein by reference in its entirety). Additional examples of such unnatural amino acids useful in analog design are homo-arginine (Har) and the like. Substitution of reduced amide bonds in certain instances leads to improved protection from enzymatic destruction or alters receptor binding. By way of example, incorporation of a Tic-Phe dipeptide unit with a reduced amide bond between the residues (designated as Tic-F[CH2-NH]ˆ-Phe) reduces enzymatic degradation.

In some embodiments, modifications at the amino or carboxyl terminus may optionally be introduced into the present peptides or proteins (Nestor, J. J., Jr. (2009) Current Medicinal Chemistry 16: 4399-4418). For example, the present peptides or proteins can be truncated or acylated on the N-terminus (Gourlet, P., et al. (1998) Eur J Pharmacol 354: 105-111, Gozes, I. and Furman, S. (2003) Curr Pharm Des 9: 483-494), the contents of which is incorporated herein by reference in their entirety). Other modifications to the N-terminus of peptides or proteins, such as deletions or incorporation of D-amino acids such as D-Phe result in potent and long acting agonists or antagonists when substituted with the modifications described herein such as long chain alkyl glycosides.

Thus, the invention provides therapeutic compound analogs wherein the native therapeutic compound is modified by acetylation, acylation, PEGylation, ADP-ribosylation, amidation, covalent attachment of a lipid or lipid derivative, covalent attachment of phosphotidylinositol, cross-linking, cyclization, disulfide bond formation, demethylation, formation of covalent cross-link formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, (Nestor, J. J., Jr. (2007) Comprehensive Medicinal Chemistry II 2: 573-601, Nestor, J. J., Jr. (2009) Current Medicinal Chemistry 16: 4399-4418, Uy, R. and Wold, F. (1977) Science 198:890-6, Seifter, S. and England, S. (1990) Methods Enzymol 182: 626-646, Rattan, S. I., et al. (1992) Ann NY Acad Sci 663: 48-62). The foregoing references are incorporated by reference in their entirety.

Glycosylated therapeutic peptides may be prepared using conventional Fmoc chemistry and solid phase peptide synthesis techniques, e.g., on resin, where the desired protected glycoamino acids are prepared prior to peptide synthesis and then introduced into the peptide chain at the desired position during peptide synthesis. Thus, the therapeutic peptide polymer conjugates may be conjugated in vitro. The glycosylation may occur before deprotection. Preparation of amino acid glycosides is described in U.S. Pat. No. 5,767,254, WO 2005/097158, and Doores, K., et al., Chem. Commun., 1401-1403, 2006, which are incorporated herein by reference in their entirety. For example, alpha and beta selective glycosylations of serine and threonine residues are carried out using the Koenigs-Knorr reaction and Lemieux's in situ anomerization methodology with Schiff base intermediates. Deprotection of the Schiff base glycoside is then carried out using mildly acidic conditions or hydrogenolysis. A composition, comprising a glycosylated therapeutic peptide conjugate is made by stepwise solid phase peptide synthesis involving contacting a growing peptide chain with protected amino acids in a stepwise manner, wherein at least one of the protected amino acids is glycosylated, followed by water-soluble polymer conjugation. Such compositions may have a purity of at least 95%, at least 97%, or at least 98%, of a single species of the glycosylated and conjugated therapeutic peptide.

Monosaccharides that may by used for introduction at one or more amino acid residues of the therapeutic peptides defined and/or disclosed herein include glucose (dextrose), fructose, galactose, and ribose. Additional monosaccharides suitable for use include glyceraldehydes, dihydroxyacetone, erythrose, threose, erythrulose, arabinose, lyxose, xylose, ribulose, xylulose, allose, altrose, mannose, N-Acetylneuraminic acid, fucose, N-Acetylgalactosamine, and N-Acetylglucosamine, as well as others. Glycosides, such as mono-, di-, and trisaccharides for use in modifying a therapeutic peptide, one or more amino acid residues of the therapeutic peptides defined and/or disclosed herein include sucrose, lactose, maltose, trehalose, melibiose, and cellobiose, among others. Trisaccharides include acarbose, raffinose, and melezitose.

In further embodiments of the invention, the therapeutic compounds defined and/or disclosed herein may be chemically coupled to biotin. The biotin/therapeutic compound can then bind to avidin.

Also within the scope of the invention are polypeptides that are antibodies. The term antibody is meant to include monoclonal antibodies, polyclonal antibodies, toxin-conjugated antibodies, drug-conjugated antibodies (ADCs), humanized antibodies, antibody fragments (e.g., Fc domains), Fab fragments, single chain antibodies, bi- or multi-specific antibodies, Llama antibodies, nano-bodies, diabodies, affibodies, Fv, Fab, F(ab')2, Fab', scFv, scFv-Fc, and the like. Also included in the term are antibody-fusion proteins, such as Ig chimeras. Preferred antibodies include humanized or fully human monoclonal antibodies or fragments thereof.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region. "Antibody fragments" comprise a portion of an intact antibody, preferably comprising the antigen binding region thereof. Examples of antibody fragments include Fab, Fab', F(ab')2, and Fv fragments; diabodies; linear antibodies; single-chain antibody molecules; and multispecific antibodies formed from antibody fragments. The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies.

In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations that typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

Antibodies that bind specifically to an antigen have a high affinity for that antigen. Antibody affinities may be measured by a dissociation constant (Kd). In certain embodiments, an antibody provided herein has a dissociation constant (Kd) of equal to or less than about 100 nM, 10 nM, 1 nM, 0.1 nM, 0.01 nM, or 0.001 nM (e.g. $10^{-7}$M or less, from $10^{-7}$ M to $10^{-13}$M, from $10^{-8}$ M to $10^{-13}$ M or from $10^{-9}$M to $10^{-13}$ M).

In one embodiment, Kd is measured by a radiolabeled antigen binding assay (MA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v)

bovine serum albumin in PBS for two to five hours at room temperature (approximately 23° C.). In a non-adsorbent plate (Nunc #269620), 100 μM or 26 μM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with, e.g., immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($K_{on}$) and dissociation rates ($K_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., J. Mol. Biol. 293:865-881 (1999). If the on-rate exceeds 106 M−1 s−1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette. Other coupling chemistries for the target antigen to the chip surface (e.g., streptavidin/biotin, hydrophobic interaction, or disulfide chemistry) are also readily available instead of the amine coupling methodology (CM5 chip) described above, as will be understood by one of ordinary skill in the art.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al, Nature, 256: 495 (1975); Harlow et al, Antibodies: A Laboratory Manual, (Cold Spring Harbor Laboratory Press, 2nd ed. 1988); Hammerling et al., in: Monoclonal Antibodies and T-Cell Hybridomas pp. 563-681 (Elsevier, N.Y., 1981)), recombinant DNA methods (see, e.g., U.S. Pat. No. 4,816,567), phage display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995). The above patents, publications, and references are incorporated by reference in their entirety.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23: 1035-1038 (1995); Hurle and Gross, Curr. Op. Biotech. 5:428-433 (1994). The foregoing references are incorporated by reference in their entirety.

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., J. Mol. Biol, 222: 581-597 (1991) and Hoogenboom et al., Nucl. Acids Res., 19: 4133-4137 (1991)); using human myeloma and mouse-human heteromyeloma cell lines for the production of human monoclonal antibodies (see, e.g., Kozbor, J. Immunol, 133: 3001 (1984); Brodeur et al., Monoclonal Antibody Production Techniques and Applications, pp. 55-93 (Marcel Dekker, Inc., New York, 1987); and Boerner et al., J. Immunol, 147: 86 (1991)); and generating monoclonal antibodies in transgenic animals (e.g., mice) that are capable of producing a full repertoire of human antibodies in the absence of endogenous immunoglobulin production (see, e.g., Jakobovits et al., Proc. Natl. Acad. Sci USA, 90: 2551 (1993); Jakobovits et al., Nature, 362: 255 (1993); Bruggermann et al., Year in Immunol., 7: 33 (1993)). This definition of a human antibody specifically excludes a humanized antibody comprising antigen-binding residues from a non-human animal.

All known types of such antibodies are within the scope of the invention. Exemplary antibodies include those that bind to growth factors, cytokines, lymphokines, cell surface receptors, enzymes, vascular endothelial growth factors, fibroblast growth factors, and antibodies to their respective receptors. Other exemplary antibodies include monoclonal antibodies directed to receptor-IgG Fc fusion proteins, and glycoproteins. Any modified (e.g., mutated) version of any of the above listed polypeptides is also within the scope of the invention. Therapeutic compounds to be used in the invention are known in the art and are disclosed by way of example in U.S. Pat. No. 7,608,681, incorporated herein by reference in its entirety. Additionally, the invention contemplates conjugates of inhibitors or antagonists of naturally-occurring or non-naturally occurring antibodies in a subject that cause autoimmune diseases or undesirable inflammatory conditions.

In one embodiment, the drug is a DNA molecule, an RNA molecule, an aptamer (single-stranded or double-stranded), DNA or RNA oligonucleotides, larger DNA molecules that are linear or circular, oligonucleotides that are used for RNA interference (RNAi), variations of DNA such as substitution of DNA/RNA hybrid molecules, synthetic DNA-like molecules such as PNA or other nucleic acid derivative molecules (see WO07/035922, incorporated by reference herein in its entirety). In another embodiment, the therapeutic compound is composed of nuclease-resistant DNA or RNA oligonucleotides. In a preferred embodiment, nuclease-resistant DNA oligonucleotides are Morpholinos, (i.e. phosphorodiamidate analogs of nucleic acids that bind to nucleic acids in a sequence-specific manner, Sarepta Therapeutics, Cambridge Mass.).

In other embodiments, RNAi conjugated to the vitamin D carriers of the invention are used to treat both inherited and infectious diseases. In preferred embodiments, the conjugates are used to treat, for example, blood conditions, liver conditions, cardiovascular conditions, hepatitis, eye conditions, metabolic conditions, graft rejections, cancer, autoimmune conditions, amyloidosis, and nervous system conditions.

In another embodiment, the drug is a small molecule or chemical entity. In another embodiment, the drug is a peptide or a derivative of a peptide such as a PNA. In another embodiment, the drug is a protein comprised of all or part of a polypeptide, whether full-length or a fragment or truncated version, whether PEGylated, glycosylated or otherwise covalently or noncovalently modified or left unmodified.

Some aspects of the assembly of carriers utilizes chemical methods that are well-known in the art. For example, Vitamin E-PEG is manufactured by Eastman Chemical, Biotin-PEG is manufactured by many PEG manufacturers such as Enzon, Nektar and NOF Corporation. Methods of producing PEG molecules with some vitamins and other therapeutic compounds linked to them follow these and other chemical methods known in the art. The attachment of PEG to an oligonucleotide or related molecule occurs, for example, as the PEG2-N-hydroxysuccinimide ester coupled to the oligonucleotide through the 5' amine moiety. Several coupling methods are contemplated and include, for example, NHS coupling to amine groups such as a lysine residue on a peptide, maleimide coupling to sulfhydryl group such as on a cysteine residue, iodoacetyl coupling to a sulfhydryl group, pyridyldithiol coupling to a sulfhydryl group, hydrazide for coupling to a carbohydrate group, aldehyde for coupling to the N-terminus, or tetrafluorophenyl ester coupling that is known to react with primary or secondary amines. Other possible chemical coupling methods are known to those skilled in the art and can be substituted. By way of example, conjugation using the coupling groups of the invention may be carried out using the compositions and methods described in WO93/012145 (Atassi et al.) and also see U.S. Pat. No. 7,803,777 (Defrees et al.), incorporated by reference herein in their entirety.

Exemplary drug formulations of the invention include aqueous solutions, organic solutions, powder formulations, solid formulations and a mixed phase formulations.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts retain the desired biological activity of the therapeutic composition without toxic side effects. Examples of such salts are (a) acid addition salts formed with inorganic acids, for example, hydrochloric acid, hydrobromic acid, sulfuric acid, phosphoric acid, nitric acid and the like/and salts formed with organic acids such as, for example, acetic acid, trifluoroacetic acid, tartaric acid, succinic acid, maleic acid, fumaric acid, gluconic acid, citric acid, malic acid, ascorbic acid, benzoic acid, tanic acid, pamoic acid, alginic acid, polyglutamic acid, naphthalenesulfonic acid, naphthalene disulfonic acid, polygalacturonic acid and the like; (b) base addition salts or complexes formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethlenediamine; or (c) combinations of (a) and (b), e.g. a zinc tannate salt and the like.

The pharmaceutical compositions of this invention may be administered by subcutaneous, transdermal, oral, parenteral, inhalation, ocular, topical, rectal, nasal, buccal (including sublingual), vaginal, or implanted reservoir modes. The pharmaceutical compositions of this invention may contain any conventional, non-toxic, pharmaceutically-acceptable carriers, adjuvants or vehicles. The term parenteral as used herein includes subcutaneous, intracutaneous, intravenous, intramuscular, intraarticular, intrasynovial, intrasternal, intrathecal, intralesional, and intracranial injection or infusion techniques.

Also contemplated, in some embodiments, are pharmaceutical compositions comprising as an active ingredient, therapeutic compounds described herein, or pharmaceutically acceptable salt thereof, in a mixture with a pharmaceutically acceptable, non-toxic component. As mentioned above, such compositions may be prepared for parenteral administration, particularly in the form of liquid solutions or suspensions; for oral or buccal administration, particularly in the form of tablets or capsules; for intranasal administration, particularly in the form of powders, nasal drops, evaporating solutions or aerosols; for inhalation, particularly in the form of liquid solutions or dry powders with excipients, defined broadly; for transdermal administration, particularly in the form of a skin patch or microneedle patch; and for rectal or vaginal administration, particularly in the form of a suppository.

The compositions may conveniently be administered in unit dosage form and may be prepared by any of the methods well-known in the pharmaceutical art, for example, as described in Remington's Pharmaceutical Sciences, 17th ed., Mack Publishing Co., Easton, Pa. (1985), incorporated herein by reference in its entirety. Formulations for parenteral administration may contain as excipients sterile water or saline alkylene glycols such as propylene glycol, polyalkylene glycols such as polyethylene glycol, saccharides, oils of vegetable origin, hydrogenated napthalenes, serum albumin or other nanoparticles (as used in Abraxane™, American Pharmaceutical Partners, Inc. Schaumburg, Ill.), and the like. For oral administration, the formulation can be enhanced by the addition of bile salts or acylcarnitines. Formulations for nasal administration may be solid or solutions in evaporating solvents such as hydrofluorocarbons, and may contain excipients for stabilization, for example, saccharides, surfactants, submicron anhydrous alpha-lactose or dextran, or may be aqueous or oily solutions for use in the form of nasal drops or metered spray. For buccal administration, typical excipients include sugars, calcium stearate, magnesium stearate, pregelatinated starch, and the like.

Delivery of modified therapeutic compounds described herein to a subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, polymeric hydrogels, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

In certain embodiments for transdermal administration, delivery across the barrier of the skin would be enhanced using electrodes (e.g. iontophoresis), electroporation, or the application of short, high-voltage electrical pulses to the skin, radiofrequencies, ultrasound (e.g. sonophoresis), microprojections (e.g. microneedles), jet injectors, thermal ablation, magnetophoresis, lasers, velocity, or photomechanical waves. The drug can be included in single-layer drug-in-adhesive, multi-layer drug-in-adhesive, reservoir, matrix, or vapor style patches, or could utilize patchless technology. Delivery across the barrier of the skin could also be enhanced using encapsulation, a skin lipid fluidizer, or a hollow or solid microstructured transdermal system (MTS, such as that manufactured by 3M), jet injectors. Additives to the formulation to aid in the passage of therapeutic compounds through the skin include prodrugs, chemicals, surfactants, cell penetrating peptides, permeation enhancers, encapsulation technologies, enzymes, enzyme inhibitors, gels, nanoparticles and peptide or protein chaperones.

One form of controlled-release formulation contains the therapeutic compound or its salt dispersed or encapsulated in a slowly degrading, non-toxic, non-antigenic polymer such as copoly(lactic/glycolic) acid, as described in the pioneering work of Kent et al., U.S. Pat. No. 4,675,189, incorporated by reference herein. The compounds, or their salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J R Robinson ed., Marcel Dekker Inc., New York, 1978; and Controlled Release of Biologically Active Agents, R W Baker, John Wiley & Sons, New York, 1987. The foregoing are incorporated by reference in their entirety.

An additional form of controlled-release formulation comprises a solution of biodegradable polymer, such as copoly(lactic/glycolic acid) or block copolymers of lactic acid and PEG, is a bioacceptable solvent, which is injected subcutaneously or intramuscularly to achieve a depot formulation. Mixing of the therapeutic compounds described herein with such a polymeric formulation is suitable to achieve very long duration of action formulations.

When formulated for nasal administration, the absorption across the nasal mucous membrane may be further enhanced by surfactants, such as, for example, glycocholic acid, cholic acid, taurocholic acid, ethocholic acid, deoxycholic acid, chenodeoxycholic acid, dehdryocholic acid, glycodeoxycholic acid, cycledextrins and the like in an amount in the range of between about 0.1 and 15 weight percent, between about 0.5 and 4 weight percent, or about 2 weight percent. An additional class of absorption enhancers reported to exhibit greater efficacy with decreased irritation is the class of alkyl maltosides, such as tetradecylmaltoside (Arnold, J J et al., 2004, J Pharm Sci 93: 2205-13; Ahsan, F et al., 2001, Pharm Res 18:1742-46) and references therein, all of which are hereby incorporated by reference.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient that is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topical transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When formulated for delivery by inhalation, a number of formulations offer advantages. Adsorption of the therapeutic compound to readily dispersed solids such as diketopiperazines (for example, Technosphere particles (Pfutzner, A and Forst, T, 2005, Expert Opin Drug Deliv 2:1097-1106) or similar structures gives a formulation that results in rapid initial uptake of the therapeutic compound. Lyophilized powders, especially glassy particles, containing the therapeutic compound and an excipient are useful for delivery to the lung with good bioavailability, for example, see Exubera® (inhaled insulin, Pfizer, Inc. and Aventis Pharmaceuticals Inc.) and Afrezza® (inhaled insulin, Mannkind, Corp.).

Dosage levels of between about 0.01 and about 100 mg/kg body weight per day, preferably 0.5 and about 50 mg/kg body weight per day of the active ingredient compound are useful in the prevention and treatment of disease. Such administration can be used as a chronic or acute therapy. The amount of drug that may be combined with the carrier to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, gender, diet, time of administration, rate of excretion, drug combination, the severity and course of an infection, the patient's disposition to the infection and the judgment of the treating physician.

The carrier-drug conjugates described herein provide advantages to drug manufacturers and patients over unmodified drugs. Specifically, the carrier-drug conjugate or formulation will be a more potent, longer lasting, and require smaller and less frequent dosing. This translates into lowered healthcare costs and more convenient drug administration schedules for patients. The carrier-drug conjugates can also provide subcutaneous or transdermal routes of administration as alternatives to intravenous injection. These routes can be self-administered by patients and thus improve patient compliance.

In yet another aspect of the invention, the levels of DBP can be increased as part of the carrier-drug therapy. It has been reported that estrogen can increase DBP levels (Speeckaert et al., Clinica Chimica Acta 371:33). It is contemplated here that levels of DBP can be increased by administration of estrogen for more effective delivery of carrier-drug conjugates.

In yet another aspect of the invention, it is contemplated that the carrier can be used to deliver drugs transdermally. Since DBP normally transports UV activated vitamin D at locations close to the surface of the skin, the use of a transdermal delivery system with the carrier becomes feasible.

In order that the invention described herein may be more fully understood, the following examples are set forth. It should be understood that these examples are for illustrative purposes only and are not to be construed as limiting this invention in any manner. In particular, the compositions and methods disclosed herein function with all non-hormonal forms of vitamin D, including homologs, analogs, and metabolites thereof. This includes vitamin D as used in the examples below.

EXAMPLES

Example 1: Preparation Exemplary Carriers for Coupling Therapeutic Compounds to Non-Hormonal Vitamin D at the C25 Position Exemplary carriers were prepared containing vitamin D and 2 kDa PEG scaffolds. One exemplary carrier was thiol-reactive and comprised vitamin D-PEG with a maleimide reactive group at the C25 position (herein referred to as Vitamin D-(25)-PEG$_{2k}$-maleimide or VitD-(25)-PEG$_{2k}$-maleimide).

Another exemplary carrier was amine-reactive and comprised vitamin D-PEG with an NETS-reactive group. These reagents were prepared as described in WO2013172967 (Soliman et al.), incorporated herein by reference in its entirety.

Example 2: Preparation of an Exemplary Amino-Terminal Reactive Carrier for Coupling Therapeutic Compounds to Non-Hormonal Vitamin D at the C3 Position An exemplary amino-terminal reactive carrier was prepared containing an aldehyde reactive group connected to the C3 position of vitamin D and a 2 kDa PEG scaffold (herein referred to as Vitamin D-(3)-PEG$_{2k}$-aldehyde or VitD-(3)-PEG$_{2k}$-maleimide). The aldehyde on the carrier in this example was used to conjugate to a free amino-terminus on the proteins and peptides disclosed in the examples below. The synthesis is outlined in FIG. 1.

Briefly, (S,Z)-3-((E)-2-((1R,3aS,7aR)-1-((R)-6-hydroxy-6-methylheptan-2-yl)-7a-methylhexahydro-1H-inden-4(2H)-ylidene)ethylidene)-4-methylenecyclohexanol (compound Va, 20 mg, 0.049 mmol, 1 equiv., purchased from Toronto Research Chemicals, catalog number C125700, also known as calcifediol and 25-hydroxyvitamin D) was dissolved in a mixture of anhydrous tert-butanol and acetonitrile (10:1, 1 mL), cooled to 4° C. Acrylonitrile (26.6 mg, 0.5 mmol, 10 equiv.) was added to it followed by Triton B, 40% aqueous solution, 10 µL). The mixture was stirred at 4° C. for 2.5 h. The reaction was quenched with cold 2% HCl (10 mL), the aqueous phase was extracted with ether (2×10 mL), dried (MgSO$_4$) and evaporated to obtain the crude product. This material was purified by flash chromatography (TLC, silica gel, 50% ethyl acetate in hexanes) with 5-20% EtOAc/hexanes as eluent to isolate the desired product, 3-(((S,Z)-3-((E)-2-((1R,3aS,7aR)-1-((R)-6-hydroxy-6-methylheptan-2-yl)-7a-methylhexahydro-1H-inden-4(2H)-ylidene)ethylidene)-4-methylenecyclohexyl)oxy)propanenitrile, compound V (15 mg, 68%) as a white solid (R$_f$ 0.2 silica gel, 40% EtOAc in hexanes). NMR analysis did not show any appreciable amount of solvents.

To a solution of aluminum chloride (66 mg, 0.495 mmol) in anhydrous ether (2 mL) at 0° C. under argon was added a solution of lithium aluminum hydride (1M in ether, 19 mg, 0.5 mL, 0.5 mmol) dropwise. The mixture was stirred for 5 min., a solution of compound Vc (15 mg, 0.033 mmol) in ether (3 mL) was added to it dropwise, the reaction mixture was stirred at 0° C. for 5 min and then at room temperature for 1 h. The reaction was monitored by MS and TLC (silica gel, 10% MeOH/CHCl$_3$/0.1% NH$_4$OH). Ethyl acetate (1 mL) and water (1 mL) were added to the reaction mixture followed by 5% NaOH (5 mL). The organic phase was separated, and the aqueous phase was extracted with ethyl acetate (5 mL) and ether (5 mL). The combined organic phases were washed with brine (5 mL), dried (Na$_2$SO$_4$) and evaporated on a rotavap to afford the desired amine, (R)-6-((1R,3aS,7aR,E)-4-((Z)-2-((S)-5-(3-aminopropoxy)-2-methylenecyclohexylidene)ethylidene)-7a-methyloctahydro-1H-inden-1-yl)-2-methylheptan-2-ol, compound Vd (12.5 mg, 82%) as a pale yellow oil. R$_f$ 0.2 (silica gel, 20% MeOH/DCM/0.2% NH$_4$OH). The NMR analysis revealed the presence ~8% of ethyl acetate.

Compound Vd (12.5 mg, 0.0273 mmol, 1 equiv.), compound Ve (hydroxyl PEG NHS ester, MW 2000 with n≅45 where n is the number of repeating CH$_2$CH$_2$O units, Jenkem Technology USA #A-5076, 43 mg, 0.0216 mmol, 0.8 equiv.) were dissolved in anhydrous dichloromethane (0.1 mL). Triethylamine (12 mg, 16 µl, 0.11 mmol, 4 equiv.) was added and the reaction mixture was stirred for 20 h at room temperature under nitrogen. The sample was dried under a stream of nitrogen to afford the crude compound Vf, which was purified by flash chromatography using 5-10% MeOH/dichloromethane as eluent to isolate the desired product Vf as a white foam (30 mg, 38%). R$_f$ 0.4 (silica gel, 10% methanol in dichloromethane). $^1$H NMR analysis of the isolated material confirmed its identity and purity.

To a solution of compound Vf (30 mg, 0.0123 mmol, 1 equiv.), tetrapropylammonium perruthenate (1.0 mg, 0.00284, 0.23 equiv.) and N-methylmorpholine-N-Oxide (4.3 mg, 0.0369 mmol, 3 equiv.) in 2 mL of dry dichloromethane was added powdered 4A° molecular sieves (500 mg) and the reaction mixture was flushed with N$_2$. The reaction flask was covered with aluminum foil to avoid light and it was stirred at room temperature for 36 h. Since the R$_f$ of both starting material and product is same on TLC (silicagel, 10% MeOH/dichloromethane), formation of the product was confirmed by examining the $^1$H NMR of an aliquot. The reaction mixture was filtered through the pad of Celite in a pipette with dichloromethane (15 mL) and N$_2$ pressure. The combined organics were concentrated under a flow of N$_2$ and dried on high vacuum for 2 h to get 35 mg (100%) of the crude product TLC(R$_f$: 0.3, 10% MeOH/dichloromethane, staining with PMA). A second run of reaction under the exactly same conditions yielded another 35 mg of the product. $^1$H NMR of the product from both batches is same and hence combined to get 70 mg of compound V, VitD-(3)-PEG$_{2k}$-aldehyde.

Example 3: Preparation of an Exemplary Thiol-Reactive Carrier for Coupling Therapeutic Compounds to Non-Hormonal Vitamin D at the C3 Position An exemplary thiol-reactive carrier comprising vitamin D with a maleimide reactive group connected to the C3 position of vitamin D (VitD-(3)-PEG$_{2k}$-maleimide) was prepared. The maleimide on the carrier in this example was used to conjugate to a free thiol on the protein and peptide in the examples below. The synthesis is outlined in FIG. 2.

Briefly, compound Vd (23 mg, 0.05 mmol, 1 equiv.) prepared as in Example 2, compound VIa (Creative Pegworks cat. # PHB-956, MAL-PEG-COOH, 2 k with n=45 where n is the number of repeating CH$_2$CH$_2$O units, 79 mg, 0.0395 mmol, 0.8 equiv.) and 2-chloro-1-methylpyridinium iodide (32 mg, 0.125 mmol, 2.5 equiv.) were dissolved in anhydrous dichloromethane (1 mL). Triethylamine (20.4 mg, 28 µl, 0.2 mmol, 4 equiv.) was added and the reaction mixture was stirred for 4 h at room temperature under nitrogen. The reaction mixture was diluted with dichloromethane (20 mL), washed with 5% aqueous citric acid (20 mL), saturated aqueous sodium bicarbonate (20 mL), and brine (20 mL). The organic layer was dried over anhydrous sodium sulfate, filtered and concentrated at 30° C. The sample was purified by silica gel (10 g) flash chromatography. The column was eluted with 1-10% MeOH/dichloromethane. Fractions containing pure product were combined together and evaporated on a rotavap, while maintaining the temperature at 30° C. The sample was dried under a stream of nitrogen to afford compound VI, VitD- (3)-PEG$_{2K}$-maleimide as a brown gum (58 mg, 48%) (R$_f$ 0.25, silica gel, 10% methanol in dichloromethane). $^1$H NMR analysis of the isolated material confirmed its identity and purity.

Figure 3:
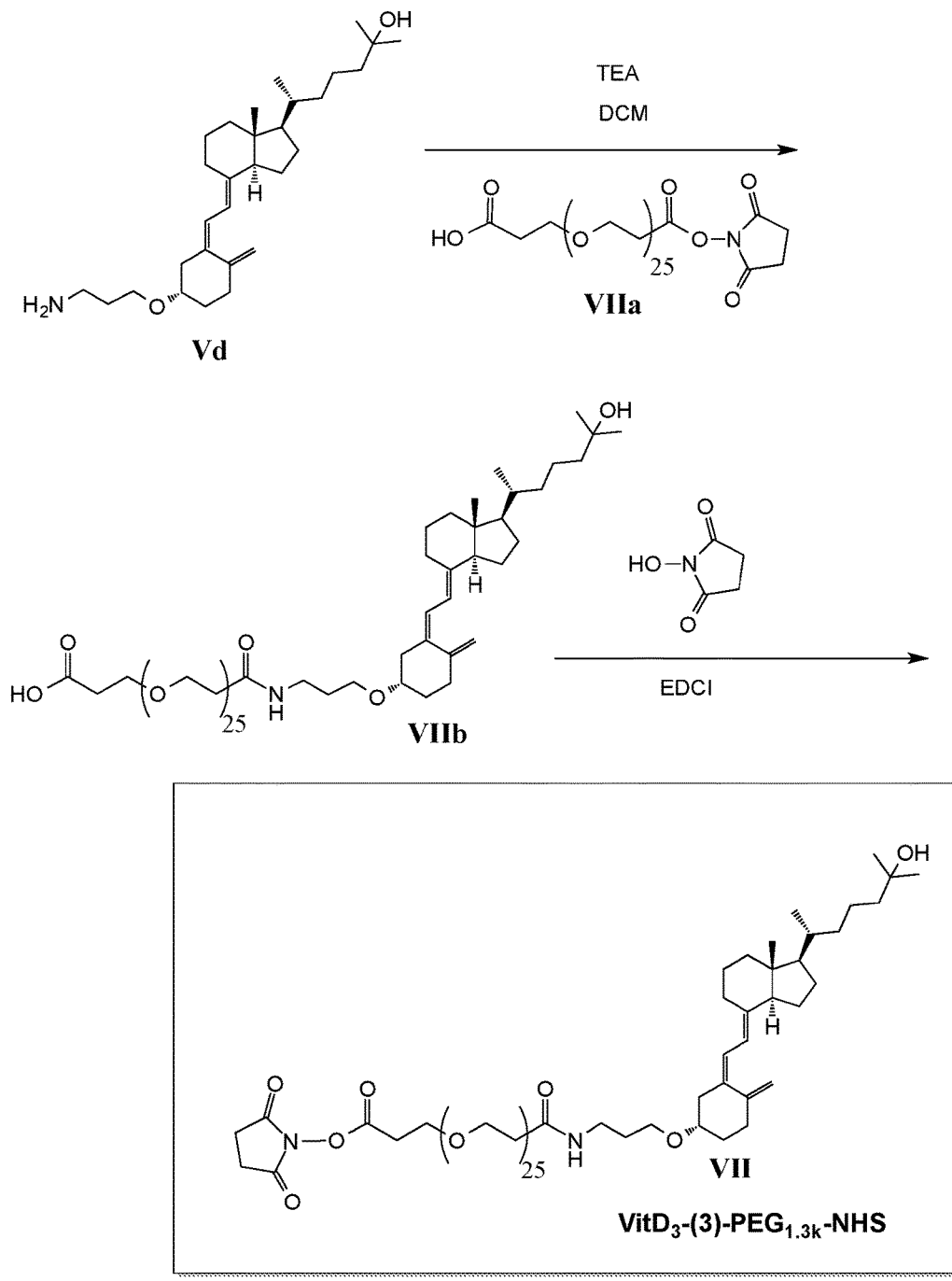
FIG. 3: Reaction scheme showing the chemical structure and syntheses used to generate a carrier, a Vitamin D-(3)-PEG$_{1.3K}$-NHS adduct. The carrier was generated by conjugating 1) a vitamin D analog, 2) a PEG scaffold, and 3) an NHS coupling group.

Example 4: Preparation of an Exemplary Amine-Reactive Carrier for Coupling Therapeutic Compounds to Non-Hormonal Vitamin D at the C3 Position An exemplary amine-reactive carrier comprising vitamin D with an NHS reactive group connected to the C3 position of vitamin D (Herein referred to as Vitamin D-(3)-PEG$_{1.3K}$-NHS or VitD-(3)-PEG$_{1.3K}$-NHS) was prepared. The NHS on the carrier in this example was used to conjugate to a free thiol on the protein and peptide in the examples below. The synthesis is outlined in FIG. 3.

Briefly, compound Vd (20 mg, 0.044 mmol, 1 equiv.) and compound VIIa (Quanta Biodesign cat. #10140, with n=25 where n is the number of repeating CH$_2$CH$_2$O units, 44 mg, 0.0346 mmol, 0.8 equiv.) were dissolved in anhydrous dichloromethane (1 mL). Triethylamine (22.0 mg, 31 µl, 0.22 mmol, 5 equiv.) was added and the reaction mixture was stirred for 24 h at room temperature under nitrogen. The reaction mixture was diluted with dichloromethane (20 mL), washed with 5% aqueous citric acid (20 mL), and brine (20 mL). The organic layer was dried over anhydrous sodium sulfate, filtered and concentrated while maintaining the temperature at 30° C. The sample was purified by silica gel (10 g) flash chromatography. The column was eluted with 1-10% MeOH/dichloromethane. Fractions containing pure product were combined together and evaporated on a rotavap, while maintaining the temperature below 30° C. The sample was dried under a stream of nitrogen to afford compound VIIb as a brown gum (33 mg, 56%) (R$_f$ 0.20, silica gel, 10% methanol in dichloromethane). $^1$H NMR analysis of the isolated material confirmed its identity.

Compound VIIb (31 mg, 0.018 mmol, 1 equiv.), N-hydroxysuccinimide (6.3 mg, 0.055 mmol, 3 equiv.), and EDCI (8.6 mg, 0.045 mmol, 2.5 eq.) were dissolved in anhydrous THF (2 mL). Triethylamine (7.4 mg, 10 µL, 0.073 mmol, 4 equiv.) was added and the reaction mixture was stirred for 24 h at room temperature under nitrogen. The reaction mixture was diluted with dichloromethane (20 mL) and washed with 5% aqueous citric acid (20 mL), and brine (20 mL). The organic layer was dried over anhydrous sodium sulfate, filtered and concentrated while maintaining the temperature at 30° C. The sample was dried under a stream of nitrogen to afford compound VII, VitD-(3)-PEG$_{2K}$-NHS, as a brown gum (38.6 mg, >100%) (R$_f$ 0.25, silica gel, 10% methanol in dichloromethane). $^1$H NMR analysis of the isolated material confirmed its identity and purity.

Example 5: Preparation and Characterization of Apelin Conjugated to Non-Hormonal Vitamin D In this example, apelin conjugated to the VitD-(25)-PEG$_{2K}$-maleimide carrier generated in Example 1 and the VitD-(3)-PEG$_{2K}$-aldehyde generated in Example 2 to apelin imparted a significantly longer half-life for apelin. The resulting conjugated molecule may be a useful therapeutic for the treatment of heart disease, pulmonary hypertension (e.g. pulmonary arterial hypertension or pulmonary venous hypertension), other cardiovascular diseases, or diabetes.

Synthesis of VitD-(25)-PEG$_{2K}$-C-Apelin

An apelin-13 derivative with a N-terminal cysteine residue (C-apelin) was synthesized by Biopeptek, Inc. (Malvern, Pa., SEQ ID NO:16). Conjugation with the carrier was accomplished by mixing a thiol-reactive moiety [VitD-(25)-PEG$_{2K}$-maleimide from Example 1] dissolved in DMSO at 5 mg/mL with the apelin peptide containing a free cysteine at a concentration of 5 mg/mL in PBS buffer with 1 mM EDTA in a molar ratio of 1.4:1 carrier to peptide. The reaction was allowed to proceed for 1 hour at room temperature. The conjugated peptide, VitD-(25)-PEG$_{2K}$-apelin, was separated from unreacted components by ion exchange chromatography. Conjugation and purity was confirmed by SDS-PAGE. The conjugates were then buffer exchanged to PBS and filter sterilized using a 0.22 micron filter for use in the animal study.

Synthesis of VitD-(3)-PEG$_{2K}$-Apelin:

The apelin-13 peptide was purchased from Bachem (Torrance, Calif., Cat. NO. H-4566). Conjugation between the aldehyde on the carrier and an amine moiety on the peptide was carried out at low pH in order to favor reaction with the N-terminal amine of the peptide. The amine-reactive carrier [Vitamin D-(3)-PEG$_{2K}$-aldehyde from Example 2] dissolved in DMSO at 5 mg/mL was mixed with the apelin peptide at a concentration of 5 mg/mL in dH$_2$O in a molar ratio of 3:1 carrier to peptide with a final concentration of 50 mM NaOAc pH=5 and 25 mM NaCNBH$_3$. The reaction was allowed to proceed overnight at 4° C. The conjugated peptide, VitD-(3)-PEG$_{2K}$-apelin, was separated from unreacted components by ion exchange chromatography. Conjugation and purity was confirmed by SDS-PAGE.

Figure 4:
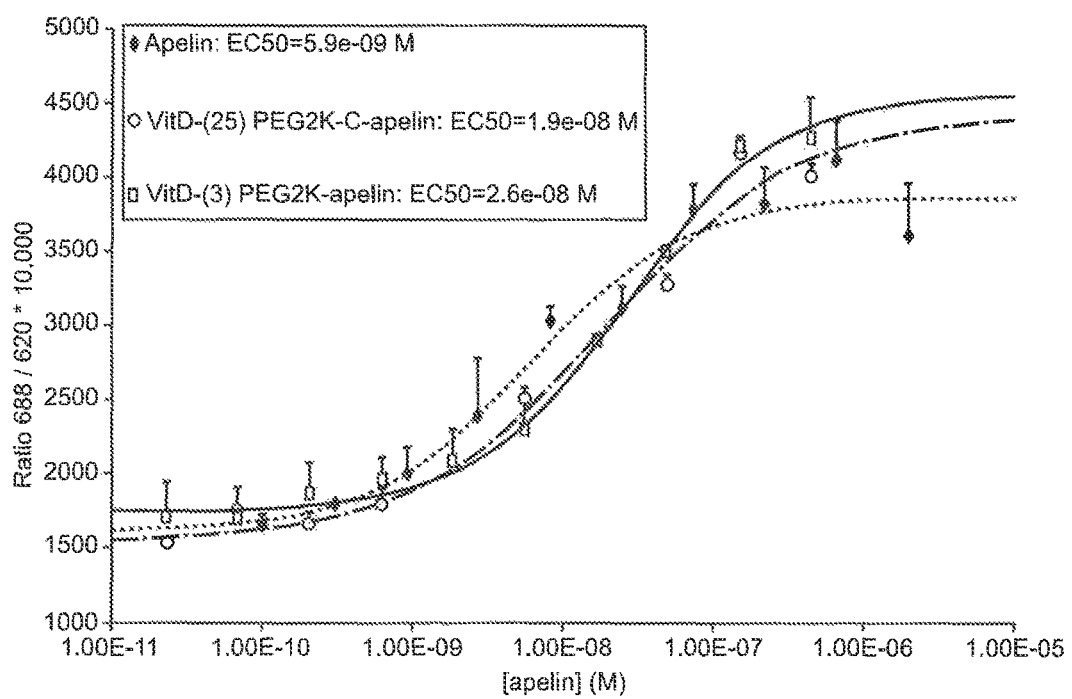
FIG. 4: Functional apelin assay measuring inhibition of forskolin-stimulated cAMP production in HEK293T cells expressing the APJ receptor. Apelin-13, Vitamin D-(25)-PEG$_{2K}$-C-apelin, and Vitamin D-(3)-PEG$_{2K}$-apelin were tested. The functional activity of apelin (EC$_{50}$) was determined from a four parameter logistic function fit of the curve.

Activity of Apelin Constructs in Cell-Based APJ Receptor Assay:

Unmodified apelin-13, VitD-(25)-PEG$_{2K}$-C-apelin, and VitD-(3)-PEG$_{2K}$-apelin were submitted to Multispan, Inc. (Hayward, Calif.) for determination of bioactivity. Multispan's functional apelin assay uses HEK293T cells expressing the receptor for apelin, APJ (Multispan catalog #: C1196). The assay measures apelin inhibition of forskolin-stimulated cAMP production. A comparison of the functional activity of apelin with the two modified peptides is shown in FIG. 4. The curves were fit with a four parameter logistic function in order to determine the EC$_{50}$ values. The EC$_{50}$ value for apelin was approximately 6 nM, with the modified apelin derivatives being 3-4 fold higher, within the observed error for this experiment. Thus, unmodified and modified apelin have substantially the same activity.

Figure 5:
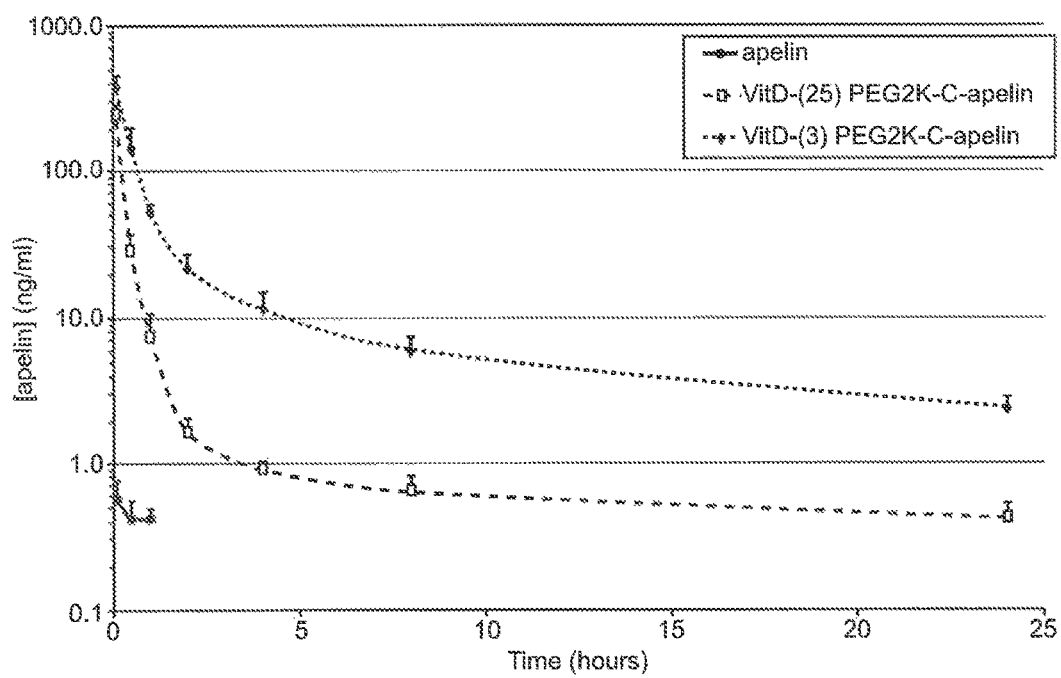
FIG. 5: Pharmacokinetics of apelin and apelin conjugates. Apelin alone or conjugated to the Vitamin D-(25)-PEG$_{2K}$-maleimide carrier, or the Vitamin D-(3)-PEG$_{2K}$-aldehyde carrier were injected intravenously into Sprague-Dawley rats at 0.1 mg/kg. Plasma samples were analyzed for apelin concentration by ELISA in duplicate and the average value from three animals were plotted on the semi-log graph.

Pharmacokinetic Properties of Apelin and Apelin Conjugates:

Four groups of four rats each were injected intravenously with apelin-13, VitD-(25)-PEG$_{2K}$-C-apelin, or Vitamin D-(3)-PEG$_{2K}$-apelin at 0.1 mg/kg. Plasma samples were taken at 5 min, and 0.5, 1, 2, 4, 8 and 24 hr and analyzed for the presence of apelin by quantitative ELISA (Phoenix Pharmaceuticals, Burlingame, Calif., Cat. No. EK-057-23). The apelin conjugates showed dramatically improved pharmacokinetic profiles when compared to unmodified apelin (FIG. 5). Unmodified apelin decayed to near-background levels within 5 minutes of injection. VitD-(25)-PEG$_{2K}$-C-apelin showed improved pharmacokinetic properties when compared to unmodified apelin. Surprisingly, however, VitD-(3)-PEG$_{2K}$-apelin showed significantly improved pharmacokinetic properties when compared to the other apelin molecules, including VitD-(25)-PEG$_{2K}$-C-apelin. This demonstrated that conjugation of the carrier to the C3 position of vitamin D provides further improvement to conjugation at the C25 position.

The decay rates of the carrier-conjugates are complex and probably represent a combination of slower renal clearance and protection from protease degradation. A pharmacokinetic analysis of the data was then performed using WinNonLin (PharSight) and GraphPad (Prism). Importantly, the AUC of the native apelin-13 peptide was 0.4 ng*hr/mL, Vitamin D-(25)-PEG$_{2K}$-apelin was 85 ng*hr/mL, and Vitamin D-(3)-PEG$_{2K}$ was 328 ng*hr/mL. Therefore, the bioavailability improvements of the C25 and C3 carriers were 213-fold and 820-fold, respectively.

Example 6: Preparation and Characterization of Ghrelin Conjugated to Non-Hormonal Vitamin D Synthetic ghrelin peptides are listed in Table 1A. Wild type (wt) peptides were purchased from Bachem [Torrence, Calif., Catalog # H-4864 (human) and H-4862 (rat)], and custom sequences were synthesized by Biopeptek (Malvern, Pa.). Custom sequences include peptides where the octanoylated serine (Oct-S, also known as O-octanoyl-serine) at position three is replaced by octanoylated 2,3-diaminopropionic acid (Oct-Dap, also known as Nβ☐octanoyl-2,3-diaminopropionic acid), tyrosine (Y), or tryptophan (W).

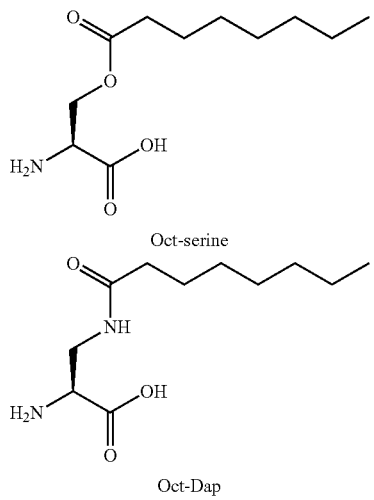

Oct-serine

Oct-Dap

Oct-S is rapidly deacylated in vivo by esterases; the deacylated form of ghrelin no longer activates the GHS-R receptor. The Oct-Dap, tryptophan, and tyrosine derivatives should maintain their activity since they are not subject to deacetylation by esterases. The vitamin D-PEG-maleimide carrier, as described in Examples 1 and 3, was selected to be proportional in size to a 2-3 kDa peptide so that conjugation might not significantly affect the bioactivity. Conjugation with the carrier was accomplished by mixing a thiol-reactive moiety [VitD-(25)-PEG$_{2K}$-maleimide from Example 1, or compound VI: VitD-(3)-PEG$_{2K}$-maleimide from Example 3, or PEG$_{2K}$-maleimide from Sigma-Aldrich #731765, also known as poly(ethylene glycol) methyl ether maleimide] dissolved in DMSO at 5 mg/mL with the ghrelin peptide containing a free cysteine at a concentration of 5 mg/mL in PBS buffer with 1 mM EDTA in a molar ratio of 1.4:1 carrier to peptide. The reaction was allowed to proceed for 1 hour at room temperature. The conjugated peptide was separated from unreacted components by ion exchange chromatography. Conjugation and purity was confirmed by SDS-PAGE. Rat ghrelin peptides (rGhrelin), human ghrelin peptides (hGhrelin) and the ghrelin-carrier conjugates were then buffer exchanged to PBS and filter sterilized using a 0.22 micron filter for use in the animal study.

TABLE 1A

| Name | Sequence | Species | SEQ. ID |
|---|---|---|---|
| wt Oct-hGhrelin | GS(Oct-S)FLSPEHQRVQQRKESKKPPAKLQPR | human | 2 |
| Oct-hGhrelin-C | GS(Oct-S)FLSPEHQRVQQRKESKKPPAKLQPRC | human | 3 |
| Dap-hGhrelin-C | GSS(Oct-Dap)FLSPEHQRVQQRKESKKPPAKLQPRC | human | 4 |
| GSY-hGhrelin-C | GSYFLSPEHQRVQQRKESKKPPAKLQPRC | human | 5 |
| wt Oct-rGhrelin | GS(Oct-S)FLSPEHQKAQQPKESKKPPAKLQPR | rat | 6 |
| Oct-rGhrelin-C | GS(Oct-S)FLSPEHQKAQQPKESKKPPAKLQPRC | rat | 7 |
| Dap-rGhrelin-C | GS(Oct-Dap)FLSPEHQKAQQPKESKKPPAKLQPRC | rat | 8 |
| GSW-rGhrelin | GSWFLSPEHQKAQQPKESKKPPAKLQPRC | rat | 9 |

Pharmacokinetics of Ghrelin Conjugates

The pharmacokinetics of ghrelin conjugates were examined in Sprague Dawley rats. The conjugates were: wt Oct-hGhrelin and Oct-hGhrelin-C conjugated to VitD-(25)-PEG$_{2K}$-maleimide; Dap-hGhrelin-C conjugated to either VitD-(25)-PEG$_{2K}$-maleimide or compound VI: VitD-(3)-PEG$_{2K}$-maleimide from Example 3; and PEG$_{2K}$-maleimide. Briefly, 0.1 mg/kg of each molecule was injected separately into the rats by intravenous (iv) or subcutaneous (sc) injection. Samples of plasma were collected at 5 mins (iv only), 30 mins, 1 hr, 2 hrs, 4 hrs, 8 hrs, and 24 hrs. Protease inhibitors and HCl (final concentration 0.05 N) were added to the plasma samples, which were then immediately frozen. Samples were analyzed using commercial ELISA kits validated for analyzing either total rGhrelin (acylated+nonacylated) or active rGhrelin (acylated only) from rat plasma (Millipore, Cat. #EZRGRT-91K and #EZRGRA-90K). The results show significant differences in the pharmacokinetic profiles of hGhrelin and the hGhrelin-carrier conjugates (FIGS. 6-8).

FIG. 6A shows that the pharmacokinetic profile of intravenously-injected ghrelin was improved when conjugated to vitamin D at the C25 and C3 positions. Active and total ghrelin levels were analyzed because the Oct-Dap modification protected the protein from deacylation, whereas the native Oct-Ser containing peptides were rapidly deacylated. Wt-Oct-hGhrelin alone or conjugated to the VitD-(25)-PEG$_{2k}$-maleimide carrier, as well as Dap-hGhrelin conjugated to either the VitD-(25)-PEG$_{2k}$-maleimide carrier or the VitD-(3)-PEG$_{2k}$-maleimide carrier were injected intravenously into Sprague-Dawley rats at 0.1 mg/kg. Ghrelin concentrations in plasma samples were analyzed by ELISA for either total ghrelin (acylated+non-acylated) or active ghrelin (acylated only) in duplicate. The average value from three animals was plotted on the semi-log graph. The octanoylated Dap residue was resistant to degradation.

Both the C25 and C3 conjugates showed significant improvements in the pharmacokinetic profiles. The C3 conjugate, however, showed the best pharmacokinetic profile. Compared to unmodified wt Oct-hGhrelin, the PEG$_{2K}$-(25)-VitD carrier provided significant half-life extension to both Oct-hGhrelin-C and Dap-hGhrelin, although the former is rapidly deacylated to its inactive form. The PEG$_{2K}$-(3)-VitD carrier provided even more half-life extension when compared to the PEG$_{2K}$-(25)-VitD carrier.

Figure 7:
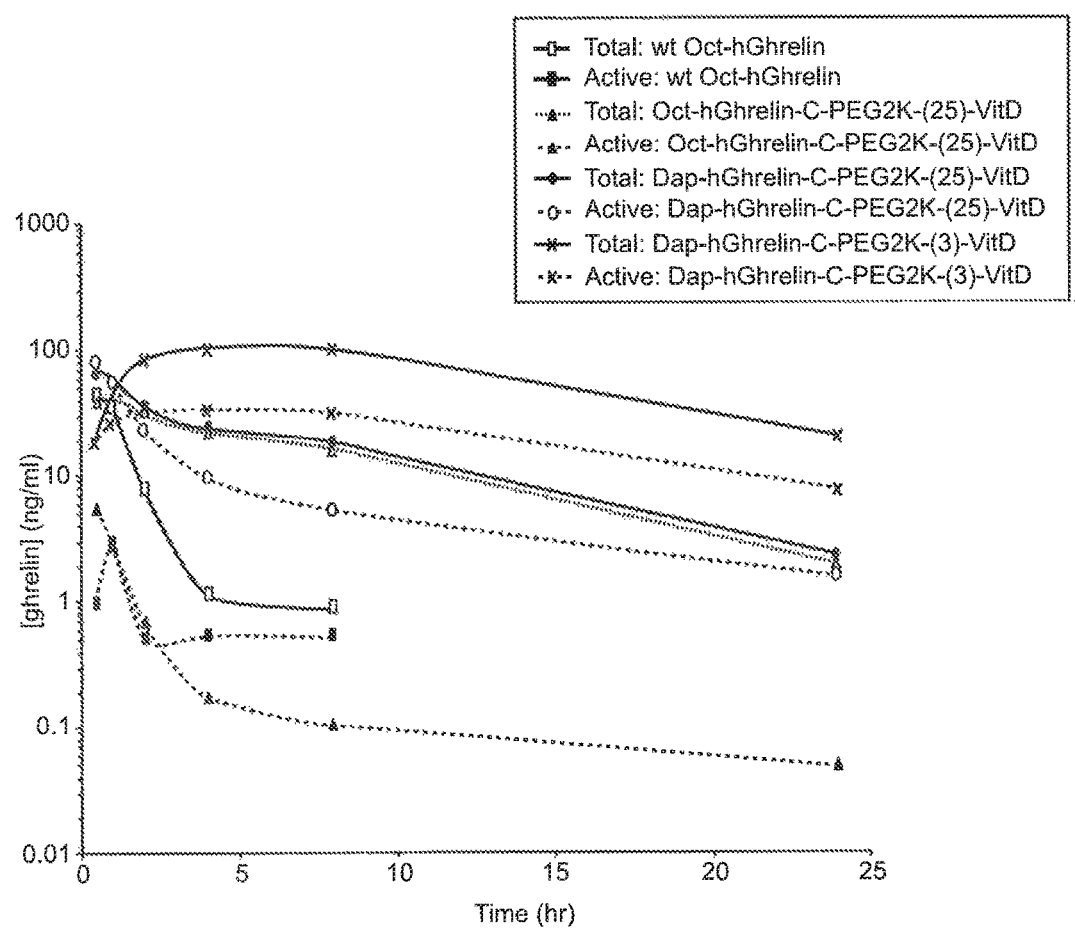
FIG. 7: Pharmacokinetics and bioavailability of total (solid lines) and active (dashed lines) ghrelin and ghrelin conjugates delivered by subcutaneous injection. Conjugation to the Vitamin D-(25)-PEG$_{2k}$-maleimide carrier and the Vitamin D-(3)-PEG$_{2k}$-maleimide carrier showed significant improvements over the unconjugated ghrelin. The Vitamin D-(3)-PEG$_{2k}$-maleimide carrier, however, showed superior bioavailability and pharmacokinetic properties compared to the Vitamin D-(25)-PEG$_{2k}$-maleimide carrier.
Figure 8:
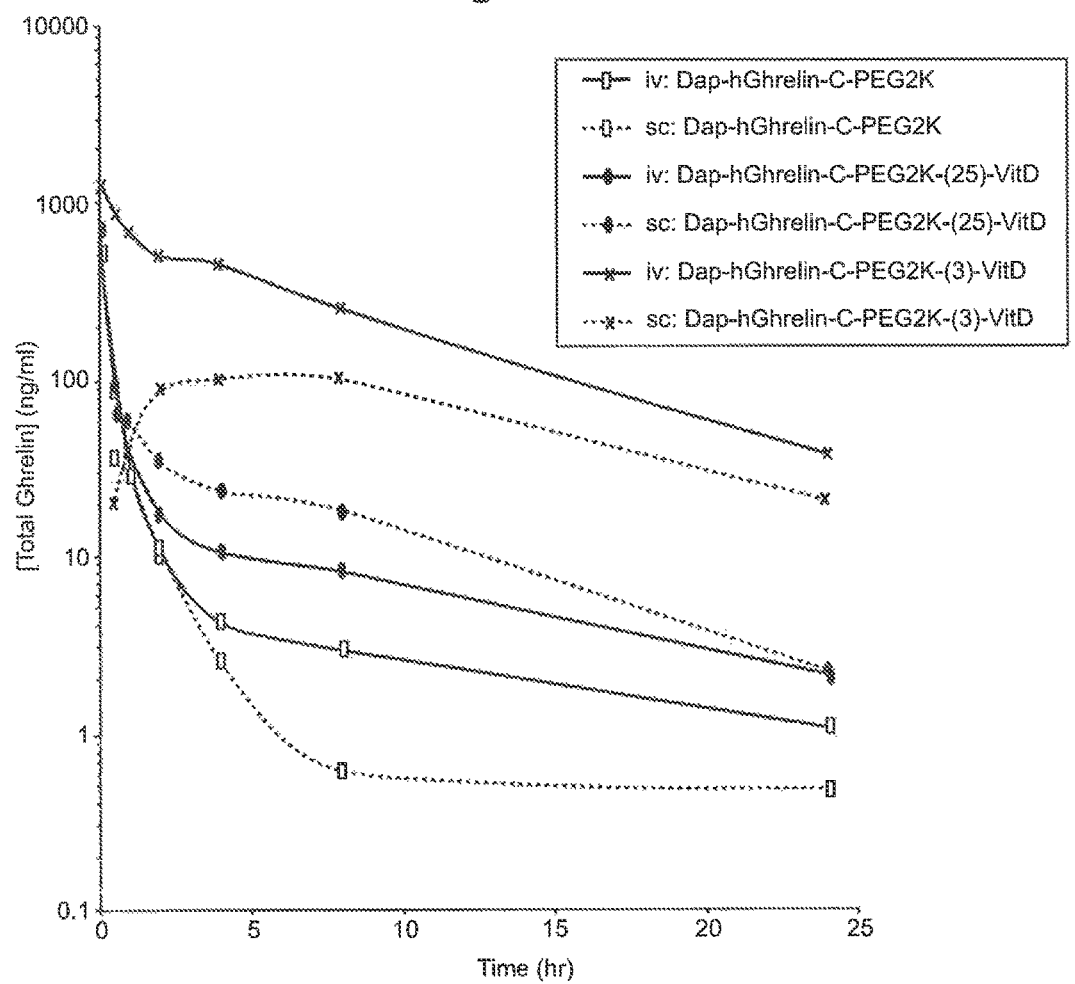
FIG. 8: Pharmacokinetic profiles of intravenous (solid lines) and subcutaneous (dashed lines) injections of ghrelin conjugated to PEG$_{2k}$ alone or with Vitamin D-(25)-PEG$_{2k}$-maleimide carrier and the Vitamin D-(3)-PEG$_{2k}$-maleimide carrier.

FIG. 7 compares active and total ghrelin levels subcutaneously injected into rats. It demonstrates that the PEG$_{2K}$-(25)-VitD and PEG$_{2K}$-(3)-VitD carriers provided significant half-life extension and improvements in bioavailability. The carrier modified at the C3 position of vitamin D was superior. The Oct-Dap modification provided resistance to deacylation, however, some degree of deacylation occurred following subcutaneous injection that was not observed with intravenous delivery.

FIG. 8 compares the pharmacokinetic profiles for Dap-hGhrelin-C conjugated to PEG$_{2k}$-maleimide, VitD-(25)-PEG$_{2k}$-maleimide, and VitD-(3)-PEG$_{2k}$-maleimide carrier. The samples were injected either intravenously or subcutaneously. Plasma samples were analyzed for total Ghrelin (acylated+non-acylated) levels by ELISA. While both the C25 and C3 conjugates showed significant improvement over the PEGylated ghrelin, the C3 conjugate showed the most improved bioavailability and pharmacokinetic properties. The 2 kDa PEG scaffold alone had some half-life extending properties for intravenously-injected ghrelin. It was ineffective, however, for modifying the pharmacokinetic properties of subcutaneously-injected ghrelin. In contrast, modification of ghrelin with PEG$_{2K}$-(25)-VitD or PEG$_{2K}$-(3)-VitD carrier resulted in significantly longer half-lives upon intravenous injection. Additionally, bioavailability was improved following subcutaneous injection. The carrier modified at the C3 position of vitamin D was superior to the carrier modified at the C25 position.

Assessment of the Receptor Binding Activity of a Ghrelin Peptide-Carrier

In some embodiments, the activity of the ghrelin peptide, when conjugated to a carrier, are substantially the same as unmodified peptides. Ghrelin and VitD-PEG-ghrelin were compared for receptor binding and activation of a ghrelin receptor using a cell-based receptor agonist assay: HEK293T cells stably expressing human ghrelin receptor (GHS-R, Multispan Cat. No. C1197b) were monitored for increased intracellular calcium upon exposure to the test compounds using the Screen Quest™ Fluo-8 No Wash kit (AAT Bioquest, Cat. No. 36315) on a FLIPR 384 instrument (Molecular Devices, Cat. Nos. FLIPR and 0200-6072). EC$_{50}$ values for unconjugated and conjugated ghrelin were determined and compared. The EC$_{50}$ value for rGhrelin was 1.9 nM. The EC$_{50}$ value for Dap-rGhrelin-C-PEG$_{2k}$-(3)-VitD was 20.5 nM. The EC$_{50}$ value for GSW-rGhrelin-C-PEG$_{2k}$-(3)-VitD was 3.9 nM. Thus, conjugation of ghrelin to vitamin D resulted in substantially the same receptor activity as the unmodified ghrelin peptide.

Pharmacokinetics of Ghrelin Conjugates with Multiple Dosing

The long-term pharmacokinetic profiles of two ghrelin conjugates, Dap-rGhrelin-C-PEG$_{2k}$-(3)-VitD and GSW-rGhrelin-C-PEG$_{2k}$-(3)-VitD, were compared to unmodified wt Oct-rGhrelin at various doses. Each dose was delivered by two subcutaneous injections separated by 48 hrs with blood collection as follows: t=0 (before first dose), 0.5, 1, 2, 4, 8, 24, 32, 48 (before second dose), 48.5, 49, 50, 52, 56, 72, 80, and 96 hours. The doses examined were 5 and 0.5 mg/kg (wt Oct-rGhrelin), 0.5 and 0.1 mg/kg (Dap-rGhrelin-C-PEG$_{2k}$-(3)-VitD, and 0.5 and 0.1 mg/kg (GSW-rGhrelin-C-PEG$_{2k}$-(3)-VitD). Pefabloc SC (Sigma-Aldrich Cat#76309) was added to collected plasma samples at 1 mg/ml and the plasma was immediately frozen until the levels of ghrelin were analyzed using a rat/mouse ghrelin (total) ELISA kit (Millipore, Cat. #EZRGRT-91K). Both carrier-modified ghrelin conjugates show greatly improved pharmacokinetic profiles compared to unmodified ghrelin (FIG. 6B). At the highest dose of ghrelin conjugates (0.5 mg/kg), measurable levels of the conjugates were observed 72 hours after the second injection, whereas the same dose of unmodified ghrelin returned to baseline levels within 6 hrs. The concentration profiles as a function of time for 0-48 hours were analyzed with Kinetica software (ThermoFisher) using an extravascular, non-compartmental analysis. Area under the curve (AUC) was calculated using the trapezoidal (linear rule) method. Results for the 0.5 mg/kg doses are given in Table 1B. The conjugates achieved higher peak concentrations (Cmax) and possessed slower elimination times than unmodified ghrelin leading to large increases in the calculated AUC (30-50 fold). Calculated t$_{1/2}$ values increased from 0.6 hours to around 10 hours with the VitD-(3) carrier, a 17-fold improvement.

TABLE 1B

| Compound | Dose (mg/kg) | C$_{max}$ (ng/ml) | T$_{max}$ (hr) | AUC hr*(mg/ml) | t$_{1/2}$ (hr) | MRT (hr) |
|---|---|---|---|---|---|---|
| wt Oct-rGhrelin | 0.5 | 319 | 0.5 | 373 | 0.59 | 1.06 |
| Dap-rGhrelin-C-PEG$_{2k}$-(3)-VitD | 0.5 | 1096 | 4 | 19,332 | 9.57 | 13.64 |
| GSW-rGhrelin-C-PEG$_{2k}$-(3)-VitD | 0.5 | 547 | 4 | 10,921 | 10.26 | 15.05 |

Ghrelin Conjugates for Treating Cachexia and Other Weight Loss Conditions

As an animal model of cancer cachexia, rats were implanted with Yoshida AH130 ascites hepatoma cells. After implantation of the tumor cells, a long-lived ghrelin conjugate, Dap-rGhrelin-C-PEG$_{2k}$-(3)-VitD, was delivered either every day, or every other day, at various doses. Unmodified ghrelin was delivered by constant infusion via a subcutaneous osmotic pump. Dap-rGhrelin-C-PEG$_{2k}$-(3)-VitD was also compared to similar subcutaneous doses of ghrelin and Oct-rGhrelin-C-PEG$_{2k}$-(3)-VitD (a long-lived but not constitutively active ghrelin). See Table 1C for a complete listing of compound dosing, where "ghrelin"=wt Oct-rGhrelin, "Dap-VitD"=Dap-rGhrelin-C-PEG$_{2k}$-(3)-VitD, and "Oct-VitD"=Oct-rGhrelin-C-PEG$_{2k}$-(3)-VitD.

TABLE 1C

| Group | N | Tumor | Agent | Dose (mg/kg) | Route | Schedule |
|---|---|---|---|---|---|---|
| 1 | 10 | None | vehicle | — | sc | qd to end |
| 2 | 10 | None | Dap-VitD | 0.1 | sc | qd to end |
| 3 | 10 | Yes | vehicle | — | sc | qd to end |

TABLE 1C-continued

| Group | N | Tumor | Agent | Dose (mg/kg) | Route | Schedule |
|---|---|---|---|---|---|---|
| 4 | 10 | Yes | Ghrelin | 1.25/day | sc osmotic pump | 6 days of infusion |
| 5 | 10 | Yes | Ghrelin | 0.1 | sc | qd to end |
| 6 | 10 | Yes | Ghrelin | 0.5 | sc | qd to end |
| 7 | 10 | Yes | Oct-VitD | 0.1 | sc | qd to end |
| 8 | 10 | Yes | Dap-VitD | 0.1 | sc | qd to end |
| 9 | 10 | Yes | Dap-VitD | 0.5 | sc | qod to end (days 1, 3, 5) |

Nine week old female Wistar rats (Crl:WI, Charles River Labs.) with a body weight (BW) range of 185.1-266.3 g, on Day 1 were used. Yoshida AH-130 rat hepatoma cells were propagated in vivo in the rats. On the day of the first inoculation, the hepatoma cells were thawed, washed to remove freezing medium, resuspended in PBS, and injected intraperitoneally (ip) into each rat. For subsequent in vivo passages, hepatoma cells were harvested from the ascites fluid during log phase growth and resuspended in phosphate-buffered saline (PBS) at $2 \times 10^7$ cells/mL. On Day 0, animals in Groups 3-9 (n=10/group) each received an ip injection of 0.2 mL of the cell suspension. Groups 1 and 2 were not inoculated.

On Day 1, rats were placed into nine groups of ten animals and were treated in accordance with the protocol in Table 1C. Doses for Groups 1-3 and 5-8 were delivered subcutaneously (sc), every day (qd). Doses for Group 4 were delivered via subcutaneous osmotic pump (Model 2001, 1 µl/hr). Doses for Group 9 were delivered every other day (qod). Groups 1 and 3 received vehicle, Groups 2 and 8 received Dap-VitD at 0.1 mg/kg, and Group 9 received Dap-VitD at 0.5 mg/kg. Group 4 received ghrelin at 1.25 mg/kg/day via s.c. osmotic pump, and Groups 5 and 6 received ghrelin at 0.1 and 0.5 mg/kg. Group 7 received Oct-VitD at 0.1 mg/kg. All doses for Groups 1-3 and 5-9 were delivered in a dose volume of 1 mL/kg and were dosed to the individual body weight of each animal. Body weight (BW) was recorded for each animal on Days 1-6. The significance of differences among the means of the normalized bodyweight values for the treatment groups was determined by using an unpaired t-test (GraphPad). In tumor-inoculated groups, when an animal presented with less than 1.0 mL of ascites fluid, engraftment failure was assumed and the data for that animal was not used.

Figure 9:
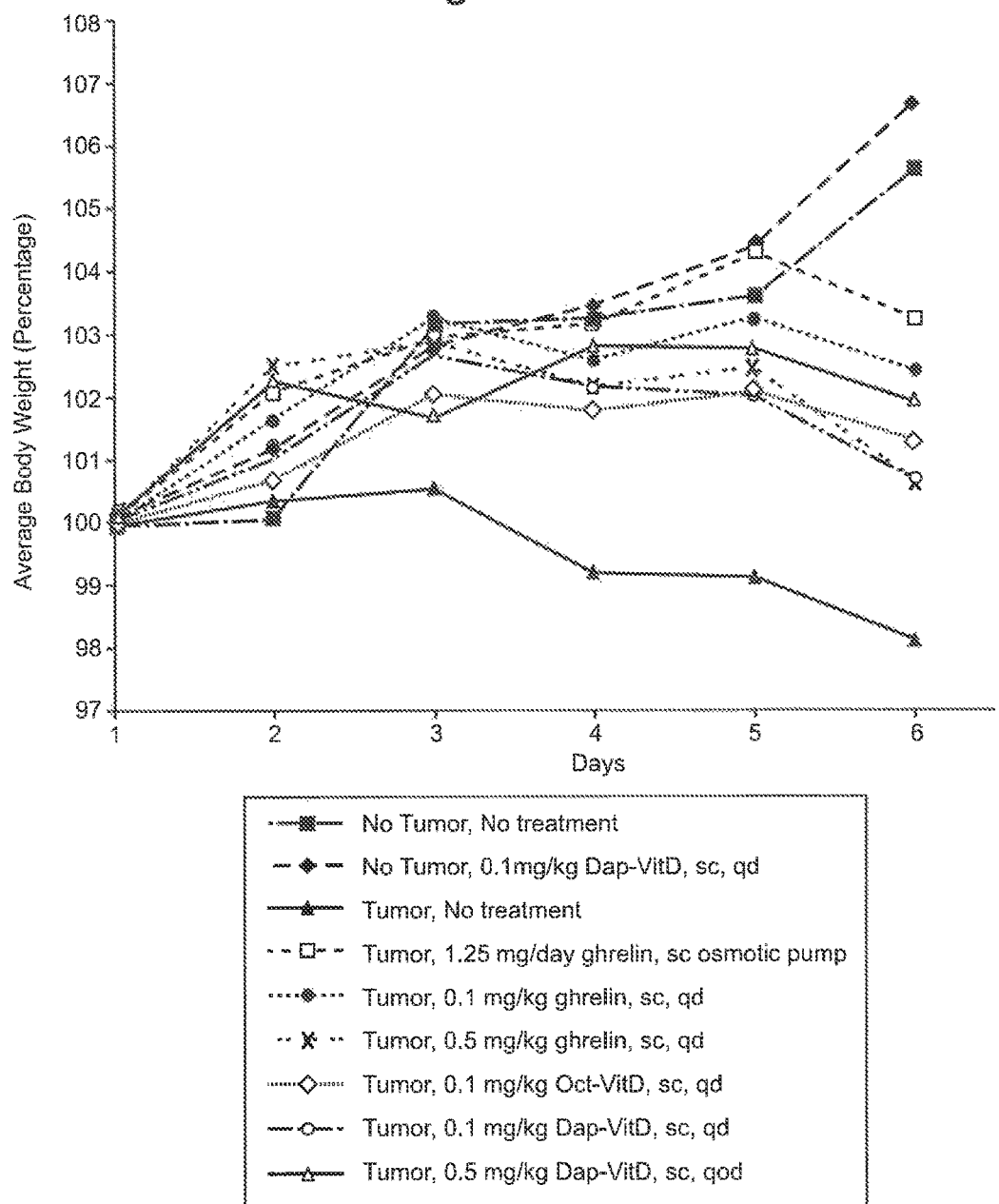
FIG. 9: Ghrelin and ghrelin conjugates of the Vitamin D-(3)-PEG$_{2k}$-maleimide carrier treatment reverses body weight loss in rats bearing Yoshida AH130 ascites hepatoma cells as a model of cancer cachexia.

The change in body weight during the course of treatment is shown in FIG. 9. It shows a plot of average body weight for each group (n=7-10) normalized to 100 percent on Day 1. The untreated group with implanted tumors (Group 3) lost body weight over the course of six days. In contrast, all of the treated groups with tumors (Groups 4-9) displayed increased body weight approaching that of healthy animals without tumors (Groups 1 and 2). On Day 4, the average body weight of each group was statistically different than Group 3 (p≤0.05 vs. Group 3). On Day 4, of all the groups bearing tumors, the group that received a constant infusion of ghrelin (Group 4) had the highest weight, followed closely by the group receiving Dap-rGhrelin-C-PEG$_{2K}$-(3)-VitD every other day by subcutaneous injection (Group 9).

These data show that ghrelin conjugated to vitamin D can effectively increase the body weight in subjects. This can be used to reverse the wasting effects of cachexia and other weight loss disorders. The superior pharmacokinetic profiles provided by the vitamin D carriers provide for more flexibility in dosing times and amounts.

Example 7: Preparation of Insulin Coupled to Non-Hormonal Vitamin D at the C25 and C3 Positions In this example, the VitD-(25)-PEG$_{2k}$-NHS was conjugated to human insulin comprising the A chain (SEQ ID NO:11) and B chain (SEQ ID NO:12) to prepare a therapeutic for treating diabetes. The insulin A chain contains a cys6-cys11 intra-chain disulfide linkage. The cys7 on the A chain is linked to cys7 of the B chain by an inter-chain disulfide linkage. The cys20 on the A chain is linked to cys19 of the B chain, also by an interchain disulfide linkage. Insulin (Sigma Aldrich, St. Louis, Mo., Catalog #12643) was resuspended in a 1:1 mixture of DMSO and 1M HEPES+0.85% NaCl, pH=8 at a concentration of 5 mg/ml. VitD-(25)-PEG$_{2k}$-NHS carrier dissolved in DMSO at a concentration of 5 mg/ml 1.4 to 4 molar equivalents relative to insulin was added. The final concentration of insulin was brought to 1 mg/ml in dH$_2$O and the reaction was allowed to proceed for 1 hour at room temperature. The insulin conjugates were confirmed by SDS-PAGE.

In this example, the VitD-(3)-PEG$_{1.3k}$-NHS is conjugated to human insulin to prepare a therapeutic for treating diabetes. Insulin (Sigma Aldrich, St. Louis, Mo., Catalog #12643) is resuspended in a 1:1 mixture of DMSO and 1M HEPES+0.85% NaCl, pH=8 at a concentration of 5 mg/ml. VitD-(3)-PEG$_{1.3k}$-NHS carrier is dissolved in DMSO at a concentration of 5 mg/ml 1.4 to 4 molar equivalents relative to insulin was added. The final concentration of insulin is brought to 1 mg/ml in dH$_2$O and the reaction is allowed to proceed for 1 hour at room temperature. The insulin conjugates are confirmed by SDS-PAGE.

Pharmacokinetic experiments, in vitro bioactivity assays measuring the uptake of glucose by adipocytes, and evaluation in vivo of the blood glucose lowering ability in diabetic rat models are performed as described in EP2085406, incorporated herein by reference in its entirety.

Example 8: Preparation of PTH Coupled to Non-Hormonal Vitamin D at the C3 Position and the C25 Position The VitD-(3)-PEG$_{2K}$-maleimide carrier (Compound VI from Example 3), the VitD-(3)-PEG$_{2K}$-aldehyde (Compound V from Example 2), and the VitD-(25)-PEG$_{2K}$-maleimide carrier (from Example 1), were conjugated to PTH in order to extend the half-life of PTH, thereby making the conjugated molecule a potentially useful therapeutic for the treatment of hypoparathyroidism and osteoporosis.

Synthesis of PTH-C-PEG$_{2K}$-(3)-VitD

A PTH derivative with a C-terminal cysteine residue was synthesized by Biopeptek, Inc. (Malvern, Pa., SEQ ID NO:17). Conjugation with the carrier was accomplished by mixing the thiol-reactive VitD-(3)-PEG$_{2K}$-maleimide carrier (Compound VI from Example 3) dissolved in DMSO at 5 mg/mL with the PTH peptide containing a free cysteine at a concentration of 5 mg/mL in PBS buffer with 1 mM EDTA in a molar ratio of 1.3:1 carrier to peptide. The reaction was allowed to proceed for 100 minutes at room temperature. The conjugated peptide, PTH-C-PEG$_{2K}$-(3)-VitD, was separated from unreacted components by ion exchange chromatography. Conjugation and purity was confirmed by SDS-PAGE. The conjugates were then buffer exchanged to PBS and filter sterilized using a 0.22 micron filter for use in the animal study.

Synthesis of VitD-(3)-PEG$_{2K}$-PTH:

The human PTH(1-34) peptide was purchased from Bachem (Torrance, Calif., Catalog # H-4835, SEQ ID NO:10). Conjugation between the aldehyde on the carrier and an amine moiety on the peptide was carried out at low pH in order to favor reaction with the N-terminal amine of the peptide. The amine-reactive VitD-(3)-PEG$_{2K}$-aldehyde carrier (Compound V from Example 2) dissolved in DMSO at 5 mg/mL was mixed with the PTH(1-34) peptide at a concentration of 5 mg/mL in dH$_2$O in a molar ratio of 3:1 carrier to peptide with a final concentration of 50 mM NaOAc pH=5 and 25 mM NaCNBH$_3$. The reaction was allowed to proceed overnight at 4° C. The conjugated peptide, VitD-(3)-PEG$_{2K}$-PTH, was separated from unreacted components by ion exchange chromatography. Conjugation and purity was confirmed by SDS-PAGE.

Activity of PTH(1-34) Constructs in Cell-Based PTH1 Receptor Assay:

Unmodified PTH(1-34), PTH-C-PEG$_{2K}$-(3)-VitD, and VitD-(3)-PEG$_{2K}$-PTH were submitted to Multispan, Inc. (Hayward, Calif.) for determination of bioactivity. Multispan's functional PTH assay uses mammalian cells expressing the PTH1 receptor (Multispan Catalog #C1301). The assay measures agonist activity using calcium mobilization (Screen Quest™ Fluo-8 No Wash kit, AAT Bioquest catalog #36315) and a cAMP assay (HTRF cAMP HiRange Kit, CisBio catalog #62AM6PEC). A comparison of the functional activity of PTH(1-34) vs the two modified peptides is shown in Table 2. The curves were fit with a four parameter logistic function in order to determine the EC$_{50}$ values. The EC$_{50}$ values for PTH(1-34) and PTH-C-PEG$_{2K}$-(3)-VitD were very similar, while the EC$_{50}$ value for VitD-(3)-PEG$_{2K}$-PTH was approximately 10-20 fold worse. This showed that conjugation to the C-terminus of PTH resulted in substantially the same activity as unmodified PTH(1-34). Conjugation at the N-terminus of PTH, however, interfered with its activity.

TABLE 2

| Compound Calcium | EC$_{50}$ | cAMP EC$_{50}$ |
| --- | --- | --- |
| PTH(1-34) | 18.8 nM | 13.1 pM |
| PTH-C-PEG$_{2K}$-(3)-VitD | 14.0 nM | 18.6 pM |
| VitD-(3)-PEG$_{2K}$-PTH | 126 nM | 380 pM |

Synthesis of VitD-(25)-PEG$_{2K}$-C-PTH

A PTH derivative with a N-terminal cysteine residue was synthesized by Biopeptek, Inc. (Malvern, Pa., SEQ ID NO:18). Conjugation with the carrier was accomplished by mixing the thiol-reactive VitD-(25)-PEG$_{2K}$-maleimide carrier from Example 1 dissolved in DMSO at 5 mg/mL with the PTH peptide containing a free cysteine at a concentration of 5 mg/mL in PBS buffer with 1 mM EDTA in a molar ratio of 1:3:1 carrier to peptide. The reaction was allowed to proceed for 75 minutes at room temperature. The conjugated peptide, VitD-(25)-PEG$_{2K}$-C-PTH, was separated from unreacted components by ion exchange chromatography. Conjugation and purity was confirmed by SDS-PAGE. The conjugates were then buffer exchanged to PBS and filter sterilized using a 0.22 micron filter for use in the animal study.

Synthesis of VitD-(3)-PEG$_{2K}$-C-PTH

A PTH derivative with a N-terminal cysteine residue was synthesized by Biopeptek, Inc. (Malvern, Pa., SEQ ID NO:18). Conjugation with the carrier was accomplished by mixing the thiol-reactive VitD-(3)-PEG$_{2K}$-maleimide carrier (Compound VI from Example 3) dissolved in DMSO at 5 mg/mL with the PTH peptide containing a free cysteine at a concentration of 5 mg/mL in PBS buffer with 1 mM EDTA in a molar ratio of 1.3:1 carrier to peptide. The reaction was allowed to proceed for 75 minutes at room temperature. The conjugated peptide, VitD-(3)-PEG$_{2K}$-C-PTH, was separated from unreacted components by ion exchange chromatography. Conjugation and purity was confirmed by SDS-PAGE. The conjugates were then buffer exchanged to PBS and filter sterilized using a 0.22 micron filter for use in the animal study.

Pharmacokinetics of PTH Conjugates

PTH conjugates show improved pharmacokinetics in Sprague Dawley rats when compared to free PTH. Unmodified PTH(1-34), VitD-(25)-PEG$_{2K}$-C-PTH, and VitD-(3)-PEG$_{2K}$-C-PTH were compared. Briefly, 0.1 mg/kg of each molecule was injected separately into the rats (n=4) by subcutaneous (sc) injection. Samples of plasma were collected at 0 hrs (pre-dose), 0.5, 1, 2, 4, 8, 12, 24, 32, 48, and 56 hours then immediately frozen. Samples were analyzed for human PTH (1-34) by ELISA (Phoenix Pharmaceuticals Cat# EK-055-08). The results show significant differences in the pharmacokinetic profiles of PTH and the PTH-carrier conjugates (FIG. 10).

Figure 10:
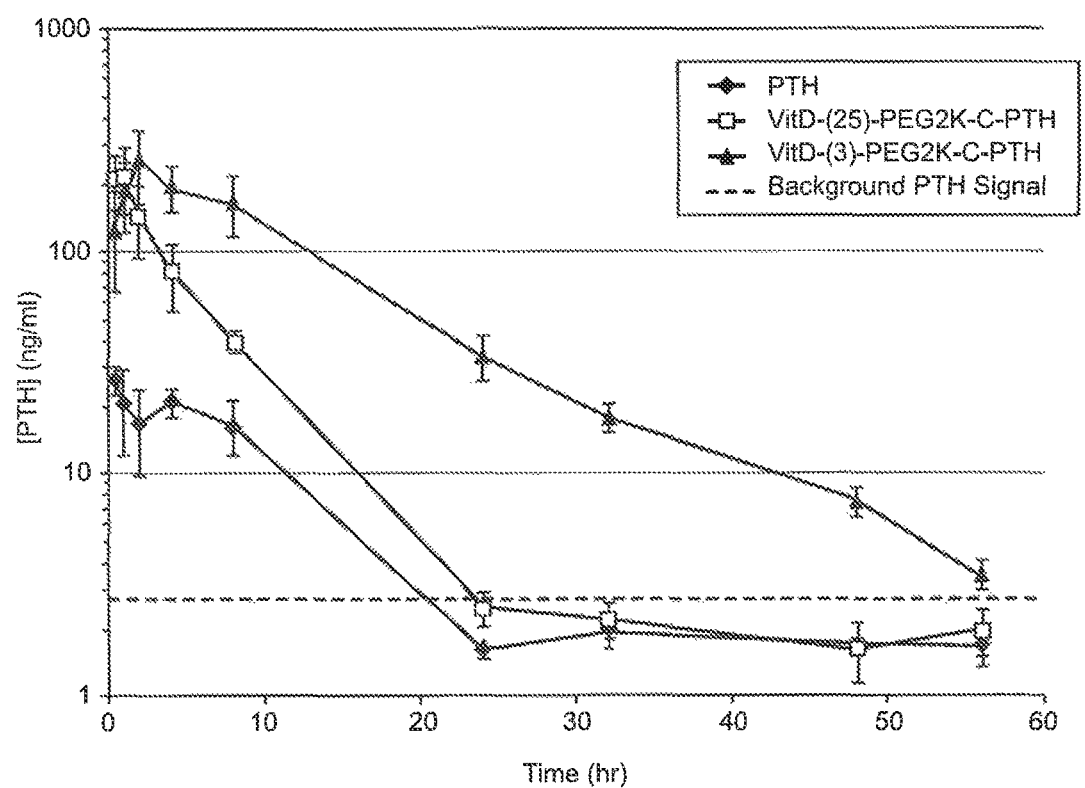
FIG. 10: Vitamin D-(3)-PEG$_{2k}$-PTH and Vitamin D-(25)-PEG$_{2k}$-PTH pharmacokinetics were compared to unmodified PTH(1-34) upon subcutaneous injection in rats.

FIG. 10 shows that the pharmacokinetic profile of subcutaneously-injected PTH was improved when conjugated to vitamin D at the C25 and C3 positions. The best pharmacokinetic profile was obtained, however, with conjugation to the C3 position. Pharmacokinetic parameters were obtained by analyzing the data with Kinetica software (ThermoFisher). Reliable parameters for unmodified PTH could not be obtained due to the poor bioavailability of the wild-type peptide and background PTH signal from endogenous rat PTH. The half-life of PTH(1-34), however, when dosed subcutaneously in rats has previously been reported to be between 15 and 60 minutes (Frolick, Bone 33: 372-379 (2003) and Satterwhite, Calcif Tissue Int. 87:485-492 (2010)). Therefore, the half-life of 2.2 hr for VitD-(25)-PEG$_{2K}$-C-PTH and 6.9 hr for VitD-(3)-PEG$_{2K}$-C-PTH represent improvements of at least 2- and 7-fold, respectively, compared to unmodified PTH. Likewise, the vitamin D-conjugates show improvements in bioavailability as indicated by the 10-fold higher Cmax values and at least a 5-fold and 15-fold improvement in AUC values for the C25 and C3 conjugates, respectively.

Example 9: Preparation of an Antibody Coupled to Non-Hormonal Vitamin D at the C3 Position In this example, the VitD-(25)-PEG$_{2K}$-NHS carrier (described in WO2013172967) and the VitD-(3)-PEG$_{1.3k}$-NHS carrier (Compound VII) were conjugated to infliximab (Remicade®) in order to extend the half-life and bioavailability of the antibody. Remicade is used to treat Crohn's Disease, rheumatoid arthritis, psoriatic arthritis, ankylosing spondylitis, and plaque psoriasis.

Infliximab (Remicade®), sold as a lyophilized powder with the appropriate salts (Hannah Pharmaceuticals), was resuspended to a concentration of 10 mg/mL with water. VitD-(25)-PEG$_{2K}$-NHS or the VitD-(3)-PEG$_{1.3k}$-NHS carrier was resuspended at a concentration of 10 mg/mL in DMSO. VitD-(3)-PEG$_{1.3k}$-NHS and the infliximab were then mixed at a molar ratio of 5:1, 10:1, or 30:1 carrier to infliximab. A therapeutic compound carrier conjugate of the invention typically has at least 1 and could be between 1-10 carrier molecules individually attached to a therapeutic compound. By using an NHS version of the carrier, more than one carrier can be attached to a therapeutic protein. This can be controlled by altering the molar ratio of carrier to target therapeutic in the reaction. In this example, a target distribution of 1-4 carriers was used. This was confirmed by testing two different molar ratios and examining the resulting conjugates by mass spectrometry. C25 carriers were conjugated to the antibody at a ratio of about between 1-2:1. C3 carriers were conjugated to the antibody at a ratio of about 1:1.

The infliximab and infliximab NHS-carrier conjugates were separated from unconjugated carrier by use of a desalting column with a 40 kDa cutoff (Zeba Spin, Thermo Scientific). MALDI-TOF mass spectrometry was used to calculate the intact mass of infliximab in the reactions. The results show that unmodified infliximab had a mass predominantly of 149 kDa. An average attachment of one to three of the VitD-(25)-$PEG_{2K}$-NHS carrier was attached to the antibodies and one to two of the VitD-(3)-$PEG_{1.3K}$-NHS carrier was attached to the antibodies.

Example 10: Preparation and Characterization of GLP-1 Conjugated to Non-Hormonal Vitamin D Synthetic GLP-1(7-37) peptide (SEQ ID NO: 19, hereafter referred to as GLP-1) was purchased from Bachem (Torrence, Calif., Catalog # H-9560), and GLP-1-C with an additional C-terminal cysteine residue (SEQ ID NO: 20) was custom synthesized by Biopeptek (Malvern, Pa.). It was conjugated to the Vitamin D-PEG-maleimide carrier as described in Examples 1 and 3. Conjugation was accomplished by mixing a thiol-reactive moiety (VitD-(25)-$PEG_{2K}$-maleimide) from Example 1, or compound VI (VitD-(3)-$PEG_{2K}$-maleimide) from Example 3 dissolved in DMSO at 10 mg/mL with the GLP-1-C peptide containing a free cysteine at a concentration of ~1 mg/mL in PBS buffer with 1 mM EDTA in a molar ratio of 1:3:1 carrier to peptide. The reaction was allowed to proceed for 1 hour at room temperature. The conjugated peptide was separated from unreacted components by ion exchange chromatography. Conjugation and purity was confirmed by SDS-PAGE. GLP-1 peptide and the GLP-1-carrier conjugates were then buffer exchanged to PBS.

Assessment of the Receptor Binding Activity of GLP-1 Peptide-Carrier

In some embodiments, the activity of the GLP-1 peptide, when conjugated to a carrier, was about the same as unmodified peptides. GLP-1 and GLP-1-C-$PEG_{2K}$-VitD were compared for receptor binding and activation of GLP1R, the GLP-1 receptor, (agonist activity) using a cell-based receptor agonist assay: PathHunter® cells stably expressing human GLP-1 receptor (GLP1R, DiscoveRx Corp., Fremont, Calif.) were monitored for recruitment of β-Arrestin upon exposure to the test compounds using the PathHunter® Detection reagent cocktail on a PerkinElmer Envision instrument with chemiluminescent signal detection. The $EC_{50}$ value for unconjugated GLP-1 was 0.82 µM. The $EC_{50}$ value for GLP-1-C-$PEG_{2K}$-(25)-VitD was 0.51 µM. The $EC_{50}$ value for GLP-1-C-$PEG_{2K}$-(3)-VitD was 0.52 µM. Thus, conjugation of GLP-1 to vitamin D results in about the same or better receptor activity as the unmodified GLP-1 peptide.

Example 11: Preparation and Characterization of FGF21 Conjugated to Non-Hormonal Vitamin D at the C3 and C25 Positions A modified FGF21 was conjugated to the Vitamin D-PEG-maleimide carrier as described in Examples 1 and 3.

As shown below, the FGF21-carrier composition provided significantly improved pharmacokinetic properties when compared to an unmodified FGF21. While both conjugates showed a significant improvement over the unmodified FGF21, conjugation at the C3 position showed significant improvement over conjugation at the C25 position. Together, this example shows that an FGF21-VitD conjugate is an important therapeutic compound for the treatment of diseases that would benefit from FGF21 treatment, including diabetes.

FGF21 was expressed in E. coli, purified, and conjugated to the carrier as follows. A modified FGF21 with a free cysteine residue near the amino terminus of FGF21 allowed site-specific coupling to the carrier. A 6-His tag (SEQ ID NO: 23) was added for ease of purification. The modified FGF21 coding sequence (SEQ ID NO: 21) was computationally codon optimized for expression in E. coli. The gene was chemically synthesized by DNA2.0 (Menlo Park, Calif.) and cloned into the IP-Free expression vector pD441-SR that contains an IPTG-inducible T5 promoter and a kanamycin resistance gene. The plasmid was transformed into Shuffle® Express Competent E. coli (New England BioLabs Cat. No: C3028H). Cells were grown to mid-log phase at 30° C. and then induced for four hours at 25° C. with 0.1 mM IPTG Cells were harvested, lysed, and the supernatant collected. The FGF21 protein (SEQ ID NO: 22) was purified using immobilized metal affinity chromatography (IMAC) resin and polished by anion exchange chromatography.

Conjugation with the carrier was accomplished by mixing a thiol-reactive moiety VitD-(25)-$PEG_{2K}$-maleimide from Example 1 or compound VI: VitD-(3)-$PEG_{2K}$-maleimide from Example 3. Briefly, the carriers were dissolved in DMSO at 10 mg/mL with the purified FGF21 protein containing a free cysteine in a molar ratio of 3:1 carrier to FGF21. The reaction was allowed to proceed for 1 hour at room temperature. The conjugated peptide was separated from unreacted components by using a Zeba™ spin desalting column, 7K MWCO, according to the manufacturer's protocol (ThermoFisher Scientific Inc., Cat. No. 89882). Conjugation and purity was confirmed by SDS-PAGE. FGF21, VitD-(25)-$PEG_{2K}$-FGF21, and VitD-(3)-$PEG_{2K}$-FGF21 were then buffer exchanged to PBS and filter sterilized using a 0.22 micron filter for use in the animal study.

Assessment of the Receptor Binding Activity of FGF21-Carrier Conjugates

In some embodiments, the activity of the FG21, when conjugated to a carrier, was substantially the same as unmodified protein. FGF21 and the VitD-$PEG_{2K}$-FGF21 conjugates were compared for receptor binding and activation of FGFR1 using a cell-based receptor agonist assay (PathHunter® U2OS FGFR1-β-Klotho Functional Assay, DiscoveRx Corp., Fremont, Calif., Cat. No. 93-0943C3). PathHunter® cells stably express human FGF21 receptor (FGFR1). They were monitored for recruitment of the co-receptor, β-Klotho, following exposure to the test compounds using the PathHunter® Detection reagent cocktail on a PerkinElmer Envision instrument with chemiluminescent signal detection. The $EC_{50}$ value for unconjugated FGF21 was 0.16 µg/ml. The $EC_{50}$ value for VitD-(25)-$PEG_{2K}$-FGF21 was 0.13 µg/ml. The $EC_{50}$ value for VitD-(3)-$PEG_{2K}$-FGF21 was 0.40 µg/ml. Thus, the FGF21 conjugates retained about the same receptor activity as the unmodified FGF21 protein or better.

Pharmacokinetics of FGF21 Conjugates

The pharmacokinetics of FGF21 conjugates in Sprague Dawley rats were determined.

Figure 11:
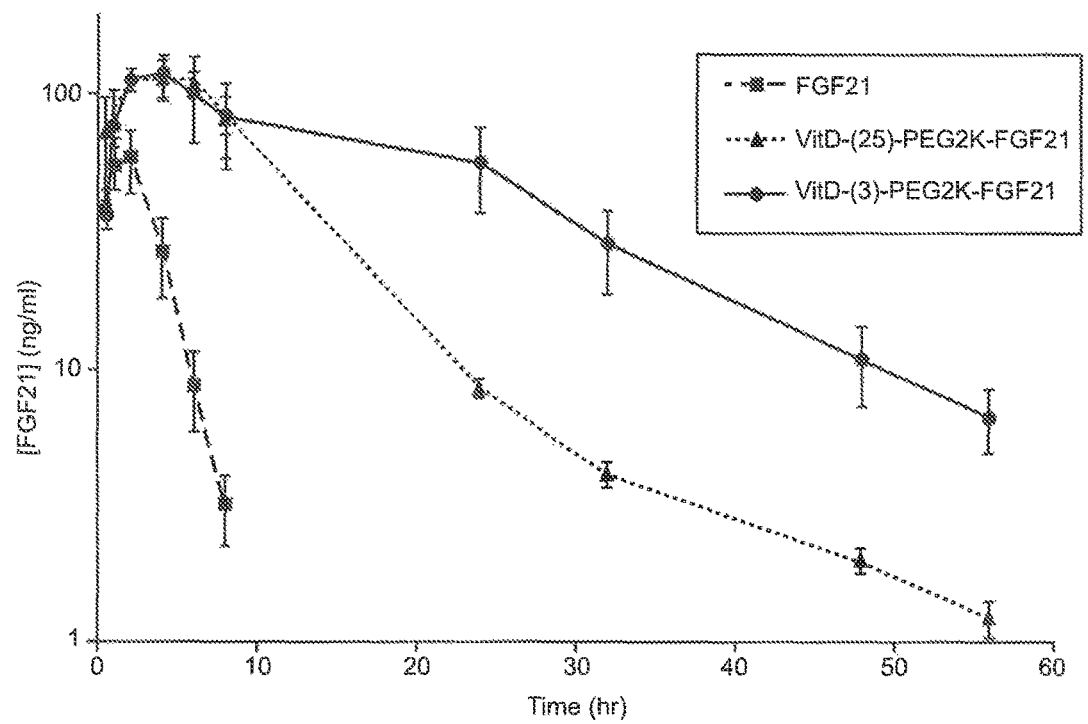
FIG. 11: Vitamin D-(3)-PEG$_{2k}$-FGF21 and Vitamin D-(25)-PEG$_{2k}$-FGF21 pharmacokinetics were compared to unmodified FGF21 upon subcutaneous injection in rats.

Unmodified FGF21, VitD-(25)-PEG$_{2K}$-FGF21 and VitD-(3)-PEG$_{2K}$-FGF21 were compared. Briefly, 0.1 mg/kg of each molecule was injected separately into the rats (n=3) by subcutaneous (sc) injection. Samples of plasma were collected at 0 hrs (pre-dose), 0.5, 1, 2, 4, 8, 24, 32, 48, and 56 hours and were immediately frozen. The samples were analyzed using commercial ELISA kits for human FGF21 (Millipore Cat. No. EZHFGF21-19K). The results show significant differences in the pharmacokinetic profiles of unconjugated FGF21 and the FGF21-carrier conjugates (FIG. 11). The pharmacokinetic profile of subcutaneously-injected FGF21 was improved when conjugated to vitamin D at the C25 and C3 positions. The best pharmacokinetic profile was obtained, however, with conjugation to the C3 position. The pharmacokinetic parameters were obtained by analyzing the data with Kinetica software (ThermoFisher) and are listed in Table 3. The half-life ($t_{1/2}$) of 5.3 hr for VitD-(25)-PEG$_{2K}$-FGF21 and 11.5 hr for VitD-(3)-PEG$_{2K}$-FGF21 represent improvements of 4.1- and 8.8-fold, respectively, compared to unmodified FGF21. Likewise, the vitamin D conjugates show improvements in bioavailability as indicated by the approximately 2-fold higher Cmax values and a 7.2-fold and 12.0-fold improvement in AUC values for the C25 and C3 conjugates, respectively. Improvements in the mean residence time (MRT) and terminal rate constant (Lz) values were also observed.

TABLE 3

| Conjugation | Cmax ng/ml | Tmax h | AUCtot h(ng/ml) | Lz 1/h | $t^{1/2}$ h | MRT h |
|---|---|---|---|---|---|---|
| None | 59 | 2 | 228 | .534 | 1.3 | 2.8 |
| C25 | 115 | 2 | 1640 | .131 | 5.3 | 7.9 |
| C3 | 118 | 4 | 2727 | .0604 | 11.5 | 18.9 |

EXEMPLARY SEQUENCES

SEQ ID NO: 1 (Apelin)
QRPRLSHKGPMPF

SEQ ID NO: 2 (human wt Oct-hGhrelin)
GS(Oct-S)FLSPEHQRVQQRKESKKPPAKLQPR

SEQ ID NO: 3 (human Oct-hGhrelin-C)
GS(Oct-S)FLSPEHQRVQQRKESKKPPAKLQPRC

SEQ ID NO: 4 (human Dap-hGhrelin)
GS S(Oct-Dap)FLSPEHQRVQQRKESKKPPAKLQPRC

SEQ ID NO: 5 (human GSY-hGhrelin)
GSYFLSPEHQRVQQRKESKKPPAKLQPRC

SEQ ID NO: 6 (rat wt Oct-rGhrelin)
GS(Oct-S)FLSPEHQKAQQPKESKKPPAKLQPR

SEQ ID NO: 7 (rat Oct-rGhrelin)
GS(Oct-S)FLSPEHQKAQQPKESKKPPAKLQPRC

SEQ ID NO: 8 (rat Dap-rGhrelin)
GS(Oct-Dap)FLSPEHQKAQQPKESKKPPAKLQPRC

SEQ ID NO: 9 (rat GSW-rGhrelin)
GSWFLSPEHQKAQQPKESKKPPAKLQPRC

SEQ ID NO: 10 (PTH (1-34))
SVSEIQLMHNLGKHLNSMERVEWLRKKLQDVHNF

EXEMPLARY SEQUENCES

SEQ ID NO: 11 (human insulin A Chain)
GIVEQCCTSICSLYQLENYCN

SEQ ID NO: 12: (human insulin B Chain)
FVNQHLCGSHLVEALYLVCGERGFFYTPKT

SEQ ID NO: 13 (human TNF-α)
MSTESMIRDVELAEEALPKKTGGPQGSRRCLFLSLFSFLIVAGATTLFCL
LHFGVIGPQREEFPRDFSFISPFAQAVRSSSRTPSDKPVAHVVANPQAEG
QFQWFNRRANAFFANGVEFRDNQFVVPSEGFYFIYSQVFFKGQGCPSTHV
FFTHTISRIAVSYQTKVNFFSAIKSPCQRETPEGAEAKPWYEPIYFGGVF
QFEKGDRFSAEINRPDYFDFAESGQVYFGIIAF SEQ ID NO: 14 (Vitamin D Binding Protein (DBP))
MKRVLVLLLAVAFGHALERGRDYEKNKVCKEFSHLGKEDFTSLSLVLYSR
KFPSGTFEQVSQFVKEVVSFTEACCAEGADPDCYDTRTSAFSAKSCESNS
PFPVHPGTAECCTKEGFERKLCMAALKHQPQEFPTYVEPTNDEICEAFRK
DPKEYANQFMWEYSTNYGQAPLSLLVSYTKSYLSMVGSCCTSASPTVCFL
KERLQLKHLSLLTTLSNRVCSQYAAYGEKKSRLSNLIKLAQKVPTADLED
VLPLAEDITNILSKCCESASEDCMAKELPEHTVKLCDNLSTKNSKFEDCC
QEKTAMDVFVCTYFMPAAQLPELPDVELPTNKDVCDPGNTKVMDKYTFEL
SRRTHLPEVFLSKVLEPTLKSLGECCDVEDSTTCFNAKGPLLKKELSSFI
DKGQELCADYSENTFTEYKKKLAERLKAKLPDATPTELAKLVNKHSDFAS
NCCSINSPPLYCDSEIDAELKNIL SEQ ID NO: 15 (Vitamin D Binding Protein (DBP))
TTTAATAATAATTCTGTGTTGCTTCTGAGATTAATAATTGATTAATTCAT
AGTCAGGAATCTTTGTAAAAAGGAAACCAATTACTTTTGGCTACCACTTT
TACATGGTCACCTACAGGAGAGAGGAGGTGCTGCAAGACTCTCTGGTAGA
AAAATGAAGAGGGTCCTGGTACTACTGCTTGCTGTGGCATTTGGACATGC
TTTAGAGAGAGGCCGGGATTATGAAAAGAATAAAGTCTGCAAGGAATTCT
CCCATCTGGGAAAGGAGGACTTCACATCTCTGTCACTAGTCCTGTACAGT
AGAAAATTTCCCAGTGGCACGTTTGAACAGGTCAGCCAACTTGTGAAGGA
AGTTGTCTCCTTGACCGAAGCCTGCTGTGCGGAAGGGGCTGACCCTGACT
GCTATGACACCAGGACCTCAGCACTGTCTGCCAAGTCCTGTGAAAGTAAT
TCTCCATTCCCCGTTCACCCAGGCACTGCTGAGTGCTGCACCAAAGAGGG
CCTGGAACGAAAGCTCTGCATGGCTGCTCTGAAACACCAGCCACAGGAAT
TCCCTACCTACGTGGAACCCACAAATGATGAAATCTGTGAGGCGTTCAGG
AAAGATCCAAAGGAATATGCTAATCAATTTATGTGGGAATATTCCACTAA
TTACGGACAAGCTCCTCTGCTCACTTTTAGTCAGTTACACCAAGAGTTATC
TTTCTATGGTAGGGTCCTGCTGTACCTCTGCAAGCCCAACTGTATGCTTT
TTGAAAGAGAGACTCCAGCTTAAACATTTATCACTTCTCACCACTCTGTC
AAATAGAGTCTGCTCACAATATGCTGCTTATGGGGAGAAGAAATCAAGGC
TCAGCAATCTCATAAAGTTAGCCCAAAAAGTGCCTACTGCTGATCTGGAG
GATGTTTTGCCACTAGCTGAAGATATTACTAACATCCTCTCCAAATGCTG
TGAGTCTGCCTCTGAAGATTGCATGGCCAAAGAGCTGCCTGAACACACAG
TAAAACTCTGTGACAATTTATCCACAAAGAATTCTAAGTTTGAAGACTGT
TGTCAAGAAAAAACAGCCATGGACGTTTTTGTGTGCACTTACTTCATGCC
AGCTGCCCAACTCCCCGAGCTTCCAGATGTAGAGTTGCCCACAAACAAAG
ATGTGTGTGATCCAGGAAACACCAAAGTCATGGATAAGTATACATTTGAA
CTAAGCAGAAGGACTCATCTTCCGGAAGTATTCCTCAGTAAGGTACTTGA
GCCAACCCTAAAAAGCCTTGGTGAATGCTGTGATGTTGAAGACTCAACTA
CCTGTTTTAATGCTAAGGGCCCTCTACTAAAGAAGGAACTATCTTCTTTC
ATTGACAAGGGACAAGAACTATGTGCAGATTATTCAGAAAATACATTTAC
TGAGTACAAGAAAAAACTGGCAGAGCGACTAAAAGCAAAATTGCCTGATG
CCACACCCACGGAACTGGCAAAGCTGGTTAACAAGCACTCAGACTTTGCC
TCCAACTGCTGTTCCATAAACTCACCTCCTCTTTACTGTGATTCAGAGAT
TGATGCTGAATTGAAGAATATCCTGTAGTCCTGAAGCATGTTTATTAACT
TTGACCAGAGTTGGAGCCACCCAGGGGAATGATCTCTGATGACCTAACCT
AAGCAAAACCACTGAGCTTCTGGGAAGACAACTAGGATACTTTCTACTTT
TTCTAGCTACAATATCTTCATACAATGACAAGTATGATGATTTGCTATCA
AAATAAATTGAAATATAATGCAAACCATAAAAAAAAAAAAAAAAAAAAA
A SEQ ID NO: 16 (C-Apelin)
CQRPRLSHKGPMPF

SEQ ID NO: 17 (PTH-C)
SVSEIQLMHNLGKHLNSMERVEWLRKKLQDVHNFC

SEQ ID NO: 18 (C-PTH)
CSVSEIQLMHNLGKHLNSMERVEWLRKKLQDVHNF

SEQ ID NO: 19 (GLP-1(7-37))
HAEGTFTSDVSSYLEGQAAKEFIAWLVKGRG

EXEMPLARY SEQUENCES

SEQ ID NO: 20 (GLP-1-C)
HAEGTFTSDVSSYLEGQAAKEFIAWLVKGRGC

SEQ ID NO: 21 (nucleotide sequence encoding FGF21 protein with I3C substitution and His6 tag (SEQ ID NO: 23))
ATGCATCATCACCATCATCACCCGTGTCCAGATTCCTCTCCTTTATTGCA
ATTCGGTGGCCAAGTTCGTCAACGCTACCTGTATACCGACGACGCCCAGC
AGACCGAAGCGCACCTTGAGATCCGTGAGGATGGTACGGTCGGTGGCGCA
GCTGACCAAAGCCCGGAGAGCCTGCTGCAGTTGAAGGCCCTGAAACCGGG
TGTTATCCAGATTCTGGGTGTGAAAACCAGCCGCTTTCTGTGCCAGCGTC
CGGATGGCGCGCTGTACGGTAGCCTGCATTTCGACCCGGAAGCGTGCTCT
TTTCGCGAGCTGCTGCTGGAAGATGGCTATAACGTGTACCAAAGCGAAGC
GCACGGTCTGCCGCTGCATCTGCCGGGTAATAAGAGCCCGCACCGCGATC
CGGCACCGCGTGGTCCGGCTCGTTTCCTGCCGTTGCCGGGTCTGCCACCG
GCGCTGCCGGAGCCGCCAGGCATTCTGGCACCGCAGCCGCCTGACGTCGG

CAGCAGCGACCCGCTGTCCATGGTTGGTCCGAGCCAGGGCCGTAGCCCGT
CGTATGCGAGCTGATAA

SEQ ID NO: 22 (FGF21 protein with I3C substitution and His6 tag (SEQ ID NO: 23))
MHHHHHHHPCPDSSPLLQFGGQVRQRYLYTDDAQQTEAHLEIREDGTVGG
AADQSPESLLQLKALKPGVIQILGVKTSRFLCQRPDGALYGSLHFDPEAC
SFRELLLEDGYNVYQSEAHGLPLHLPGNKSPHRDPAPRGPARFLPLPGLP
PALPEPPGILAPQPPDVGSSDPLSMVGPSQGRSPSYAS All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. A carrier-drug conjugate, comprising a targeting group that is a non-hormonal secosteroid vitamin D that is not hydroxylated at the carbon 1 position conjugated at the carbon 3 position to a protein having parathyroid hormone (PTH) activity, wherein said protein comprises an amino acid sequence with at least a 90% sequence identity to SEQ ID NO:10.

2. The carrier-drug conjugate of claim 1, wherein said activity is a binding of said protein to parathyroid hormone receptor 1 or parathyroid hormone receptor 2.

3. The carrier-drug conjugate of claim 1, wherein said activity increases the concentration of calcium ($Ca^{2+}$) in the blood.

4. The carrier-drug conjugate of claim 1, wherein said protein is an 84 amino acid protein.

5. The carrier-drug conjugate of claim 1, wherein said targeting group is conjugated to said protein via a scaffold.

6. The carrier-drug conjugate of claim 5, wherein said scaffold is poly(ethylene glycol).

7. A pharmaceutical composition comprising a carrier-drug conjugate comprising a targeting group that is a non-hormonal secosteroid vitamin D that is not hydroxylated at the carbon 1 position conjugated at the carbon 3 position via a scaffold to a protein having PTH activity, wherein said protein comprises an amino acid sequence with at least a 90% sequence identity to SEQ ID NO:10.

8. The pharmaceutical composition of claim 7, wherein said activity is a binding of said protein to parathyroid hormone receptor 1 or parathyroid hormone receptor 2.

9. The pharmaceutical composition of claim 7, wherein said activity increases the concentration of calcium ($Ca^{2+}$) in the blood.

10. The pharmaceutical composition of claim 7, wherein said protein is an 84 amino acid protein.

11. The pharmaceutical composition of claim 7, wherein said non-hormonal vitamin D is not hydroxylated at the carbon 1 position.

12. The pharmaceutical composition of claim 7, wherein said scaffold is poly(ethylene glycol).

13. A pharmaceutical composition, comprising:
 a) a protein having PTH activity,
 b) a targeting group that is a non-hormonal secosteroid vitamin D that is not hydroxylated at the carbon 1 position conjugated at the carbon 3 position,
 c) a scaffold stably attached to said targeting group, wherein after administration to a first test subject, said protein has a half-life measured by Enzyme Linked Immunosorbant Assay (ELISA) analysis of blood samples taken at a plurality of time points that is greater than a half-life of said protein administered to a second test subject without said stably attached scaffold moiety and targeting group as measured by said ELISA analysis of blood samples taken at said plurality of time points, wherein said protein comprises an amino acid sequence with at east a 90% sequence identity to SEQ ID NO: 10.

14. The pharmaceutical composition of claim 13, wherein said amino acid sequence of said protein is SEQ ID NO:10.

15. The pharmaceutical composition of claim 13, wherein said protein has 84 amino acids.

16. The pharmaceutical composition of claim 13, wherein said administration to said first and second subjects is accomplished by subcutaneous injection.

17. The pharmaceutical composition of claim 13, wherein said protein stably attached to said scaffold and targeting group retains about the same activity as said protein not stably attached to said scaffold and targeting group as measured by a functional assay.

18. The pharmaceutical composition of claim 13, wherein the scaffold has a mass of about 500 Da to 5,000 Da.

19. The pharmaceutical composition of claim 13, wherein said amino acid sequence of said protein is SEQ ID NO:17 or 18.

20. A carrier-drug conjugate, comprising a targeting group that is a secosteroid vitamin D that is not hydroxylated at the carbon 1 position non-releasably conjugated at the carbon 3 position to a protein having PTH activity comprising an amino acid sequence with at least a 90% sequence identity to SEQ ID NO:10.

21. The carrier-drug conjugate of claim 20, wherein said vitamin D is non-hormonal.

22. The carrier-drug conjugate of claim 21, wherein said non-hormonal vitamin D is not hydroxylated at the carbon 1 position.

23. The carrier-drug conjugate of claim 20, wherein said protein retains about the same activity as said protein not conjugated to said targeting group as measured by a functional assay.

24. The carrier-drug conjugate of claim 20, wherein said targeting group is conjugated to said protein via a scaffold that is poly(ethylene glycol).

25. The carrier-drug conjugate of claim 20, wherein said scaffold is approximately the same mass as the protein.

26. The carrier-drug conjugate of claim 20, wherein said protein comprises the sequence selected from the group consisting of SEQ ID NO: 10, 17, and 18.

* * * * *

SEQUENCE LISTING

<160> NUMBER OF SEQ ID NOS: 23

<210> SEQ ID NO 1
<211> LENGTH: 13
<212> TYPE: PRT
<213> ORGANISM: Unknown
<220> FEATURE:
<223> OTHER INFORMATION: Description of Unknown: Apelin peptide

<400> SEQUENCE: 1

Gln Arg Pro Arg Leu Ser His Lys Gly Pro Met Pro Phe
1               5                   10

<210> SEQ ID NO 2
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Octanoylated-Ser

<400> SEQUENCE: 2

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 3
<211> LENGTH: 29
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Octanoylated-Ser

<400> SEQUENCE: 3

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg Cys
            20                  25

<210> SEQ ID NO 4
<211> LENGTH: 30

```
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Octanoylated-Dap

<400> SEQUENCE: 4

Gly Ser Ser Xaa Phe Leu Ser Pro Glu His Gln Arg Val Gln Gln Arg
1               5                   10                  15

Lys Glu Ser Lys Lys Pro Pro Ala Lys Leu Gln Pro Arg Cys
            20                  25                  30

<210> SEQ ID NO 5
<211> LENGTH: 29
<212> TYPE: PRT
<213> ORGANISM: Homo sapiens

<400> SEQUENCE: 5

Gly Ser Tyr Phe Leu Ser Pro Glu His Gln Arg Val Gln Gln Arg Lys
1               5                   10                  15

Glu Ser Lys Lys Pro Pro Ala Lys Leu Gln Pro Arg Cys
            20                  25

<210> SEQ ID NO 6
<211> LENGTH: 28
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Octanoylated-Ser

<400> SEQUENCE: 6

Gly Ser Ser Phe Leu Ser Pro Glu His Gln Lys Ala Gln Gln Pro Lys
1               5                   10                  15

Glu Ser Lys Lys Pro Pro Ala Lys Leu Gln Pro Arg
            20                  25

<210> SEQ ID NO 7
<211> LENGTH: 29
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Octanoylated-Ser

<400> SEQUENCE: 7

Gly Ser Ser Phe Leu Ser Pro Glu His Gln Lys Ala Gln Gln Pro Lys
1               5                   10                  15

Glu Ser Lys Lys Pro Pro Ala Lys Leu Gln Pro Arg Cys
            20                  25

<210> SEQ ID NO 8
<211> LENGTH: 29
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Octanoylated-Dap

<400> SEQUENCE: 8

Gly Ser Xaa Phe Leu Ser Pro Glu His Gln Lys Ala Gln Gln Pro Lys
1               5                   10                  15
```

Glu Ser Lys Lys Pro Pro Ala Lys Leu Gln Pro Arg Cys
            20                  25

<210> SEQ ID NO 9
<211> LENGTH: 29
<212> TYPE: PRT
<213> ORGANISM: Rattus norvegicus

<400> SEQUENCE: 9

Gly Ser Trp Phe Leu Ser Pro Glu His Gln Lys Ala Gln Gln Pro Lys
1               5                   10                  15

Glu Ser Lys Lys Pro Pro Ala Lys Leu Gln Pro Arg Cys
            20                  25

<210> SEQ ID NO 10
<211> LENGTH: 34
<212> TYPE: PRT
<213> ORGANISM: Homo sapiens

<400> SEQUENCE: 10

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 11
<211> LENGTH: 21
<212> TYPE: PRT
<213> ORGANISM: Homo sapiens

<400> SEQUENCE: 11

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 12
<211> LENGTH: 30
<212> TYPE: PRT
<213> ORGANISM: Homo sapiens

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 13
<211> LENGTH: 233
<212> TYPE: PRT
<213> ORGANISM: Homo sapiens

<400> SEQUENCE: 13

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

```
Cys Leu Leu His Phe Gly Val Ile Gly Pro Gln Arg Glu Glu Phe Pro
    50                  55                  60

Arg Asp Phe Ser Phe Ile Ser Pro Phe Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Phe Gln Trp Phe Asn Arg Arg Ala Asn Ala Phe
            100                 105                 110

Phe Ala Asn Gly Val Glu Phe Arg Asp Asn Gln Phe Val Val Pro Ser
            115                 120                 125

Glu Gly Phe Tyr Phe Ile Tyr Ser Gln Val Phe Phe Lys Gly Gln Gly
        130                 135                 140

Cys Pro Ser Thr His Val Phe Phe Thr His Thr Ile Ser Arg Ile Ala
145                 150                 155                 160

Val Ser Tyr Gln Thr Lys Val Asn Phe Phe Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Phe Gly Gly Val Phe Gln Phe Glu Lys Gly Asp Arg Phe
            195                 200                 205

Ser Ala Glu Ile Asn Arg Pro Asp Tyr Phe Asp Phe Ala Glu Ser Gly
        210                 215                 220

Gln Val Tyr Phe Gly Ile Ile Ala Phe
225                 230

<210> SEQ ID NO 14
<211> LENGTH: 474
<212> TYPE: PRT
<213> ORGANISM: Homo sapiens

<400> SEQUENCE: 14

Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Phe Val
    50                  55                  60

Lys Glu Val Val Ser Phe Thr Glu Ala Cys Cys Ala Glu Gly Ala Asp
65                  70                  75                  80

Pro Asp Cys Tyr Asp Thr Arg Thr Ser Ala Phe Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Phe Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190
```

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
    370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
            420                 425                 430

Ala Thr Pro Thr Glu Leu Ala Lys Leu Val Asn Lys His Ser Asp Phe
        435                 440                 445

Ala Ser Asn Cys Cys Ser Ile Asn Ser Pro Pro Leu Tyr Cys Asp Ser
    450                 455                 460

Glu Ile Asp Ala Glu Leu Lys Asn Ile Leu
465                 470

<210> SEQ ID NO 15
<211> LENGTH: 1801
<212> TYPE: DNA
<213> ORGANISM: Homo sapiens

<400> SEQUENCE: 15
tttaataata attctgtgtt gcttctgaga ttaataattg attaattcat agtcaggaat    60
ctttgtaaaa aggaaaccaa ttacttttgg ctaccacttt tacatggtca cctacaggag   120
agaggaggtg ctgcaagact ctctggtaga aaaatgaaga gggtcctggt actactgctt   180
gctgtggcat ttggacatgc tttagagaga ggccgggatt atgaaaagaa taaagtctgc   240
aaggaattct cccatctggg aaaggaggac ttcacatctc tgtcactagt cctgtacagt   300
agaaaatttc ccagtggcac gtttgaacag gtcagccaac ttgtgaagga agttgtctcc   360
ttgaccgaag cctgctgtgc ggaaggggct gaccctgact gctatgacac caggacctca   420
gcactgtctg ccaagtcctg tgaaagtaat tctccattcc ccgttcaccc aggcactgct   480

-continued

```
gagtgctgca ccaaagaggg cctggaacga aagctctgca tggctgctct gaaacaccag    540
ccacaggaat tccctaccta cgtggaaccc acaaatgatg aaatctgtga ggcgttcagg    600
aaagatccaa aggaatatgc taatcaattt atgtgggaat attccactaa ttacggacaa    660
gctcctctgt cacttttagt cagttacacc aagagttatc tttctatggt agggtcctgc    720
tgtacctctg caagcccaac tgtatgcttt ttgaaagaga actccagct taaacattta    780 tcacttctca ccactctgtc aaatagagtc tgctcacaat atgctgctta tggggagaag    840
aaatcaaggc tcagcaatct cataaagtta gcccaaaaag tgcctactgc tgatctggag    900
gatgttttgc cactagctga agatattact aacatcctct ccaaatgctg tgagtctgcc    960
tctgaagatt gcatggccaa agagctgcct gaacacacag taaaactctg tgacaattta   1020
tccacaaaga attctaagtt tgaagactgt tgtcaagaaa aacagccat ggacgttttt   1080 gtgtgcactt acttcatgcc agctgcccaa ctccccgagc ttccagatgt agagttgccc   1140
acaaacaaag atgtgtgtga tccaggaaac accaaagtca tggataagta tacatttgaa   1200
ctaagcagaa ggactcatct tccggaagta ttcctcagta aggtacttga gccaacccta   1260
aaaagccttg gtgaatgctg tgatgttgaa gactcaacta cctgttttaa tgctaagggc   1320
cctctactaa agaaggaact atcttctttc attgacaagg acaagaact atgtgcagat   1380 tattcagaaa atacatttac tgagtacaag aaaaaactgg cagagcgact aaaagcaaaa   1440
ttgcctgatg ccacacccac ggaactggca aagctggtta caagcactc agactttgcc   1500 tccaactgct gttccataaa ctcacctcct ctttactgtg attcagagat tgatgctgaa   1560
ttgaagaata tcctgtagtc ctgaagcatg tttattaact ttgaccagag ttggagccac   1620 ccagggggaat gatctctgat gacctaacct aagcaaaacc actgagcttc tgggaagaca   1680
actaggatac tttctacttt ttctagctac aatatcttca tacaatgaca agtatgatga   1740
tttgctatca aaataaattg aaatataatg caaaccataa aaaaaaaaa aaaaaaaaa   1800 a                                                                  1801
```

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Cys Gln Arg Pro Arg Leu Ser His Lys Gly Pro Met Pro Phe
1               5                   10

<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Cys
            35

<210> SEQ ID NO 18
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Cys Ser Val Ser Glu Ile Gln Leu Met His Asn Leu Gly Lys His Leu
1               5                   10                  15

Asn Ser Met Glu Arg Val Glu Trp Leu Arg Lys Lys Leu Gln Asp Val
            20                  25                  30

His Asn Phe
        35

<210> SEQ ID NO 19
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Cys
            20                  25                  30

<210> SEQ ID NO 21
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgcatcatc accatcatca cccgtgtcca gattcctctc ctttattgca attcggtggc      60
caagttcgtc aacgctacct gtataccgac gacgcccagc agaccgaagc gcaccttgag     120
atccgtgagg atggtacggt cggtggcgca gctgaccaaa gcccggagag cctgctgcag     180
ttgaaggccc tgaaaccggg tgttatccag attctgggtg tgaaaaccag ccgctttctg     240
tgccagcgtc cggatggcgc gctgtacggt agcctgcatt tcgacccgga agcgtgctct     300
tttcgcgagc tgctgctgga agatggctat aacgtgtacc aaagcgaagc gcacggtctg     360
ccgctgcatc tgccgggtaa taagagcccg caccgcgatc cggcaccgcg tggtccggct     420

```
cgtttcctgc cgttgccggg tctgccaccg gcgctgccgg agccgccagg cattctggca    480
ccgcagccgc ctgacgtcgg cagcagcgac ccgctgtcca tggttggtcc gagccagggc    540
cgtagcccgt cgtatgcgag ctgataa                                        567
```

<210> SEQ ID NO 22
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met His His His His His His Pro Cys Pro Asp Ser Ser Pro Leu
1               5                   10                  15

Leu Gln Phe Gly Gly Gln Val Arg Gln Arg Tyr Leu Tyr Thr Asp Asp
            20                  25                  30

Ala Gln Gln Thr Glu Ala His Leu Glu Ile Arg Glu Asp Gly Thr Val
        35                  40                  45

Gly Gly Ala Ala Asp Gln Ser Pro Glu Ser Leu Leu Gln Leu Lys Ala
    50                  55                  60

Leu Lys Pro Gly Val Ile Gln Ile Leu Gly Val Lys Thr Ser Arg Phe
65                  70                  75                  80

Leu Cys Gln Arg Pro Asp Gly Ala Leu Tyr Gly Ser Leu His Phe Asp
                85                  90                  95

Pro Glu Ala Cys Ser Phe Arg Glu Leu Leu Leu Glu Asp Gly Tyr Asn
            100                 105                 110

Val Tyr Gln Ser Glu Ala His Gly Leu Pro Leu His Leu Pro Gly Asn
        115                 120                 125

Lys Ser Pro His Arg Asp Pro Ala Pro Arg Gly Pro Ala Arg Phe Leu
    130                 135                 140

Pro Leu Pro Gly Leu Pro Pro Ala Leu Pro Glu Pro Gly Ile Leu
145                 150                 155                 160

Ala Pro Gln Pro Pro Asp Val Gly Ser Ser Asp Pro Leu Ser Met Val
                165                 170                 175

Gly Pro Ser Gln Gly Arg Ser Pro Ser Tyr Ala Ser
            180                 185

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5